United States Patent
Anderson et al.

(10) Patent No.: US 9,833,505 B1
(45) Date of Patent: Dec. 5, 2017

(54) VACCINE COMPOSITIONS FOR TREATMENT OF ZIKA VIRUS

(71) Applicant: Variation Biotechnologies Inc., Ottawa (CA)

(72) Inventors: David E. Anderson, Boston, MA (US); Anne-Catherine Fluckiger, Saint Genis les Ollières (FR)

(73) Assignee: Variation Biotechnologies Inc., Ottawa (CA)

( * ) Notice: Subject to any disclaimer, the term of this patent is extended or adjusted under 35 U.S.C. 154(b) by 0 days.

(21) Appl. No.: 15/642,950

(22) Filed: Jul. 6, 2017

Related U.S. Application Data

(60) Provisional application No. 62/413,007, filed on Oct. 26, 2016, provisional application No. 62/363,545, filed on Jul. 18, 2016.

(51) Int. Cl.
*A61K 39/12* (2006.01)
*C12N 7/00* (2006.01)
*A61K 39/00* (2006.01)

(52) U.S. Cl.
CPC ........... *A61K 39/12* (2013.01); *C12N 7/00* (2013.01); *A61K 2039/5258* (2013.01); *A61K 2039/55505* (2013.01); *A61K 2039/57* (2013.01); *A61K 2039/575* (2013.01); *A61K 2039/70* (2013.01); *C12N 2740/13022* (2013.01); *C12N 2740/13023* (2013.01); *C12N 2740/13034* (2013.01); *C12N 2770/24122* (2013.01); *C12N 2770/24123* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 5,500,161 | A | 3/1996 | Andrianov et al. |
| 6,210,922 | B1 | 4/2001 | Cote et al. |
| 8,920,812 | B2 | 12/2014 | Haynes |

FOREIGN PATENT DOCUMENTS

| | | |
|---|---|---|
| CA | 2252972 A1 | 5/2000 |

OTHER PUBLICATIONS

Thomas, S., New England Journal of Medicine, May 2017, 376(19):1883-1886. (Year: 2017).*
Morrison et al., Journal of Virology, Apr. 2017, 19(8), e00009-17, 15 pages. (Year: 2017).*
Guirakhoo, F. et al., Development of a Zika vaccine using a novel MVA-VLP platform, Abstracts / Int. J. Infect. Dis., 53S(08.2010):16-17 (2016).
International Search Report for PCT/CA2017/050822, 6 pages (Sep. 20, 2017).
Kushnir, N. et al., Virus-like particles as a highly efficient vaccine platform: Diversity of targets and production systems and advances in clinical development, Vaccine, 31: 58-83 (2012).
Tripp, R. et al., Development of a Zika vaccine, Expert Review of Vaccines, 15(9): 1083-1085 (2016).
Written Opinion for PCT/CA2017/050822, 7 pages (dated Sep. 20, 2017).
Broer, R. et al., Important Role for the Transmembrane Domain of Severe Acute Respiratory Syndrome Coronavirus Spike Protein during Entry, 80(3):1302-1310 (2006).
Cao-Lormeau, V.M. et al., Guillain-Barre Syndrome outbreak associated with Zika virus infection in French Polynesia: a case-control study, Lancet, 387(10027):1531-1539 (2016).
Compton, T. et al., A sorting signal for the basolateral delivery of the vesicular stomatitis virus (VSV) G protein lies in its luminal domain: analysis of the targeting of VSV G-influenza hemagglutinin chimeras, Proc Natl Acad Sci USA, 86(11):4112-4116 (1989).
Crook, K.R. et al., Modulation of innate immune signaling by the secreted form of the West Nile virus NS1 glycoprotein, Virology, 458-459:172-182 (2014).
Faye, O. et al., Molecular Evolution of Zika Virus during Its Emergence in the 20th Century, PLoS Negl Trop Dis., 8(1):e2636 (2014).
Ferraro, B. et al., Clinical applications of DNA vaccines: current progress, Clin Infect Dis, 53(3):296-302 (2011).
Garrone, P. et al., a Prime-Boost Strategy Using Virus-Like Particles Pseudotyped for HCV Proteins Triggers Broadly Neutralizing Antibodies in Macaques, Science Translational Medicine, 3(94):94ra71 (2011).
Govero, J. et al., Zika virus infection damages the testes in mice, Nature, 540(7633):438-442 (2016).
Kirchmeier, M. et al., Enveloped virus-like particle expression of human cytomegalovirus glycoprotein B antigen induces antibodies with potent and broad neutralizing activity, Clin Vaccine Immunol., 21(2):174-180 (2014).
Kumar P. et al., Healthy Chidren With a History of Subclinical Infection With Japanese Encephalitis Virus: Analysis of CD4+ and CD8+ Cell Traget Specificities by Intracellular Delivery of Viral Proteins Using the Human Immunodeficiency Virus Tat Protein Transduction Domain, J. Gen. Virol., 82(Pt2):471-482 (2004).
Larocca, R.A. et al., Vaccine protection against Zika virus from Brazil, Nature, 536(7617):474-478 (2016).
Lee, E. et al., Both E protein glycans adversely affect dengue virus infectivity but are beneficial for virion release, J Virol., 84(10):5171-5180 (2010).
Lemaitre, M. et al., Seasonal H1N1 2007 influenza virus infection is associated with elevated pre-exposure antibody titers to the 2009 pandemic influenza A (H1N1) virus, Clin Microbiol Infect., 17(5):732-737 (2011).
Levy, C. et al., Virus-like particle vaccine induces cross-protection against human metapneumovirus infections, Vaccine, 31(25):2778-2785 (2013).

(Continued)

*Primary Examiner* — Stacy B Chen

(74) *Attorney, Agent, or Firm* — Choate, Hall & Stewart LLP; Brenda Herschbach Jarrell; Rolando Medina

(57) ABSTRACT

The present disclosure provides compositions and methods useful for preventing and treating Zika virus infection. As described herein, the compositions and methods are based on development of immunogenic compositions that include virus-like particles (VLPs) which comprise one or more Moloney Murine leukemia virus (MMLV) core proteins and include one or more Zika epitopes, such as, for example, from Zika envelope glycoprotein E and the Zika structural protein NS1 including variants thereof.

17 Claims, 9 Drawing Sheets

(56) References Cited

OTHER PUBLICATIONS

Mammano, F. et al., Truncation of the human immunodeficiency virus type 1 envelope glycoprotein allows efficient pseudotyping of Moloney murine leukemia virus particles and gene transfer into CD4+ cells, J Virol, 71(4):3341-3345 (1997).

Phillips, N.C. and Emili, A., Enhanced antibody response to liposome-associated protein antigens: preferential stimulation of IgG2a/b production, Vaccine, 10(3):151-158 (1992).

Rivino, L. et al., Differential targeting of viral components by CD4+ versus CD8+ T lymphocytes in dengue virus infection, J Virol., 87(5):2693-2706 (2013).

Roldao, A. et al., Virus-like particles in vaccine development, Exper Rev Vaccines, 9(10):1149-1176 (2010).

Russell, P.K. and Nisalak, A., Dengue virus identification by the plaque reduction neutralization test, J Immunol., 99(2):291-296 (1967).

Samarasekara, U. and Triunfol, M., Concern over Zika virus grips the world, Lancet, 387(10018):521-524 (2016).

Sharma, S. et al., Noninfectious virus-like particles produced by Moloney murine leukemia virus-based retrovirus packaging cells deficient in viral envelope become infectious in the presence of lipofection reagants, Proc Natl Acad Sci USA, 94(20):10803-10808 (1997).

Sirohi, D. et al., The 3.8 Angstrom resolution cryo-EM structure of Zika Virus, Science, 352(6284):467-470 (2016).

Soares De Oliveira-Szejnfeld, P. et al., Congenitcal Brain Abnormalities and Zika Virus, Radiology, 281(1):203-218 (2016).

Turtle, L. et al., Human T cell responses to Japanese encephalitis virus in health and disease, J Exp Med., 213(7):1331-1352 (2016).

\* cited by examiner

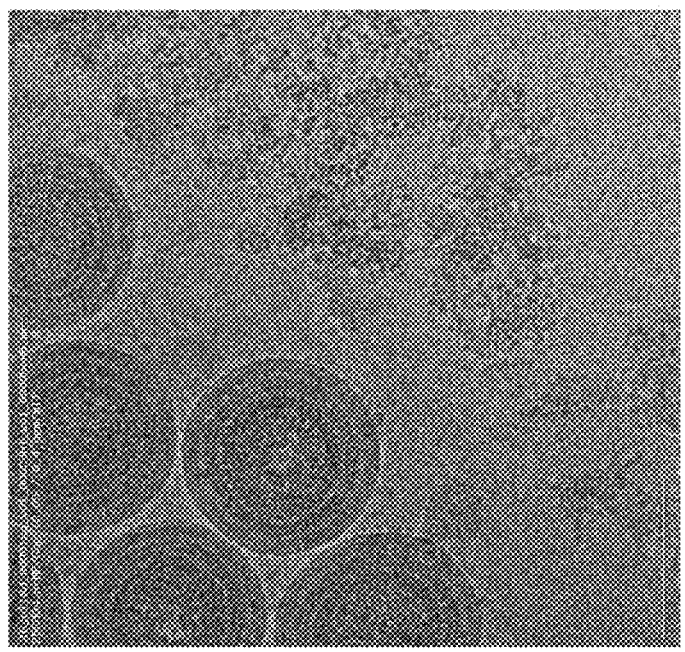
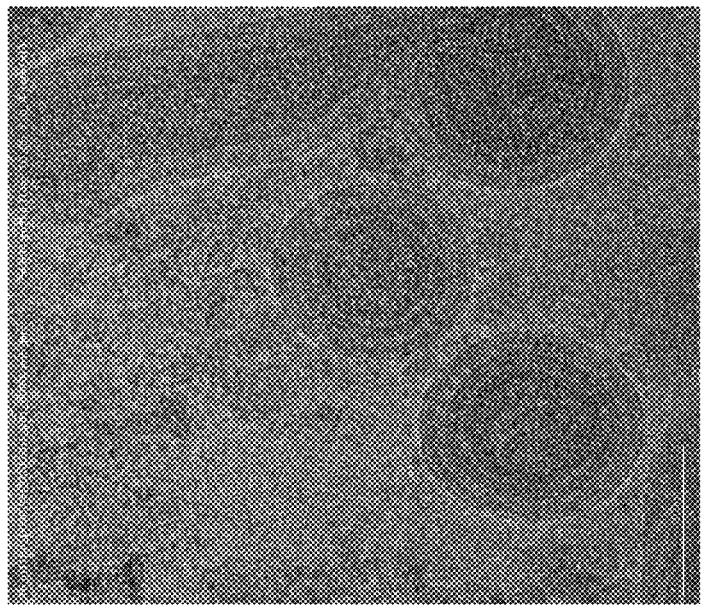
Figure 7

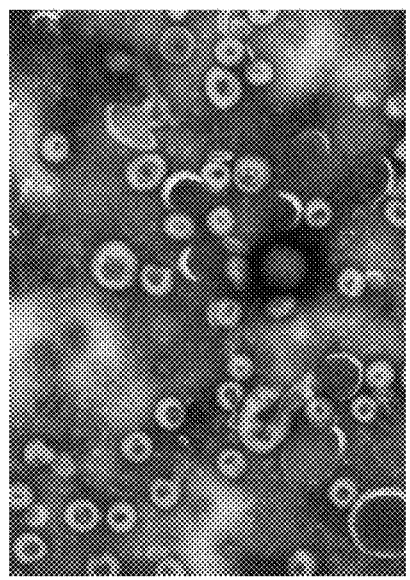
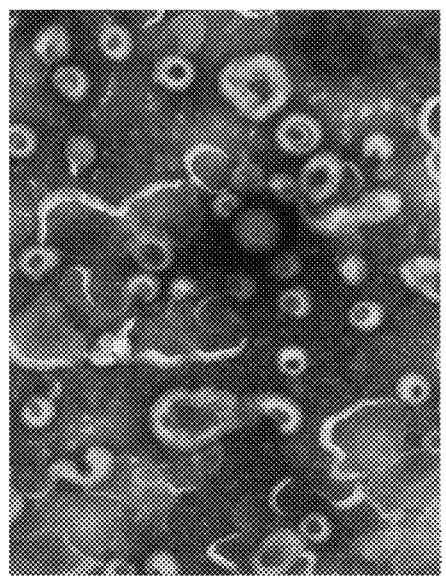
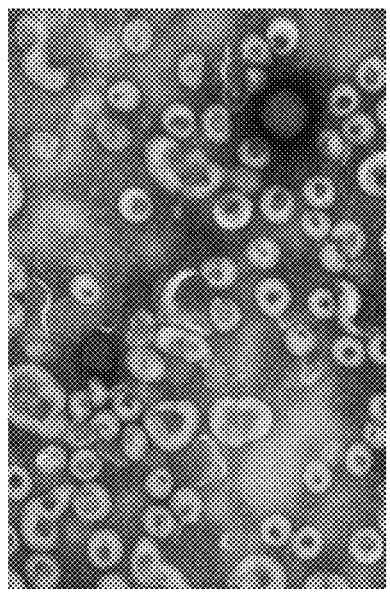
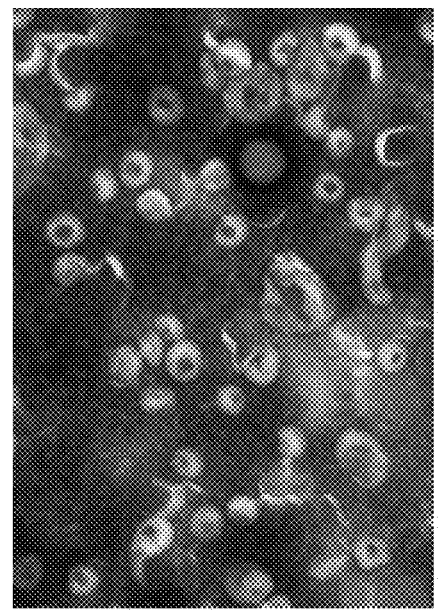
Figure 6

SEQUENCE LISTING

<160> NUMBER OF SEQ ID NOS: 25

<210> SEQ ID NO 1
<211> LENGTH: 538
<212> TYPE: PRT
<213> ORGANISM: Moloney murine leukemia virus

<400> SEQUENCE: 1

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365
```

| | | | | | | | | | | | |
|---|---|---|---|---|---|---|---|---|---|---|---|
|Leu|Glu|Arg|Leu|Lys|Glu|Ala|Tyr|Arg|Arg|Tyr|Thr|Pro|Tyr|Asp|Pro|
| |370| | | |375| | | |380| | | | | | |

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Glu Arg Ile Arg Arg Glu Thr
                435                 440                 445

Glu Glu Lys Glu Glu Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg
            485                 490                 495

Ser Gln Leu Asp Arg Asp Gln Cys Ala Tyr Cys Lys Glu Lys Gly His
                500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp
            530                 535

<210> SEQ ID NO 2
<211> LENGTH: 1614
<212> TYPE: DNA
<213> ORGANISM: Moloney murine leukemia virus

<400> SEQUENCE: 2

```
atgggccaga ctgttaccac tcccttaagt ttgaccttag gtcactggaa agatgtcgag      60
cggatcgctc acaaccagtc ggtagatgtc aagaagagac gttgggttac cttctgctct     120
gcagaatggc caacctttaa cgtcggatgg ccgcgagacg gcacctttaa ccgagacctc     180
atcacccagg ttaagatcaa ggtcttttca cctggcccgc atggacaccc agaccaggtc     240
ccctacatcg tgacctggga agccttggct tttgaccccc ctccctgggt caagcccttt     300
gtacaccctc agcctccgcc tcctcttcct ccatccgccc cgtctctccc ccttgaacct     360
cctcgttcga ccccgcctcg atcctccctt tatccagccc tcactccttc tctaggcgcc     420
aaacctaaac ctcaagttct ttctgacagt ggggggccgc tcatcgacct acttacagaa     480
gacccccgc cttatagga cccaagacca ccccccttccg acaggacgg aaatggtgga      540
gaagcgaccc ctgcgggaga ggcaccggac ccctccccaa tggcatctcg cctacgtggg     600
agacgggagc ccctgtggc cgactccact acctcgcagg cattcccct ccgcgcagga     660
ggaaacggac agcttcaata ctggccgttc tcctcttctg accttacaa ctggaaaaat     720
aataaccctt ctttttctga agatccaggt aaactgacag ctctgatcga gtctgttctc     780
atcacccatc agcccacctg gacgactgt cagcagctgt ggggactct gctgaccgga     840
gaagaaaaac aacgggtgct cttagaggct agaaaggcgg tcggggcga tgatgggcgc     900
ccactcaac tgcccaatga agtcgatgcc gcttttcccc tcgagcgccc agactggat     960
tacaccaccc aggcaggtag gaaccaccta gtccactatc gccagttgct cctagcgggt    1020
ctccaaaacg cgggcagaag ccccaccaat ttggccaagg taaaggaat aacacaaggg    1080
cccaatgagt ctccctcggc cttcctagag agacttaagg aagcctatcg caggtacact    1140
```

| | |
|---|---|
| ccttatgacc ctgaggaccc agggcaagaa actaatgtgt ctatgtcttt catttggcag | 1200 |
| tctgccccag acattgggag aaagttagag aggttagaag atttaaaaaa caagacgctt | 1260 |
| ggagatttgg ttagagaggc agaaaagatc tttaataaac gagaaacccc ggaagaaaga | 1320 |
| gaggaacgta tcaggagaga aacagaggaa aagaagaac gccgtaggac agaggatgag | 1380 |
| cagaaagaga agaaagaga tcgtaggaga catagagaga tgagcaagct attggccact | 1440 |
| gtcgttagtg gacagaaaca ggatagacag ggaggagaac gaaggaggtc ccaactcgat | 1500 |
| cgcgaccagt gtgcctactg caaagaaaag gggcactggg ctaaagattg tcccaagaaa | 1560 |
| ccacgaggac ctcggggacc aagaccccag acctccctcc tgaccctaga tgac | 1614 |

<210> SEQ ID NO 3
<211> LENGTH: 1614
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| atgggacaga ccgtcacaac acccctgagc ctgaccctgg acattggaa agacgtggag | 60 |
| aggatcgcac ataaccagag cgtggacgtg aagaaacgga gatgggtcac attctgcagt | 120 |
| gctgagtggc aacttttaa tgtgggatgg ccccgagacg gctttcaa cagggatctg | 180 |
| atcacccagg tgaagatcaa ggtctttagc ccaggacctc acggacatcc agaccaggtg | 240 |
| ccttatatcg tcacctggga ggcactggcc ttcgatcccc ctccatgggt gaagccattt | 300 |
| gtccacccaa aaccacctcc accactgcct ccaagtgccc cttcactgcc actggaacca | 360 |
| ccccggagca caccccccg cagctccctg tatcctgctc tgactccatc tctgggcgca | 420 |
| aagccaaaac cacaggtgct gagcgactcc ggaggaccac tgattgacct gctgacagag | 480 |
| gacccccac cataccgaga tcctcggcct ccaccaagcg accgcgatgg aaatggagga | 540 |
| gaggctactc ctgccggcga agcccctgac ccatctccaa tggctagtag gctgcgcggc | 600 |
| aggcgcgagc ctccagtggc agatagcacc acatcccagg ccttccctct gagggctggg | 660 |
| ggaaatgggc agctccagta ttggccattt tctagttcag acctgtacaa ctggaagaac | 720 |
| aataacccct ctttcagtga ggaccccggc aaactgaccg ccctgatcga atccgtgctg | 780 |
| attacccatc agcccacatg ggacgattgt cagcagctcc tgggcaccct gctgaccgga | 840 |
| gaggaaaagc agcgcgtgct gctggaggct cgcaaagcag tccgagggga cgatggacgg | 900 |
| cccacacagc tccctaatga ggtggacgcc gcttttccac tggaaagacc cgactgggat | 960 |
| tatactaccc aggcagggag aaaccacctg gtccattaca ggcagctcct gctggcaggc | 1020 |
| ctgcagaatg ccgggagatc ccccaccaac ctggccaagg tgaaaggcat acacaggggg | 1080 |
| cctaatgagt caccaagcgc ctttctggag aggctgaagg aagcttaccg acggtatacc | 1140 |
| ccatacgacc ctgaggaccc cggacaggaa acaaacgtct ccatgtcttt catctggcag | 1200 |
| tctgccccag acattgggcg gaagctggag agactggaag acctgaagaa caagaccctg | 1260 |
| ggcgacctgg tgcgggaggc tgaaaagatc ttcaacaaac gggagacccc cgaggaaaga | 1320 |
| gaggaaagga ttagaaggga aactgaggaa aggaggaac gccgacgac cgaggacgaa | 1380 |
| cagaaggaga agaacgaga tcggcggcgg caccgggaga tgtcaaagct gctggccacc | 1440 |
| gtggtcagcg gacagaaaca ggacagacag ggaggagagc gacggagaag ccagctcgac | 1500 |
| agggatcagt gcgcatactg taaggaaaaa ggccattggg ccaaggattg ccccaaaaag | 1560 |

-continued

```
ccaagaggac caagaggacc aagaccacag acatcactgc tgaccctgga cgac    1614
```

<210> SEQ ID NO 4
<211> LENGTH: 704
<212> TYPE: PRT
<213> ORGANISM: Zika virus

<400> SEQUENCE: 4

```
Met Leu Arg Ile Ile Asn Ala Arg Lys Glu Lys Lys Arg Arg Gly Ala
1               5                   10                  15

Asp Thr Ser Val Gly Ile Val Gly Leu Leu Leu Thr Thr Ala Met Ala
                20                  25                  30

Ala Glu Val Thr Arg Arg Gly Ser Ala Tyr Tyr Met Tyr Leu Asp Arg
            35                  40                  45

Asn Asp Ala Gly Glu Ala Ile Ser Phe Pro Thr Thr Leu Gly Met Asn
        50                  55                  60

Lys Cys Tyr Ile Gln Ile Met Asp Leu Gly His Thr Cys Asp Ala Thr
65                  70                  75                  80

Met Ser Tyr Glu Cys Pro Met Leu Asp Glu Gly Val Glu Pro Asp Asp
                85                  90                  95

Val Asp Cys Trp Cys Asn Thr Thr Ser Thr Trp Val Val Tyr Gly Thr
            100                 105                 110

Cys His His Lys Lys Gly Glu Ala Arg Arg Ser Arg Arg Ala Val Thr
        115                 120                 125

Leu Pro Ser His Ser Thr Arg Lys Leu Gln Thr Arg Ser Gln Thr Trp
    130                 135                 140

Leu Glu Ser Arg Glu Tyr Thr Lys His Leu Ile Arg Val Glu Asn Trp
145                 150                 155                 160

Ile Phe Arg Asn Pro Gly Phe Ala Leu Ala Ala Ala Ala Ile Ala Trp
                165                 170                 175

Leu Leu Gly Ser Ser Thr Ser Gln Lys Val Ile Tyr Leu Val Met Ile
            180                 185                 190

Leu Leu Ile Ala Pro Ala Tyr Ser Ile Arg Cys Ile Gly Val Ser Asn
        195                 200                 205

Arg Asp Phe Val Glu Gly Met Ser Gly Gly Thr Trp Val Asp Val Val
    210                 215                 220

Leu Glu His Gly Gly Cys Val Thr Val Met Ala Gln Asp Lys Pro Thr
225                 230                 235                 240

Val Asp Ile Glu Leu Val Thr Thr Thr Val Ser Asn Met Ala Glu Val
                245                 250                 255

Arg Ser Tyr Cys Tyr Glu Ala Ser Ile Ser Asp Met Ala Ser Asp Ser
            260                 265                 270

Arg Cys Pro Thr Gln Gly Glu Ala Tyr Leu Asp Lys Gln Ser Asp Thr
        275                 280                 285

Gln Tyr Val Cys Lys Arg Thr Leu Val Asp Arg Gly Trp Gly Asn Gly
    290                 295                 300

Cys Gly Leu Phe Gly Lys Gly Ser Leu Val Thr Cys Ala Lys Phe Ala
305                 310                 315                 320

Cys Ser Lys Lys Met Thr Gly Lys Ser Ile Gln Pro Glu Asn Leu Glu
                325                 330                 335

Tyr Arg Ile Met Leu Ser Val His Gly Ser Gln His Ser Gly Met Ile
            340                 345                 350

Val Asn Asp Thr Gly His Glu Thr Asp Glu Asn Arg Ala Lys Val Glu
        355                 360                 365
```

-continued

```
Ile Thr Pro Asn Ser Pro Arg Ala Glu Ala Thr Leu Gly Gly Phe Gly
    370                 375                 380

Ser Leu Gly Leu Asp Cys Glu Pro Arg Thr Gly Leu Asp Phe Ser Asp
385                 390                 395                 400

Leu Tyr Tyr Leu Thr Met Asn Asn Lys His Trp Leu Val His Lys Glu
                405                 410                 415

Trp Phe His Asp Ile Pro Leu Pro Trp His Ala Gly Ala Asp Thr Gly
            420                 425                 430

Thr Pro His Trp Asn Asn Lys Glu Ala Leu Val Glu Phe Lys Asp Ala
        435                 440                 445

His Ala Lys Arg Gln Thr Val Val Val Leu Gly Ser Gln Glu Gly Ala
    450                 455                 460

Val His Thr Ala Leu Ala Gly Ala Leu Glu Ala Glu Met Asp Gly Ala
465                 470                 475                 480

Lys Gly Arg Leu Ser Ser Gly His Leu Lys Cys Arg Leu Lys Met Asp
                485                 490                 495

Lys Leu Arg Leu Lys Gly Val Ser Tyr Ser Leu Cys Thr Ala Ala Phe
            500                 505                 510

Thr Phe Thr Lys Ile Pro Ala Glu Thr Leu His Gly Thr Val Thr Val
        515                 520                 525

Glu Val Gln Tyr Ala Gly Thr Asp Gly Pro Cys Lys Val Pro Ala Gln
    530                 535                 540

Met Ala Val Asp Met Gln Thr Leu Thr Pro Val Gly Arg Leu Ile Thr
545                 550                 555                 560

Ala Asn Pro Val Ile Thr Glu Ser Thr Glu Asn Ser Lys Met Met Leu
                565                 570                 575

Glu Leu Asp Pro Pro Phe Gly Asp Ser Tyr Ile Val Ile Gly Val Gly
            580                 585                 590

Glu Lys Lys Ile Thr His His Trp His Arg Ser Gly Ser Thr Ile Gly
        595                 600                 605

Lys Ala Phe Glu Ala Thr Val Arg Gly Ala Lys Arg Met Ala Val Leu
    610                 615                 620

Gly Asp Thr Ala Trp Asp Phe Gly Ser Val Gly Gly Ala Leu Asn Ser
625                 630                 635                 640

Leu Gly Lys Gly Ile His Gln Ile Phe Gly Ala Ala Phe Lys Ser Leu
                645                 650                 655

Phe Gly Gly Met Ser Trp Phe Ser Gln Ile Leu Ile Gly Thr Leu Leu
            660                 665                 670

Met Trp Leu Gly Leu Asn Ala Lys Asn Gly Ser Ile Ser Leu Met Cys
        675                 680                 685

Leu Ala Leu Gly Gly Val Leu Ile Phe Leu Ser Thr Ala Val Ser Ala
    690                 695                 700
```

<210> SEQ ID NO 5
<211> LENGTH: 2115
<212> TYPE: DNA
<213> ORGANISM: Zika virus

<400> SEQUENCE: 5

```
atgctgagaa taatcaatgc taggaaggag aagaagagac gaggcgcaga tactagtgtc      60
ggaattgttg gcctcctgct gaccacagct atggcagcgg aggtcactag acgtgggagt     120
gcatactata tgtacttgga cagaaacgat gctggggagg ccatatcttt tccaaccaca     180
ttggggatga ataagtgtta tatacagatc atggatcttg gacacacgtg tgatgccacc     240
```

```
atgagctatg aatgccctat gctggatgag ggggtggaac cagatgacgt cgattgttgg      300
tgcaacacga cgtcaacttg ggttgtgtac ggaacctgcc atcacaaaaa aggtgaagca      360
cggagatcta gaagagctgt gacgctcccc tcccattcca ctaggaagct gcaaacgcgg      420
tcgcaaacct ggttggaatc aagagaatac acaaagcact tgattagagt cgaaaattgg      480
atattcagga accctggctt cgcgttagca gcagctgcca tcgcttggct tttgggaagc      540
tcaacgagcc aaaaagtcat atacttggtc atgatactgc tgattgcccc ggcatacagc      600
atcaggtgca taggagtcag caatagggac tttgtggaag gtatgtcagg tgggacttgg      660
gttgatgttg tcttggaaca tggaggttgt gtcactgtaa tggcacagga caaaccgact      720
gtcgacatag agctggttac aacaacagtc agcaacatgg cggaggtaag atcctactgc      780
tatgaggcat caatatcaga catggcttcg gacagccgct gcccaacaca aggtgaagcc      840
taccttgaca agcaatcaga cactcaatat gtctgcaaaa gaacgttagt ggacagaggc      900
tggggaaatg gatgtggact ttttggcaaa gggagcctgg tgacatgcgc taagtttgca      960
tgctccaaga aaatgaccgg gaagagcatc cagccagaga atctggagta ccggataatg     1020
ctgtcagttc atggctccca gcacagtggg atgatcgtta atgacacagg acatgaaact     1080
gatgagaata gagcgaaagt tgagataacg cccaattcac caagagccga agccaccctg     1140
ggggggtttg gaagcctagg acttgattgt gaaccgagga caggccttga cttttcagat     1200
ttgtattact tgactatgaa taacaagcac tggctggttc acaaggagtg gttccacgac     1260
attccattac cttggcacgc tggggcagac accggaactc cacactggaa caacaaagaa     1320
gcactggtag agttcaagga cgcacatgcc aaaaggcaaa ctgtcgtggt tctagggagt     1380
caagaaggag cagttcacac ggcccttgct ggagctctgg aggctgagat ggatggtgca     1440
aagggaaggc tgtcctctgg ccacttgaaa tgtcgcctga aatggataaa cttagattg      1500 aagggcgtgt catactcctt gtgtactgca gcgttcacat tcaccaagat cccggctgaa     1560
acactgcacg ggacagtcac agtggaggta cagtacgcag ggacagatgg accttgcaag     1620
gttccagctc agatggcggt ggacatgcaa actctgaccc cagttgggag gttgataacc     1680
gctaaccccg taatcactga aagcactgag aactctaaga tgatgctgga acttgatcca     1740
ccatttgggg actcttacat tgtcatagga gtcggggaga agaagatcac ccaccactgg     1800
cacaggagtg gcagcaccat tggaaaagca tttgaagcca ctgtgagagg tgccaagaga     1860
atggcagtct gggagacac agcctgggac tttggatcag ttggaggcgc tctcaactca      1920
ttgggcaagg gcatccatca aatctttgga gcagctttca atcattgtt tggaggaatg      1980 tcctggttct cacaaattct cattggaacg ttgctgatgt ggttgggtct gaacgcaaag     2040
aatggatcta tttcccttat gtgcttggcc ttaggggag tgttgatctt cttatccaca      2100
gccgtctctg cttaa                                                      2115
```

<210> SEQ ID NO 6
<211> LENGTH: 2115
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 6

```
atgctgagga tcatcaatgc ccgcaaggag aagaagcgga gaggagccga cacaagcgtg       60
ggcatcgtgg gcctgctgct gaccacagca atggccgccg aggtgaccag gaggggcagc      120
```

```
gcctactata tgtacctgga ccggaatgat gccggcgagg ccatctcctt tcccaccaca    180
ctgggcatga acaagtgcta catccagatc atggacctgg ccacacatg cgatgccacc     240 atgtcctatg agtgtccaat gctggacgag ggcgtggagc ccgacgatgt ggattgctgg    300
tgtaacacca catctacatg ggtggtgtac ggcacctgtc accacaagaa gggagaggcc    360
cggcggagcc ggcgggccgt gacactgcct tcccactcta cccggaagct gcagacaaga    420
agccagacct ggctggagtc ccgggagtat accaagcacc tgatccgggt ggagaactgg    480
atctttagaa atccaggatt cgccctggcc gccgccgcca tcgcatggct gctgggcagc    540
tccaccagcc agaaagtgat ctacctggtc atgatcctgc tgatcgcccc tgcctattct    600
atcaggtgca tcggcgtgag caaccgggac ttcgtggagg aatgtccgg aggcacctgg    660 gtggatgtgg tgctggagca cggcggctgc gtgacagtga tggcccagga caagccaacc    720
gtggacatcg agctggtgac cacaaccgtg tccaacatgg ccgaggtgcg gtcttactgc    780
tatgaggcca gcatctccga catggcctct gatagcagat gtcccaccca gggcgaggcc    840
tacctggaca agcagtccga tacacagtac gtgtgcaaga ggaccctggt ggacagggga    900
tggggaaatg gatgtggcct gtttggcaag ggctctctgg tgacatgcgc caagttcgcc    960
tgtagcaaga agatgaccgg caagtccatc agccagagaa cctggagta caggatcatg   1020 ctgtctgtgc acggctccca gcactctggc atgatcgtga acgacacagg ccacgagaca   1080
gatgagaata gggccaaggt ggagatcaca cctaactccc cacgcgccga ggccaccctg   1140
ggcggatttg gctctctggg cctggactgc gagcctcgca caggcctgga cttctccgat   1200
ctgtactatc tgaccatgaa caataagcac tggctggtgc acaaggagtg gtttcacgac   1260
atcccactgc catggcacgc aggagccgat acaggcaccc cacactggaa caataaggag   1320
gccctggtgg agttcaagga tgcccacgcc aagaggcaga cagtggtggt gctgggcagc   1380
caggagggag ccgtgcacac cgccctggcc ggggccctgg aggcagagat ggacggagcc   1440
aagggccgcc tgtctagcgg acacctgaag tgccggctga gatggatgaa gctgagactg   1500
aagggcgtgt cctactctct gtgcaccgcc gccttcacct tcaccaagat ccccgccgag   1560
acactgcacg gcacagtgac cgtggaggtg cagtatgccg gcacagacgg cccctgtaag   1620
gtgcctgccc agatggccgt ggatatgcag acactgaccc ctgtgggccg gctgatcacc   1680
gcaaatccag tgatcacaga gtctaccgag aacagcaaga tgatgctgga gctggacccc   1740
ccttttggcg atagctatat cgtgatcggc gtgggcgaga gaagatcac acaccactgg   1800 cacagaagcg gctccacaat cggcaaggcc tttgaggcaa ccgtgcgggg agccaagaga   1860
atggccgtgc tgggcgacac cgcatgggat ttcggctctg tgggagggc actgaacagc   1920 ctggggaagg gcatccacca gatcttcgga gccgccttta gtccctgtt cggcggcatg   1980 agctggtttt cccagatcct gatcggcacc ctgctgatgt ggctgggcct gaacgccaag   2040
aatggctcta tcagcctgat gtgcctggcc ctgggcggcg tgctgatctt cctgtccacc   2100
gccgtgtctg cctga                                                    2115
```

<210> SEQ ID NO 7
<211> LENGTH: 704
<212> TYPE: PRT
<213> ORGANISM: Zika virus

<400> SEQUENCE: 7

Met Leu Arg Ile Ile Asn Ala Arg Lys Glu Lys Lys Arg Arg Gly Ala
1               5                   10                  15

-continued

Asp Thr Ser Val Gly Ile Val Gly Leu Leu Thr Thr Ala Met Ala
            20                  25                  30

Ala Glu Val Thr Arg Arg Gly Ser Ala Tyr Tyr Met Tyr Leu Asp Arg
            35                  40                  45

Asn Asp Ala Gly Glu Ala Ile Ser Phe Pro Thr Thr Leu Gly Met Asn
50                      55                  60

Lys Cys Tyr Ile Gln Ile Met Asp Leu Gly His Thr Cys Asp Ala Thr
65                  70                  75                  80

Met Ser Tyr Glu Cys Pro Met Leu Asp Glu Gly Val Glu Pro Asp Asp
                85                  90                  95

Val Asp Cys Trp Cys Asn Thr Thr Ser Thr Trp Val Val Tyr Gly Thr
            100                 105                 110

Cys His His Lys Lys Gly Glu Ala Arg Arg Ser Arg Lys Ala Val Thr
        115                 120                 125

Leu Pro Ser His Ser Thr Arg Lys Leu Gln Thr Arg Ser Gln Thr Trp
        130                 135                 140

Leu Glu Ser Arg Glu Tyr Thr Lys His Leu Ile Arg Val Glu Asn Trp
145                 150                 155                 160

Ile Phe Arg Asn Pro Gly Phe Ala Leu Ala Ala Ala Ile Ala Trp
                165                 170                 175

Leu Leu Gly Ser Ser Thr Ser Gln Lys Val Ile Tyr Leu Val Met Ile
            180                 185                 190

Leu Leu Ile Ala Pro Ala Tyr Ser Ile Arg Cys Ile Gly Val Ser Asn
        195                 200                 205

Arg Asp Phe Val Glu Gly Met Ser Gly Gly Thr Trp Val Asp Val Val
210                 215                 220

Leu Glu His Gly Gly Cys Val Thr Val Met Ala Gln Asp Lys Pro Thr
225                 230                 235                 240

Val Asp Ile Glu Leu Val Thr Thr Thr Val Ser Asn Met Ala Glu Val
                245                 250                 255

Arg Ser Tyr Cys Tyr Glu Ala Ser Ile Ser Asp Met Ala Ser Asp Ser
            260                 265                 270

Arg Cys Pro Thr Gln Gly Glu Ala Tyr Leu Asp Lys Gln Ser Asp Thr
275                 280                 285

Gln Tyr Val Cys Lys Arg Thr Leu Val Asp Arg Gly Trp Gly Asn Gly
290                 295                 300

Cys Gly Leu Phe Gly Lys Gly Ser Leu Val Thr Cys Ala Lys Phe Ala
305                 310                 315                 320

Cys Ser Lys Lys Met Thr Gly Lys Ser Ile Gln Pro Glu Asn Leu Glu
                325                 330                 335

Tyr Arg Ile Met Leu Ser Val His Gly Ser Gln His Ser Gly Met Ile
            340                 345                 350

Val Asn Asp Thr Gly His Glu Thr Asp Glu Asn Arg Ala Lys Val Glu
        355                 360                 365

Ile Thr Pro Asn Ser Pro Arg Ala Glu Ala Thr Leu Gly Gly Phe Gly
        370                 375                 380

Ser Leu Gly Leu Asp Cys Glu Pro Arg Thr Gly Leu Asp Phe Ser Asp
385                 390                 395                 400

Leu Tyr Tyr Leu Thr Met Asn Asn Lys His Trp Leu Val His Lys Glu
                405                 410                 415

Trp Phe His Asp Ile Pro Leu Pro Trp His Ala Gly Ala Asp Thr Gly
            420                 425                 430

Thr Pro His Trp Asn Asn Lys Glu Ala Leu Val Glu Phe Lys Asp Ala

|     |     |     |     |     | 435 |     |     |     | 440 |     |     |     |     | 445 |     |     |     |
| --- | --- | --- | --- | --- | --- | --- | --- | --- | --- | --- | --- | --- | --- | --- | --- | --- | --- |

His Ala Lys Arg Gln Thr Val Val Leu Gly Ser Gln Glu Gly Ala
    450                           455                   460

Val His Thr Ala Leu Ala Gly Ala Leu Glu Ala Glu Met Asp Gly Ala
465                  470                   475                  480

Lys Gly Arg Leu Ser Ser Gly His Leu Lys Cys Arg Leu Lys Met Asp
                  485                   490                  495

Lys Leu Arg Leu Lys Gly Val Ser Tyr Ser Leu Cys Thr Ala Ala Phe
        500                   505                510

Thr Phe Thr Lys Ile Pro Ala Glu Thr Leu His Gly Thr Val Thr Val
       515                 520               525

Glu Val Gln Tyr Ala Gly Thr Asp Gly Pro Cys Lys Val Pro Ala Gln
     530                   535               540

Met Ala Val Asp Met Gln Thr Leu Thr Pro Val Gly Arg Leu Ile Thr
545                  550                   555                  560

Ala Asn Pro Val Ile Thr Glu Ser Thr Glu Asn Ser Lys Met Met Leu
                  565                   570                  575

Glu Leu Asp Pro Pro Phe Gly Asp Ser Tyr Ile Val Ile Gly Val Gly
        580                   585                590

Glu Lys Lys Ile Thr His His Trp His Arg Ser Gly Ser Thr Ile Gly
     595                   600               605

Lys Ala Phe Glu Ala Thr Val Arg Gly Ala Lys Arg Met Ala Val Leu
610                  615                   620

Gly Asp Thr Ala Trp Asp Phe Gly Ser Val Gly Gly Ala Leu Asn Ser
625                  630                   635                  640

Leu Gly Lys Gly Ile His Gln Ile Phe Gly Ala Ala Phe Lys Ser Leu
                  645                   650                655

Phe Gly Gly Met Ser Trp Phe Ser Gln Ile Leu Ile Gly Thr Leu Leu
        660                   665                670

Met Trp Leu Gly Leu Asn Ala Lys Asn Gly Ser Ile Ser Leu Met Cys
     675                   680               685

Leu Ala Leu Gly Gly Val Leu Ile Phe Leu Ser Thr Ala Val Ser Ala
        690                   695                700

<210> SEQ ID NO 8
<211> LENGTH: 2115
<212> TYPE: DNA
<213> ORGANISM: Zika virus

<400> SEQUENCE: 8

```
atgctgagaa taatcaatgc taggaaggag aagaagagac gaggcgcaga tactagtgtc      60
ggaattgttg cctcctgct gaccacagct atggcagcgg aggtcactag acgtgggagt     120
gcatactata tgtacttgga cagaaacgat gctggggagg ccatatcttt tccaaccaca     180
ttggggatga taagtgtta tatacagatc atggatcttg acacacgtg tgatgccacc      240 atgagctatg aatgcccat gctggatgag ggggtgaac cagatgacgt cgattgttgg     300
tgcaacacga cgtcaacttg ggttgtgtac ggaacctgcc atcacaaaaa aggtgaagca     360
cggagatcta gaaaagctgt gacgctcccc tcccattcca ctaggaagct gcaaacgcgg     420
tcgcaaacct ggttggaatc aagagaatac acaaagcact tgattagagt cgaaaattgg     480
atattcagga accctggctt cgcgttagca gcagctgcca tcgcttggct tttgggaagc     540
tcaacgagcc aaaaagtcat atacttggtc atgatactgc tgattgcccc ggcatacagc     600
atcaggtgca taggagtcag caatagggac tttgtggaag gtatgtcagg tgggacttgg     660
```

```
gttgatgttg tcttggaaca tggaggttgt gtcactgtaa tggcacagga caaaccgact    720
gtcgacatag agctggttac aacaacagtc agcaacatgg cggaggtaag atcctactgc    780
tatgaggcat caatatcaga catggcttcg acagccgct gcccaacaca aggtgaagcc     840
taccttgaca agcaatcaga cactcaatat gtctgcaaaa gaacgttagt ggacagaggc    900
tggggaaatg gatgtggact ttttggcaaa gggagcctgg tgacatgcgc taagtttgca    960
tgctccaaga aaatgaccgg gaagagcatc cagccagaga atctggagta ccggataatg   1020
ctgtcagttc atggctccca gcacagtggg atgatcgtta atgacacagg acatgaaact   1080
gatgagaata gagcgaaagt tgagataacg cccaattcac caagagccga agccaccctg   1140 gggggggtttg aagcctagg acttgattgt gaaccgagga caggccttga cttttcagat    1200
ttgtattact tgactatgaa taacaagcac tggctggttc acaaggagtg gttccacgac   1260
attccattac cttggcacgc tggggcagac accggaactc cacactggaa caacaaagaa   1320
gcactggtag agttcaagga cgcacatgcc aaaaggcaaa ctgtcgtggt tctagggagt   1380
caagaaggag cagttcacac ggcccttgct ggagctctgg aggctgagat ggatggtgca   1440
aagggaaggc tgtcctctgg ccacttgaaa tgtcgcctga aaatggataa acttagattg   1500
aagggcgtgt catactcctt gtgtactgca gcgttcacat tcaccaagat cccggctgaa   1560
acactgcacg ggacagtcac agtggaggta cagtacgcag ggacagatgg accttgcaag   1620
gttccagctc agatggcggt ggacatgcaa actctgaccc cagttgggag gttgataacc   1680
gctaaccccg taatcactga aagcactgag aactctaaga tgatgctgga acttgatcca   1740
ccatttgggg actcttacat tgtcatagga gtcggggaga agaagatcac ccaccactgg   1800
cacaggagtg gcagcaccat tggaaaagca tttgaagcca ctgtgagagg tgccaagaga   1860
atggcagtct gggagacac agcctgggac ttttggatcag ttggaggcgc tctcaactca    1920
ttgggcaagg gcatccatca aatctttgga gcagctttca aatcattgtt tggaggaatg   1980
tcctggttct cacaaattct cattggaacg ttgctgatgt ggttgggtct gaacgcaaag   2040
aatggatcta tttccctat gtgcttggcc ttaggggag tgttgatctt cttatccaca    2100
gccgtctctg cttaa                                                    2115
```

<210> SEQ ID NO 9
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgctgagga tcatcaatgc ccgcaaggag aagaagcgga gaggagccga cacaagcgtg     60
ggcatcgtgg gcctgctgct gaccacagca atggccgccg aggtgaccag gaggggcagc    120
gcctactata tgtacctgga ccggaatgat gccggcgagg ccatctcctt tcccaccaca    180
ctgggcatga acaagtgcta catccagatc atggacctgg ccacacatg cgatgccacc    240 atgtcctatg agtgtccaat gctggacgag ggcgtggagc ccgacgatgt ggattgctgg    300
tgtaacacca catctacatg ggtggtgtac ggcacctgtc accacaagaa gggagaggcc    360
cggcggagcc ggaaagccgt gacactgcct tcccactcta cccggaagct gcagacaaga    420
agccagacct ggctgaagtc ccgggagtat accaagcacc tgatccgggt ggagaactgg    480
atctttagaa atccaggatt cgccctggcc gccgccgcca tcgcatggct gctgggcagc    540
```

```
tccaccagcc agaaagtgat ctacctggtc atgatcctgc tgatcgcccc tgcctattct    600
atcaggtgca tcggcgtgag caaccgggac ttcgtggagg aatgtccgg  aggcacctgg    660
gtggatgtgg tgctggagca cggcggctgc gtgacagtga tggcccagga caagccaacc    720
gtggacatcg agctggtgac cacaaccgtg tccaacatgg ccgaggtgcg gtcttactgc    780
tatgaggcca gcatctccga catggcctct gatagcagat gtcccaccca gggcgaggcc    840
tacctggaca gcagtccga  tacacagtac gtgtgcaaga ggaccctggt ggacagggga    900
tggggaaatg gatgtggcct gtttggcaag ggctctctgg tgacatgcgc caagttcgcc    960
tgtagcaaga gatgaccgg  caagtccatc cagccagaga acctggagta caggatcatg   1020
ctgtctgtgc acggctccca gcactctggc atgatcgtga cgacacagg  ccacgagaca   1080
gatgagaata gggccaaggt ggagatcaca cctaactccc cacgcgccga ggccaccctg   1140
ggcggatttg ctctctgggg cctggactgc gagcctcgca caggcctgga cttctccgat   1200
ctgtactatc tgaccatgaa caataagcac tggctggtgc acaaggagtg gtttcacgac   1260
atcccactgc catggcacgc aggagccgat acaggcaccc cacactggaa caataaggag   1320
gccctggtgg agttcaagga tgcccacgcc aagaggcaga cagtggtggt gctgggcagc   1380
caggagggag ccgtgcacac cgccctggcc ggggccctgg aggcagagat ggacggagcc   1440
aagggccgcc tgtctagcgg acacctgaag tgccggctga agatggataa gctgagactg   1500
aagggcgtgt cctactctct gtgcaccgcc gccttcacct tcaccaagat ccccgccgag   1560
acactgcacg gcacagtgac cgtggaggtg cagtatgccg gcacagacgg ccctgtaag   1620
gtgcctgccc agatggccgt ggatatgcag acactgaccc ctgtgggccg gctgatcacc   1680
gcaaatccag tgatcacaga gtctaccgag aacagcaaga tgatgctgga gctggacccc   1740
cctttggcg  atagctatat cgtgatcggc gtgggcgaga agaagatcac acaccactgg   1800
cacagaagcg gctccacaat cggcaaggcc tttgaggcaa ccgtgcgggg agccaagaga   1860
atggccgtgc tgggcgacac cgcatgggat ttcggctctg tgggaggggc actgaacagc   1920
ctggggaagg gcatccacca gatcttcgga gccgccttta gtccctgtt  cggcggcatg   1980
agctggtttt cccagatcct gatcggcacc ctgctgatgt ggctgggcct gaacgccaag   2040
aatggctcta tcagcctgat gtgcctggcc ctgggcggcg tgctgatctt cctgtccacc   2100
gccgtgtctg cctga                                                    2115
```

<210> SEQ ID NO 10
<211> LENGTH: 531
<212> TYPE: PRT
<213> ORGANISM: Zika virus

<400> SEQUENCE: 10

```
Met Leu Arg Ile Ile Asn Ala Arg Lys Glu Lys Lys Arg Gly Ala
1               5                   10                  15

Asp Thr Ser Val Gly Ile Val Gly Leu Leu Leu Thr Thr Ala Met Ala
            20                  25                  30

Ile Arg Cys Ile Gly Val Ser Asn Arg Asp Phe Val Glu Gly Met Ser
        35                  40                  45

Gly Gly Thr Trp Val Asp Val Val Leu Glu His Gly Gly Cys Val Thr
    50                  55                  60

Val Met Ala Gln Asp Lys Pro Thr Val Asp Ile Glu Leu Val Thr Thr
65                  70                  75                  80

Thr Val Ser Asn Met Ala Glu Val Arg Ser Tyr Cys Tyr Glu Ala Ser
```

```
                    85                  90                  95
Ile Ser Asp Met Ala Ser Asp Ser Arg Cys Pro Thr Gln Gly Glu Ala
            100                 105                 110
Tyr Leu Asp Lys Gln Ser Asp Thr Gln Tyr Val Cys Lys Arg Thr Leu
            115                 120                 125
Val Asp Arg Gly Trp Gly Asn Gly Cys Gly Leu Phe Gly Lys Gly Ser
    130                 135                 140
Leu Val Thr Cys Ala Lys Phe Ala Cys Ser Lys Lys Met Thr Gly Lys
145                 150                 155                 160
Ser Ile Gln Pro Glu Asn Leu Glu Tyr Arg Ile Met Leu Ser Val His
                165                 170                 175
Gly Ser Gln His Ser Gly Met Ile Val Asn Asp Thr Gly His Glu Thr
            180                 185                 190
Asp Glu Asn Arg Ala Lys Val Glu Ile Thr Pro Asn Ser Pro Arg Ala
            195                 200                 205
Glu Ala Thr Leu Gly Gly Phe Gly Ser Leu Gly Leu Asp Cys Glu Pro
    210                 215                 220
Arg Thr Gly Leu Asp Phe Ser Asp Leu Tyr Tyr Leu Thr Met Asn Asn
225                 230                 235                 240
Lys His Trp Leu Val His Lys Glu Trp Phe His Asp Ile Pro Leu Pro
                245                 250                 255
Trp His Ala Gly Ala Asp Thr Gly Thr Pro His Trp Asn Asn Lys Glu
            260                 265                 270
Ala Leu Val Glu Phe Lys Asp Ala His Ala Lys Arg Gln Thr Val Val
            275                 280                 285
Val Leu Gly Ser Gln Glu Gly Ala Val His Thr Ala Leu Ala Gly Ala
    290                 295                 300
Leu Glu Ala Glu Met Asp Gly Ala Lys Gly Arg Leu Ser Ser Gly His
305                 310                 315                 320
Leu Lys Cys Arg Leu Lys Met Asp Lys Leu Arg Leu Lys Gly Val Ser
                325                 330                 335
Tyr Ser Leu Cys Thr Ala Ala Phe Thr Phe Thr Lys Ile Pro Ala Glu
            340                 345                 350
Thr Leu His Gly Thr Val Thr Val Glu Val Gln Tyr Ala Gly Thr Asp
            355                 360                 365
Gly Pro Cys Lys Val Pro Ala Gln Met Ala Val Asp Met Gln Thr Leu
    370                 375                 380
Thr Pro Val Gly Arg Leu Ile Thr Ala Asn Pro Val Ile Thr Glu Ser
385                 390                 395                 400
Thr Glu Asn Ser Lys Met Met Leu Glu Leu Asp Pro Pro Phe Gly Asp
                405                 410                 415
Ser Tyr Ile Val Ile Gly Val Gly Glu Lys Lys Ile Thr His His Trp
            420                 425                 430
His Arg Ser Gly Ser Thr Ile Gly Lys Ala Phe Glu Ala Thr Val Arg
            435                 440                 445
Gly Ala Lys Arg Met Ala Val Leu Gly Asp Thr Ala Trp Asp Phe Gly
    450                 455                 460
Ser Val Gly Gly Ala Leu Asn Ser Leu Gly Lys Gly Ile His Gln Ile
465                 470                 475                 480
Phe Gly Ala Ala Phe Lys Ser Phe Phe Phe Ile Ile Gly Leu Ile Ile
                485                 490                 495
Gly Leu Phe Leu Val Leu Arg Val Gly Ile His Leu Cys Ile Lys Leu
            500                 505                 510
```

Lys His Thr Lys Lys Arg Gln Ile Tyr Thr Asp Ile Glu Met Asn Arg
        515                 520                 525

Leu Gly Lys
    530

<210> SEQ ID NO 11
<211> LENGTH: 1596
<212> TYPE: DNA
<213> ORGANISM: Zika virus

<400> SEQUENCE: 11

```
atgctgagaa taatcaatgc taggaaggag aagaagagac gaggcgcaga tactagtgtc      60
ggaattgttg gcctcctgct gaccacagct atggcaatca ggtgcatagg agtcagcaat     120
agggactttg tggaaggtat gtcaggtggg acttgggttg atgttgtctt ggaacatgga     180
ggttgtgtca ctgtaatggc acaggacaaa ccgactgtcg acatagagct ggttacaaca     240
acagtcagca acatggcgga ggtaagatcc tactgctatg aggcatcaat atcagacatg     300
gcttcggaca gccgctgccc aacacaaggt gaagcctacc ttgacaagca atcagacact     360
caatatgtct gcaaaagaac gttagtggac agaggctggg gaaatggatg tggacttttt     420
ggcaaaggga gcctggtgac atgcgctaag tttgcatgct ccaagaaaat gaccgggaag     480
agcatccagc cagagaatct ggagtaccgg ataatgctgt cagttcatgg ctcccagcac     540
agtgggatga tcgttaatga cacaggacat gaaactgatg agaatagagc gaaagttgag     600
ataacgccca attccaccaag agccgaagcc accctggggg ggtttggaag cctaggactt     660
gattgtgaac cgaggacagg ccttgacttt tcagatttgt attacttgac tatgaataac     720
aagcactggc tggttcacaa ggagtggttc cacgacattc cattaccttg gcacgctggg     780
gcagacaccg aactccaca ctggaacaac aaagaagcac tggtagagtt caaggacgca     840
catgccaaaa ggcaaactgt cgtggttcta gggagtcaag aaggagcagt tcacacggcc     900
cttgctggag ctctggaggc tgagatggat ggtgcaaagg aaggctgtc ctctggccac     960
ttgaaatgtc gcctgaaaat ggataaactt agattgaagg gcgtgtcata ctccttgtgt    1020
actgcagcgt tcacattcac caagatcccg gctgaaaaca tgcacgggac agtcacagtg    1080
gaggtacagt acgcagggac agatggacct tgcaaggttc agctcagat ggcggtggac    1140
atgcaaactc tgacccccagt tgggaggttg ataaccgcta cccccgtaat cactgaaagc    1200
actgagaact ctaagatgat gctggaactt gatccaccat ttgggactc ttacattgtc    1260
ataggagtcg gggagaagaa gatcaccac cactggcaca ggagtggcag caccattgga    1320
aaagcatttg aagccactgt gagaggtgcc aagagaatgg cagtcttggg agacacagcc    1380
tgggacttg gatcagttgg aggcgctctc aactcattgg gcaagggcat ccatcaaatc    1440
tttggagcag ctttcaaatc ttttttctt atcataggt taatcattgg actattcttg    1500
gttctccgag ttggtatcca tctttgcatt aaattaaagc acaccaagaa aagacagatt    1560
tatacagaca tagagatgaa ccgacttgga aagtaa                              1596
```

<210> SEQ ID NO 12
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgctgcgga tcatcaatgc cagaaaggag aagaagcgga gaggagccga caccagcgtg    60
ggaatcgtgg gcctgctgct gaccacagcc atggccatcc ggtgcatcgg cgtgtctaac   120
agagactttg tggagggaat gagcggaggc acctgggtgg atgtggtgct ggagcacggc   180
ggctgcgtga cagtgatggc ccaggacaag cctaccgtgg acatcgagct ggtgaccaca   240
accgtgtcta atatggccga ggtgcggagc tactgctatg aggcctctat cagcgacatg   300
gcctccgaca gccggtgtcc aacccaggga gaggcatacc tggacaagca gagcgataca   360
cagtacgtgt gcaagaggac cctggtggat cgcggctggg gcaatggctg tggcctgttt   420
ggcaagggct ccctggtgac atgcgccaag ttcgcctgtt ccaagaagat gaccggcaag   480
tctatccagc cagagaacct ggagtacagg atcatgctgt ctgtgcacgg ctcccagcac   540
tctggcatga tcgtgaacga cacaggccac gagacagatg agaataggg caaggtggag    600 atcacaccta actccccacg cgccgaggcc accctgggcg atttggctc tctgggcctg    660 gactgcgagc cagaacagg cctggacttc agcgatctgt actatctgac catgaacaat    720
aagcactggc tggtgcacaa ggagtggttt cacgacatcc cactgccatg gcacgcagga   780
gccgatacag gcacccctca ctggaacaat aaggaggccc tggtggagtt caaggatgcc   840
cacgccaaga ggcagacagt ggtggtgctg ggctcccagg agggagccgt gcacaccgcc   900
ctggccgggg ccctggaggc agagatggac ggagccaagg ccgcctgag ctccggacac   960 ctgaagtgca ggctgaagat ggataagctg cgcctgaagg gcgtgagcta ctccctgtgc  1020
acagccgcct ttacattcac caagatcccc gccgagacac tgcacggcac agtgaccgtg  1080
gaggtgcagt atgcaggcac agacggacca tgcaaggtgc ctgcacagat ggccgtggat  1140
atgcagacac tgaccccagt gggccggctg atcaccgcaa tcccgtgat cacagagagc   1200 accgagaact ccaagatgat gctggagctg gaccccccctt ttggcgattc ctacatcgtg  1260
atcggcgtgg gcgagaagaa gatcacacac cactggcaca gatctggcag cacaatcggc  1320
aaggcctttg aggcaaccgt gaggggagcc aagaggatgg ccgtgctggg cgacaccgca  1380
tgggatttcg gcagcgtggg agggcactg aacagcctgg gaagggcat ccaccagatc    1440 tttggagccg ccttcaagtc tttcttttc atcatcggcc tgatcatcgg cctgttcctg    1500
gtgctgcggg tgggcatcca cctgtgcatc aagctgaagc acacaaagaa gcggcagatc  1560
tataccgaca tcgagatgaa cagactgggc aagtga                            1596
```

<210> SEQ ID NO 13
<211> LENGTH: 704
<212> TYPE: PRT
<213> ORGANISM: Zika virus

<400> SEQUENCE: 13

```
Met Leu Arg Ile Ile Asn Ala Arg Lys Glu Lys Lys Arg Arg Gly Ala
1               5                   10                  15

Asp Thr Ser Val Gly Ile Val Gly Leu Leu Leu Thr Thr Ala Met Ala
            20                  25                  30

Ala Glu Val Thr Arg Arg Gly Ser Ala Tyr Tyr Met Tyr Leu Asp Arg
        35                  40                  45

Asn Asp Ala Gly Glu Ala Ile Ser Phe Pro Thr Thr Leu Gly Met Asn
    50                  55                  60

Lys Cys Tyr Ile Gln Ile Met Asp Leu Gly His Thr Cys Asp Ala Thr
65                  70                  75                  80

Met Ser Tyr Glu Cys Pro Met Leu Asp Glu Gly Val Glu Pro Asp Asp
```

```
            85              90              95
Val Asp Cys Trp Cys Asn Thr Thr Ser Thr Trp Val Val Tyr Gly Thr
            100             105             110

Cys His His Lys Lys Gly Glu Ala Arg Arg Ser Arg Arg Ala Val Thr
            115             120             125

Leu Pro Ser His Ser Thr Arg Lys Leu Gln Thr Arg Ser Gln Thr Trp
            130             135             140

Leu Glu Ser Arg Glu Tyr Thr Lys His Leu Ile Arg Val Glu Asn Trp
145             150             155             160

Ile Phe Arg Asn Pro Gly Phe Ala Leu Ala Ala Ala Ile Ala Trp
            165             170             175

Leu Leu Gly Ser Ser Thr Ser Gln Lys Val Ile Tyr Leu Val Met Ile
            180             185             190

Leu Leu Ile Ala Pro Ala Tyr Ser Ile Arg Cys Ile Gly Val Ser Asn
            195             200             205

Arg Asp Phe Val Glu Gly Met Ser Gly Gly Thr Trp Val Asp Val Val
            210             215             220

Leu Glu His Gly Gly Cys Val Thr Val Met Ala Gln Asp Lys Pro Thr
225             230             235             240

Val Asp Ile Glu Leu Val Thr Thr Thr Val Ser Asn Met Ala Glu Val
            245             250             255

Arg Ser Tyr Cys Tyr Glu Ala Ser Ile Ser Asp Met Ala Ser Asp Ser
            260             265             270

Arg Cys Pro Thr Gln Gly Glu Ala Tyr Leu Asp Lys Gln Ser Asp Thr
            275             280             285

Gln Tyr Val Cys Lys Arg Thr Leu Val Asp Arg Gly Trp Gly Asn Gly
            290             295             300

Cys Gly Leu Phe Gly Lys Gly Ser Leu Val Thr Cys Ala Lys Phe Ala
305             310             315             320

Cys Ser Lys Lys Met Thr Gly Lys Ser Ile Gln Pro Glu Asn Leu Glu
            325             330             335

Tyr Arg Ile Met Leu Ser Val His Gly Ser Gln His Ser Gly Met Ile
            340             345             350

Val Asn Asp Ile Gly His Glu Thr Asp Glu Asn Arg Ala Lys Val Glu
            355             360             365

Ile Thr Pro Asn Ser Pro Arg Ala Glu Ala Thr Leu Gly Gly Phe Gly
            370             375             380

Ser Leu Gly Leu Asp Cys Glu Pro Arg Thr Gly Leu Asp Phe Ser Asp
385             390             395             400

Leu Tyr Tyr Leu Thr Met Asn Asn Lys His Trp Leu Val His Lys Glu
            405             410             415

Trp Phe His Asp Ile Pro Leu Pro Trp His Ala Gly Ala Asp Thr Gly
            420             425             430

Thr Pro His Trp Asn Asn Lys Glu Ala Leu Val Glu Phe Lys Asp Ala
            435             440             445

His Ala Lys Arg Gln Thr Val Val Leu Gly Ser Gln Glu Gly Ala
            450             455             460

Val His Thr Ala Leu Ala Gly Ala Leu Glu Ala Glu Met Asp Gly Ala
465             470             475             480

Lys Gly Arg Leu Ser Ser Gly His Leu Lys Cys Arg Leu Lys Met Asp
            485             490             495

Lys Leu Arg Leu Lys Gly Val Ser Tyr Ser Leu Cys Thr Ala Ala Phe
            500             505             510
```

```
Thr Phe Thr Lys Ile Pro Ala Glu Thr Leu His Gly Thr Val Thr Val
            515                 520                 525

Glu Val Gln Tyr Ala Gly Thr Asp Gly Pro Cys Lys Val Pro Ala Gln
530                 535                 540

Met Ala Val Asp Met Gln Thr Leu Thr Pro Val Gly Arg Leu Ile Thr
545                 550                 555                 560

Ala Asn Pro Val Ile Thr Glu Ser Thr Glu Asn Ser Lys Met Met Leu
                565                 570                 575

Glu Leu Asp Pro Pro Phe Gly Asp Ser Tyr Ile Val Ile Gly Val Gly
            580                 585                 590

Glu Lys Lys Ile Thr His His Trp His Arg Ser Gly Ser Thr Ile Gly
            595                 600                 605

Lys Ala Phe Glu Ala Thr Val Arg Gly Ala Lys Arg Met Ala Val Leu
            610                 615                 620

Gly Asp Thr Ala Trp Asp Phe Gly Ser Val Gly Gly Ala Leu Asn Ser
625                 630                 635                 640

Leu Gly Lys Gly Ile His Gln Ile Phe Gly Ala Ala Phe Lys Ser Leu
                645                 650                 655

Phe Gly Gly Met Ser Trp Phe Ser Gln Ile Leu Ile Gly Thr Leu Leu
            660                 665                 670

Met Trp Leu Gly Leu Asn Ala Lys Asn Gly Ser Ile Ser Leu Met Cys
            675                 680                 685

Leu Ala Leu Gly Gly Val Leu Ile Phe Leu Ser Thr Ala Val Ser Ala
            690                 695                 700

<210> SEQ ID NO 14
<211> LENGTH: 2115
<212> TYPE: DNA
<213> ORGANISM: Zika virus

<400> SEQUENCE: 14
atgctgagaa taatcaatgc taggaaggag aagaagagac gaggcgcaga tactagtgtc      60
ggaattgttg gcctcctgct gaccacagct atggcagcgg aggtcactag acgtgggagt     120
gcatactata tgtacttgga cagaaacgat gctggggagg ccatatcttt tccaaccaca     180
ttggggatga taagtgttta tacagatctc atggatcttg acacacgtgt tgatgccacc     240
atgagctatg aatgccctat gctggatgag ggggtggaac cagatgacgt cgattgttgg     300
tgcaacacga cgtcaacttg ggttgtgtac ggaacctgcc atcacaaaaa aggtgaagca     360
cggagatcta gaagagctgt gacgctcccc tcccattcca ctaggaagct gcaaacgcgg     420
tcgcaaacct ggttggaatc aagagaatac acaaagcact tgattagagt cgaaaattgg     480
atattcagga accctggctt cgcgttagca gcagctgcca tcgcttggct tttgggaagc     540
tcaacgagcc aaaaagtcat atacttggtc atgatactgc tgattgcccc ggcatacagc     600
atcaggtgca taggagtcag caatagggac tttgtggaag gtatgtcagg tgggacttgg     660
gttgatgttg tcttggaaca tggaggttgt gtcactgtaa tggcacagga caaaccgact     720
gtcgacatag agctggttac aacaacagtc agcaacatgg cggaggtaag atcctactgc     780
tatgaggcat caatatcaga catggcttcg gacagccgct gcccaacaca aggtgaagcc     840
taccttgaca agcaatcaga cactcaatat gtctgcaaaa gaacgttagt ggacagaggc     900
tggggaaatg gatgtggact ttttggcaaa gggagcctgg tgacatgcgc taagtttgca     960
tgctccaaga aaatgaccgg gaagagcatc cagccagaga atctggagta ccggataatg    1020
```

```
ctgtcagttc atggctccca gcacagtggg atgatcgtta atgacattgg acatgaaact      1080
gatgagaata gagcgaaagt tgagataacg cccaattcac caagagccga agccaccctg      1140 gggggggtttg aagcctagg acttgattgt gaaccgagga caggccttga cttttcagat      1200
ttgtattact tgactatgaa taacaagcac tggctggttc acaaggagtg gttccacgac      1260
attccattac cttggcacgc tggggcagac accggaactc cacactggaa caacaaagaa      1320
gcactggtag agttcaagga cgcacatgcc aaaaggcaaa ctgtcgtggt tctagggagt      1380
caagaaggag cagttcacac ggcccttgct ggagctctgg aggctgagat ggatggtgca      1440
aagggaaggc tgtcctctgg ccacttgaaa tgtcgcctga aatggataa acttagattg       1500 aagggcgtgt catactcctt gtgtactgca gcgttcacat tcaccaagat cccggctgaa      1560
acactgcacg ggacagtcac agtggaggta cagtacgcag ggacagatgg accttgcaag      1620
gttccagctc agatggcggt ggacatgcaa actctgaccc cagttgggag gttgataacc      1680
gctaaccccg taatcactga aagcactgag aactctaaga tgatgctgga acttgatcca      1740
ccatttgggg actcttacat tgtcatagga gtcggggaga agaagatcac ccaccactgg      1800
cacaggagtg gcagcaccat tggaaaagca tttgaagcca ctgtgagagg tgccaagaga      1860
atggcagtct gggagacac agcctggac tttggatcag ttggaggcgc tctcaactca       1920
ttgggcaagg gcatccatca aatctttgga gcagctttca aatcattgtt tggaggaatg      1980
tcctggttct cacaaattct cattggaacg ttgctgatgt ggttgggtct gaacgcaaag      2040
aatggatcta tttcccttat gtgcttggcc ttagggggag tgttgatctt cttatccaca      2100
gccgtctctg cttaa                                                      2115

```

<210> SEQ ID NO 15
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgctgagga tcatcaatgc ccgcaaggag aagaagcgga gaggagccga cacaagcgtg        60
ggcatcgtgg gcctgctgct gaccacagca atggccgccg aggtgaccag gaggggcagc       120
gcctactata tgtacctgga ccggaatgat gccggcgagg ccatctcctt tcccaccaca       180
ctgggcatga acaagtgcta catccagatc atggacctgg ccacacatg cgatgccacc       240 atgtcctatg agtgtccaat gctggacgag ggcgtggagc ccgacgatgt ggattgctgg       300
tgtaacacca catctacatg ggtggtgtac ggcacctgtc accacaagaa gggagaggcc       360
cggcggagcc ggcgggccgt gacactgcct tcccactcta cccggaagct gcagacaaga       420
agccagacct ggctggagtc ccgggagtat accaagcacc tgatccgggt ggagaactgg       480
atctttagaa atccaggatt cgccctggcc gccgccgcca tcgcatggct gctgggcagc       540
tccaccagcc agaaagtgat ctacctggtc atgatcctgc tgatcgcccc tgcctattct       600
atcaggtgca tcggcgtgag caaccggac ttcgtggagg aatgtccgg aggcacctgg         660 gtggatgtgg tgctggagca cggcggctgc gtgacagtga tggcccagga caagccaacc       720
gtggacatcg agctggtgac cacaaccgtg tccaacatgg ccgaggtgcg gtcttactgc       780
tatgaggcca gcatctccga catggcctct gatagcagat gtcccaccca gggcgaggcc       840
tacctggaca gcagtccga tacacagtac gtgtgcaaga ggaccctggt ggacaggga         900
```

```
tggggaaatg gatgtggcct gtttggcaag ggctctctgg tgacatgcgc caagttcgcc    960
tgtagcaaga agatgaccgg caagtccatc cagccagaga acctggagta caggatcatg   1020
ctgtctgtgc acggctccca gcactctggc atgatcgtga acgacattgg ccacgagaca   1080
gatgagaata gggccaaggt ggagatcaca cctaactccc cacgcgccga ggccaccctg   1140
ggcggatttg gctctctggg cctggactgc gagcctcgca caggcctgga cttctccgat   1200
ctgtactatc tgaccatgaa caataagcac tggctggtgc acaaggagtg gtttcacgac   1260
atcccactgc catggcacgc aggagccgat acaggcaccc cacactggaa caataaggag   1320
gccctggtgg agttcaagga tgcccacgcc aagaggcaga cagtggtggt gctgggcagc   1380
caggagggag ccgtgcacac cgccctggcc ggggccctgg aggcagagat ggacggagcc   1440
aagggccgcc tgtctagcgg acacctgaag tgccggctga agatggataa gctgagactg   1500
aagggcgtgt cctactctct gtgcaccgcc gccttcacct tcaccaagat ccccgccgag   1560
acactgcacg gcacagtgac cgtggaggtg cagtatgccg gcacagacgg ccctgtaag   1620 gtgcctgccc agatggccgt ggatatgcag acactgaccc ctgtgggccg gctgatcacc   1680
gcaaatccag tgatcacaga gtctaccgag aacagcaaga tgatgctgga gctggacccc   1740 cctttttggcg atagctatat cgtgatcggc gtgggcgaga agaagatcac acaccactgg   1800
cacagaagcg gctccacaat cggcaaggcc tttgaggcaa ccgtgcgggg agccaagaga   1860
atggccgtgc tgggcgacac cgcatgggat ttcggctctg tggagggggc actgaacagc   1920
ctggggaagg gcatccacca gatcttcgga gccgccttta gtccctgtt cggcggcatg   1980 agctggtttt cccagatcct gatcggcacc ctgctgatgt ggctgggcct gaacgccaag   2040
aatggctcta tcagcctgat gtgcctggcc ctgggcggcg tgctgatctt cctgtccacc   2100
gccgtgtctg cctga                                                    2115
```

<210> SEQ ID NO 16
<211> LENGTH: 891
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140
```

```
Gln Val Leu Ser Asp Ser Gly Gly Pro Leu Ile Asp Leu Leu Thr Glu
145                 150                 155                 160

Asp Pro Pro Tyr Arg Asp Pro Arg Pro Pro Ser Asp Arg Asp
            165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
            195                 200                 205

Ser Thr Thr Ser Gln Ala Phe Pro Leu Arg Ala Gly Gly Asn Gly Gln
        210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
            245                 250                 255

Glu Ser Val Leu Ile Thr His Gln Pro Thr Trp Asp Asp Cys Gln Gln
            260                 265                 270

Leu Leu Gly Thr Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
        290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
            325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
            355                 360                 365

Leu Glu Arg Leu Lys Glu Ala Tyr Arg Arg Tyr Thr Pro Tyr Asp Pro
        370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
            405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Glu Arg Ile Arg Arg Glu Thr
        435                 440                 445

Glu Glu Lys Glu Glu Arg Arg Arg Thr Glu Asp Glu Gln Lys Glu Lys
        450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
            485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp Val Gly Cys Ser Val Asp
            530                 535                 540

Phe Ser Lys Lys Glu Thr Arg Cys Gly Thr Gly Val Phe Val Tyr Asn
545                 550                 555                 560
```

```
Asp Val Glu Ala Trp Arg Asp Arg Tyr Lys Tyr His Pro Asp Ser Pro
                565                 570                 575

Arg Arg Leu Ala Ala Val Lys Gln Ala Trp Glu Asp Gly Ile Cys
            580                 585                 590

Gly Ile Ser Ser Val Ser Arg Met Glu Asn Ile Met Trp Arg Ser Val
            595                 600                 605

Glu Gly Glu Leu Asn Ala Ile Leu Glu Glu Asn Gly Val Gln Leu Thr
            610                 615                 620

Val Val Val Gly Ser Val Lys Asn Pro Met Trp Arg Gly Pro Gln Arg
625                 630                 635                 640

Leu Pro Val Pro Val Asn Glu Leu Pro His Gly Trp Lys Ala Trp Gly
                645                 650                 655

Lys Ser Tyr Phe Val Arg Ala Ala Lys Thr Asn Asn Ser Phe Val Val
                660                 665                 670

Asp Gly Asp Thr Leu Lys Glu Cys Pro Leu Lys His Arg Ala Trp Asn
            675                 680                 685

Ser Phe Leu Val Glu Asp His Gly Phe Gly Val Phe His Thr Ser Val
            690                 695                 700

Trp Leu Lys Val Arg Glu Asp Tyr Ser Leu Glu Cys Asp Pro Ala Val
705                 710                 715                 720

Ile Gly Thr Ala Val Lys Gly Lys Glu Ala Val His Ser Asp Leu Gly
                725                 730                 735

Tyr Trp Ile Glu Ser Glu Lys Asn Asp Thr Trp Arg Leu Lys Arg Ala
            740                 745                 750

His Leu Ile Glu Met Lys Thr Cys Glu Trp Pro Lys Ser His Thr Leu
            755                 760                 765

Trp Thr Asp Gly Ile Glu Glu Ser Asp Leu Ile Ile Pro Lys Ser Leu
770                 775                 780

Ala Gly Pro Leu Ser His His Asn Thr Arg Glu Gly Tyr Arg Thr Gln
785                 790                 795                 800

Met Lys Gly Pro Trp His Ser Glu Glu Leu Glu Ile Arg Phe Glu Glu
                805                 810                 815

Cys Pro Gly Thr Lys Val His Val Glu Glu Thr Cys Gly Thr Arg Gly
            820                 825                 830

Pro Ser Leu Arg Ser Thr Thr Ala Ser Gly Arg Val Ile Glu Glu Trp
            835                 840                 845

Cys Cys Arg Glu Cys Thr Met Pro Pro Leu Ser Phe Arg Ala Lys Asp
            850                 855                 860

Gly Cys Trp Tyr Gly Met Glu Ile Arg Pro Arg Lys Glu Pro Glu Ser
865                 870                 875                 880

Asn Leu Val Arg Ser Met Val Thr Ala Gly Ser
                885                 890

<210> SEQ ID NO 17
<211> LENGTH: 2676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgggacaga ccgtcacaac accccctgagc ctgaccctgg acattggaa agacgtggag      60 aggatcgcac ataaccagag cgtggacgtg aagaaacgga gatgggtcac attctgcagt    120
gctgagtggc caactttaa tgtgggatgg ccccgagacg gcactttcaa cagggatctg    180
```

-continued

```
atcacccagg tgaagatcaa ggtctttagc ccaggacctc acggacatcc agaccaggtg    240
ccttatatcg tcacctggga ggcactggcc ttcgatcccc ctccatgggt gaagccattt    300
gtccacccaa aaccacctcc accactgcct ccaagtgccc cttcactgcc actggaacca    360
ccccggagca caccacccca cagctccctg tatcctgctc tgactccatc tctgggcgca    420
aagccaaaac cacaggtgct gagcgactcc ggaggaccac tgattgacct gctgacagag    480 gacccccac cataccgaga tcctcggcct ccaccaagcg accgcgatgg aaatggagga     540
gaggctactc ctgccggcga agccctgac ccatctccaa tggctagtag gctgcgcggc     600
aggcgcgagc ctccagtggc agatagcacc acatcccagg ccttccctct gagggctggg    660
ggaaatgggc agctccagta ttggccattt tctagttcag acctgtacaa ctggaagaac    720
aataacccct ctttcagtga ggaccccggc aaactgaccg ccctgatcga atccgtgctg    780
attacccatc agcccacatg ggacgattgt cagcagctcc tgggcaccct gctgaccgga    840
gaggaaaagc agcgcgtgct gctggaggct cgcaaagcag tccgagggga cgatggacgg    900
cccacacagc tccctaatga ggtggacgcc gcttttccac tggaaagacc cgactgggat    960
tatactaccc aggcagggag aaaccacctg gtccattaca gcagctcct gctggcaggc    1020 ctgcagaatg ccgggagatc ccccaccaac ctggccaagg tgaaaggcat cacacagggg    1080
cctaatgagt caccaagcgc ctttctggag aggctgaagg aagcttaccg acggtatacc    1140 ccatcgacc ctgaggaccc cggacaggaa acaaacgtct ccatgtcttt catctggcag    1200
tctgccccag acattgggcg gaagctggag agactggaag acctgaagaa caagaccctg    1260
ggcgacctgg tgcgggaggc tgaaaagatc ttcaacaaac gggagacccc cgaggaaaga    1320
gaggaaagga ttagaaggga aactgaggaa aaggaggaac gccgacggac cgaggacgaa    1380
cagaaggaga agaacgaga tcggcggcgg caccgggaga tgtcaaagct gctggccacc    1440
gtggtcagcg gacagaaaca ggacagacag ggaggagagc gacggagaag ccagctcgac    1500
agggatcagt gcgcatactg taaggaaaaa ggccattggg ccaaggattg ccccaaaaag    1560
ccaagaggac caagaggacc aagaccacag acatcactgc tgaccctgga cgacgtgggg    1620
tgctcggtgg acttctcaaa gaaggagacg agatgcggta caggggtgtt cgtctataac    1680
gacgttgaag cctggaggga caggtacaag taccatcctg actcccccg tagattggca    1740 gcagcagtca agcaagcctg ggaagatggt atctgcggga tctcctctgt ttcaagaatg    1800
gaaaacatca tgtggagatc agtagaaggg gagctcaacg caatcctgga agagaatgga    1860
gttcaactga cggtcgttgt gggatctgta aaaaacccca tgtggagagg tccacagaga    1920
ttgcccgtgc ctgtgaacga gctgccccac ggctggaagg cttgggggaa atcgtacttc    1980
gtcagagcag caaagacaaa taacagcttt gtcgtggatg tgacacact gaaggaatgc    2040 ccactcaaac atagagcatg gaacagcttt cttgtggagg atcatgggtt cggggtattt    2100
cacactagtg tctggctcaa ggttagagaa gattattcat tagagtgtga tccagccgtt    2160
attggaacag ctgttaaggg aaaggaggct gtacacagtg atctaggcta ctggattgag    2220
agtgagaaga atgacacatg gaggctgaag agggcccatc tgatcgagat gaaaacatgt    2280
gaatggccaa agtcccacac attgtggaca gatggaatag aagagagtga tctgatcata    2340
cccaagtctt tagctgggcc actcagccat cacaatacca gagagggcta caggacccaa    2400
atgaaagggc catggcacag tgaagagctt gaaattcggt ttgaggaatg cccaggcact    2460
aaggtccacg tggaggaaac atgtggaacg agaggaccat ctctgagatc aaccactgca    2520
```

| | |
|---|---|
| agcggaaggg tgatcgagga atggtgctgc agggagtgca caatgccccc actgtcgttc | 2580 |
| cgggctaaag atggctgttg gtatggaatg gagataaggc ccaggaaaga accagaaagc | 2640 |
| aacttagtaa ggtcaatggt gactgcagga tcataa | 2676 |

<210> SEQ ID NO 18
<211> LENGTH: 2676
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 18

| | |
|---|---|
| atgggacaga ccgtgacaac acccctgagc ctgacactgg acattggaa ggacgtggag | 60 |
| cgcatcgcac ataaccagag cgtggacgtg aagaagcgga gatgggtgac cttctgctcc | 120 |
| gccgagtggc ccaccttcaa cgtgggatgg ccccgggacg gcaccttcaa cagagatctg | 180 |
| atcacacagg tgaagatcaa ggtgttttct ccaggaccac acggacaccc agaccaggtg | 240 |
| ccctatatcg tgacctggga ggccctggcc ttcgatccac ctccatgggt gaagcctttt | 300 |
| gtgcacccaa agccacctcc accactgcct ccaagcgccc cttccctgcc actggagcca | 360 |
| cctcggagca ccccacccag aagctccctg tatcccgccc tgacacctag cctgggggcc | 420 |
| aagcctaagc cacaggtgct gtccgactct ggaggaccac tgatcgacct gctgaccgag | 480 |
| gaccccccac cataccgcga tccccggcct ccaccatccg accgggatgg aaatggagga | 540 |
| gaggcaacac ctgccggcga ggcccccgac cctagcccaa tggcctcccg cctgcggggc | 600 |
| aggcgcgagc ctccagtggc cgattctacc acaagccagg cattccctct gagagcagga | 660 |
| ggaaatggcc agctccagta ttggccatt tctagctccg acctgtacaa ctggaagaac | 720 |
| aataaccta gcttctccga ggaccccggc aagctgaccg ccctgatcga gagcgtgctg | 780 |
| atcacccacc agcccacatg ggacgattgt cagcagctcc tgggcaccct gctgaccgga | 840 |
| gaggagaagc agagggtgct gctggaggca aggaaggccg tgagaggcga cgatggccgc | 900 |
| ccaaccccagc tcccaaatga ggtggatgcc gcctttcctc tggagcggcc agactgggat | 960 |
| tataccacac aggccggcag aaaccacctg gtgcactaca acagctcct gctggccggc | 1020 |
| ctgcagaatg ccggcagaag ccccaccaac ctggccaagg tgaagggcat cacacagggc | 1080 |
| cccaatgagt ctcctagcgc ctttctggag cgcctgaagg aggcctaccg gagatatacc | 1140 |
| ccatacgacc ctgaggaccc cggacaggag acaaacgtgt ccatgtcttt catctggcag | 1200 |
| agcgcccccg acatcggcag gaagctggag cgcctggagg acctgaagaa taagaccctg | 1260 |
| ggcgatctgg tgagggaggc cgagaagatc ttcaacaagc gcgagacacc tgaggagaga | 1320 |
| gaggagcgga tcagacggga gacagaggag aaggaggagc ggagaaggac agaggacgag | 1380 |
| cagaaggaga aggagaggga tcgccggaga caccgcgaga tgagcaagct gctggccacc | 1440 |
| gtggtgtccg acagaagca ggacaggcag ggaggagagc ggcggcggag ccagctcgac | 1500 |
| agagatcagt gcgcctattg taaggagaag ggccactggg ccaaggattg ccccaagaag | 1560 |
| cctcgcggcc cacggggccc cagacctcag acctccctgc tgacactgga cgatgtgggc | 1620 |
| tgctctgtgg acttcagcaa gaaggagaca agatgtggca caggcgtgtt cgtgtacaat | 1680 |
| gacgtggagg cctggagaga taggtacaag tatcacccag actcccccg gcggctggcc | 1740 |
| gccgccgtga agcaggcctg ggaggatggc atctgtggca tctctagcgt gtccaggatg | 1800 |
| gagaacatca tgtggcgctc tgtggagggc gagctgaatg ccatcctgga ggagaacgga | 1860 |

```
gtgcagctca ccgtggtggt gggcagcgtg aagaatccaa tgtggagggg accacagaga    1920
ctgccagtgc ccgtgaacga gctgcctcac ggatggaagg catggggcaa gtcttacttc    1980
gtgcgggccg ccaagaccaa taacagcttt gtggtggacg gcgatacact gaaggagtgc    2040
ccactgaagc acagagcctg gaactccttc ctggtggagg accacggctt cggcgtgttt    2100
cacaccagcg tgtggctgaa ggtgagagag gactattccc tggagtgtga tccagccgtg    2160
atcggcacag ccgtgaaggg caaggaggcc gtgcactctg acctgggcta ctggatcgag    2220
agcgagaaga atgatacctg gaggctgaag cgcgcccacc tgatcgagat gaagacatgc    2280
gagtggccta agtcccacac cctgtgggaca gacggcatcg aggagtctga tctgatcatc    2340
cccaagtccc tggccggccc tctgtctcac cacaacacca gggagggcta tcgcacacag    2400
atgaagggcc cctggcacag cgaggagctg gagatcaggt ttgaggagtg ccctggcacc    2460
aaggtgcatg tggaggagac atgtggcaca aggggcccat ccctgcgctc taccacagcc    2520
agcggcagag tgatcgagga gtggtgctgt agagagtgca caatgccacc tctgagcttc    2580
cgcgcaaagg acggctgttg gtacggcatg gagatccgcc ctagaaaaga gcccgagagc    2640
aatctggtca ggtcaatggt caccgctggg tcctaa                              2676
```

<210> SEQ ID NO 19
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
```

-continued

```
               210                 215                 220
Leu Gln Tyr Trp Pro Phe Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                    245                 250                 255

Glu Ser Val Leu Ile Thr His Gln Pro Thr Trp Asp Asp Cys Gln Gln
                260                 265                 270

Leu Leu Gly Thr Leu Leu Thr Gly Glu Glu Lys Gln Arg Val Leu Leu
                275                 280                 285

Glu Ala Arg Lys Ala Val Arg Gly Asp Asp Gly Arg Pro Thr Gln Leu
            290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
                340                 345                 350

Lys Val Lys Gly Ile Thr Gln Gly Pro Asn Glu Ser Pro Ser Ala Phe
                355                 360                 365

Leu Glu Arg Leu Lys Glu Ala Tyr Arg Arg Tyr Thr Pro Tyr Asp Pro
370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
                420                 425                 430

Lys Arg Glu Thr Pro Glu Glu Arg Glu Arg Ile Arg Arg Glu Thr
            435                 440                 445

Glu Glu Lys Glu Glu Arg Arg Arg Thr Glu Asp Glu Gln Lys Glu Lys
450                 455                 460

Glu Arg Asp Arg Arg His Arg Glu Met Ser Lys Leu Leu Ala Thr
465                 470                 475                 480

Val Val Ser Gly Gln Lys Gln Asp Arg Gln Gly Gly Glu Arg Arg
                485                 490                 495

Ser Gln Leu Asp Arg Asp Gln Cys Ala Tyr Cys Lys Glu Lys Gly His
                500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp Asp Pro Ala Val Ile Gly
            530                 535                 540

Thr Ala Val Lys Gly Lys Glu Ala Val His Ser Asp Leu Gly Tyr Trp
545                 550                 555                 560

Ile Glu Ser Glu Lys Asn Asp Thr Trp Arg Leu Lys Arg Ala His Leu
                565                 570                 575

Ile Glu Met Lys Thr Cys Glu Trp Pro Lys Ser His Thr Leu Trp Thr
                580                 585                 590

Asp Gly Ile Glu Glu Ser Asp Leu Ile Ile Pro Lys Ser Leu Ala Gly
                595                 600                 605

Pro Leu Ser His His Asn Thr Arg Glu Gly Tyr Arg Thr Gln Met Lys
            610                 615                 620

Gly Pro Trp His Ser Glu Glu Leu Glu Ile Arg Phe Glu Glu Cys Pro
625                 630                 635                 640
```

Gly Thr Lys Val His Val Glu Glu Thr Cys Gly Thr Arg Gly Pro Ser
            645                 650                 655

Leu Arg Ser Thr Thr Ala Ser Gly Arg Val Ile Glu Glu Trp Cys Cys
            660                 665                 670

Arg Glu Cys Thr Met Pro Pro Leu Ser Phe Arg Ala Lys Asp Gly Cys
            675                 680                 685

Trp Tyr Gly Met Glu Ile Arg Pro Arg Lys Glu Pro Glu Ser Asn Leu
            690                 695                 700

Val Arg Ser Met Val Thr Ala Gly Ser
705                 710

<210> SEQ ID NO 20
<211> LENGTH: 2142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

| | | | | | |
|---|---|---|---|---|---|
| atgggacaga | ccgtcacaac | acccctgagc | ctgaccctgg | gacattggaa | agacgtggag | 60 |
| aggatcgcac | ataaccagag | cgtggacgtg | aagaaacgga | gatgggtcac | attctgcagt | 120 |
| gctgagtggc | caacttttaa | tgtgggatgg | ccccgagacg | gcactttcaa | cagggatctg | 180 |
| atcacccagg | tgaagatcaa | ggtctttagc | ccaggacctc | acggacatcc | agaccaggtg | 240 |
| ccttatatcg | tcacctggga | ggcactggcc | ttcgatcccc | ctccatgggt | gaagccattt | 300 |
| gtccacccaa | aacacctcc | accactgcct | ccaagtgccc | cttcactgcc | actggaacca | 360 |
| ccccggagca | caccccccg | cagctccctg | tatcctgctc | tgactccatc | tctgggcgca | 420 |
| aagccaaaac | acaggtgct | gagcgactcc | ggaggaccac | tgattgacct | gctgacagag | 480 |
| gaccccccac | cataccgaga | tcctcggcct | ccaccaagcg | accgcgatgg | aaatggagga | 540 |
| gaggctactc | ctgccggcga | agcccctgac | ccatctccaa | tggctagtag | gctgcgcggc | 600 |
| aggcgcgagc | ctccagtggc | agatagcacc | acatcccagg | ccttccctct | gagggctggg | 660 |
| ggaaatgggc | agctccagta | ttggccattt | tctagttcag | acctgtacaa | ctggaagaac | 720 |
| aataacccct | ctttcagtga | ggaccccggc | aaactgaccg | ccctgatcga | atccgtgctg | 780 |
| attacccatc | agcccacatg | ggacgattgt | cagcagctcc | tgggcaccct | gctgaccgga | 840 |
| gaggaaaagc | agcgcgtgct | gctggaggct | cgcaaagcag | tccgagggga | cgatggacgg | 900 |
| cccacacagc | tccctaatga | ggtggacgcc | gcttttccac | tggaaagacc | cgactgggat | 960 |
| tatactaccc | aggcagggag | aaaccacctg | gtccattaca | ggcagctcct | gctggcaggc | 1020 |
| ctgcagaatg | ccgggagatc | ccccaccaac | ctggccaagg | tgaaaggcat | cacacagggg | 1080 |
| cctaatgagt | caccaagcgc | ctttctggag | aggctgaagg | aagcttaccg | acggtatacc | 1140 |
| ccatacgacc | ctgaggaccc | cggacaggaa | acaaacgtct | ccatgtctt | catctggcag | 1200 |
| tctgccccag | acattgggcg | gaagctggag | agactggaag | acctgaagaa | caagaccctg | 1260 |
| ggcgacctgg | tgcgggaggc | tgaaaagatc | ttcaacaaac | gggagacccc | cgaggaaaga | 1320 |
| gaggaaagga | ttagaaggga | aactgaggaa | aggaggaac | gccgacggac | cgaggacgaa | 1380 |
| cagaaggaga | agaacgaga | tcggcggcgg | caccgggaga | tgtcaaagct | gctggccacc | 1440 |
| gtggtcagcg | gacagaaaca | ggacagacag | ggaggagagc | gacggagaag | ccagctcgac | 1500 |
| agggatcagt | gcgcatactg | taaggaaaaa | ggccattggg | ccaaggattg | ccccaaaaag | 1560 |

-continued

```
ccaagaggac caagaggacc aagaccacag acatcactgc tgaccctgga cgacgatcca    1620
gccgttattg aacagctgt taagggaaag gaggctgtac acagtgatct aggctactgg     1680
attgagagtg agaagaatga cacatggagg ctgaagaggg cccatctgat cgagatgaaa    1740
acatgtgaat ggccaaagtc ccacacattg tggacagatg aatagaaga gagtgatctg     1800 atcatacca agtctttagc tgggccactc agccatcaca ataccagaga gggctacagg     1860
acccaaatga aagggccatg gcacagtgaa gagcttgaaa ttcggtttga ggaatgccca    1920
ggcactaagg tccacgtgga ggaaacatgt ggaacgagag gaccatctct gagatcaacc    1980
actgcaagcg aagggtgat cgaggaatgg tgctgcaggg agtgcacaat gcccccactg      2040
tcgttccggg ctaaagatgg ctgttggtat ggaatggaga taaggcccag gaaagaacca    2100
gaaagcaact tagtaaggtc aatggtgact gcaggatcat aa                       2142
```

<210> SEQ ID NO 21
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255
```

```
Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
            275                 280                 285

Glu Ala Arg Lys Ala Val Arg Gly Asp Asp Gly Arg Pro Thr Gln Leu
            290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
            355                 360                 365

Leu Glu Arg Leu Lys Glu Ala Tyr Arg Arg Tyr Thr Pro Tyr Asp Pro
            370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Arg Ile Arg Arg Glu Thr
            435                 440                 445

Glu Glu Lys Glu Glu Arg Arg Arg Thr Glu Asp Glu Gln Lys Glu Lys
450                 455                 460

Glu Arg Asp Arg Arg Arg His Arg Glu Met Ser Lys Leu Leu Ala Thr
465                 470                 475                 480

Val Val Ser Gly Gln Lys Asp Arg Gln Gly Glu Arg Arg
                485                 490                 495

Ser Gln Leu Asp Arg Asp Gln Cys Ala Tyr Cys Lys Glu Lys Gly His
                500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp Pro Ala Val Ile Gly
            530                 535                 540

Thr Ala Val Lys Gly Lys Glu Ala Val His Ser Asp Leu Gly Tyr Trp
545                 550                 555                 560

Ile Glu Ser Glu Lys Asn Asp Thr Trp Arg Leu Lys Arg Ala His Leu
                565                 570                 575

Ile Glu Met Lys Thr Cys Glu Trp Pro Lys Ser His Thr Leu Trp Thr
            580                 585                 590

Asp Gly Ile Glu Val Ser Asp Leu Ile Ile Pro Lys Ser Leu Ala Gly
            595                 600                 605

Pro Leu Ser His His Asp Thr Arg Glu Gly Tyr Arg Thr Gln Met Lys
            610                 615                 620

Gly Pro Trp His Ser Glu Glu Leu Glu Ile Arg Phe Glu Glu Cys Pro
625                 630                 635                 640

Gly Thr Lys Val His Val Glu Glu Thr Cys Gly Thr Arg Gly Pro Ser
                645                 650                 655

Leu Arg Ser Thr Thr Ala Ser Gly Arg Val Ile Glu Glu Trp Cys Cys
            660                 665                 670

Arg Glu Cys Thr Met Pro Ser Leu Ser Phe Arg Ala Lys Asp Gly Cys
```

675                 680                 685
Trp Tyr Gly Val Glu Ile Arg Pro Arg Lys Glu Pro Glu Ser Asn Leu
    690                 695                 700

Val Arg Ser Met Val Thr Ala Gly Ser
705                 710

<210> SEQ ID NO 22
<211> LENGTH: 2142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

| | | | | | |
|---|---|---|---|---|---|
| atgggacaga | ccgtcacaac | acccctgagc | ctgaccctgg | acattggaa | agacgtggag | 60 |
| aggatcgcac | ataaccagag | cgtggacgtg | aagaaacgga | gatgggtcac | attctgcagt | 120 |
| gctgagtggc | caacttttaa | tgtgggatgg | ccccgagacg | gcactttcaa | cagggatctg | 180 |
| atcacccagg | tgaagatcaa | ggtctttagc | ccaggacctc | acggacatcc | agaccaggtg | 240 |
| ccttatatcg | tcacctggga | ggcactggcc | ttcgatcccc | ctccatgggt | gaagccattt | 300 |
| gtccacccaa | aaccacctcc | accactgcct | ccaagtgccc | cttcactgcc | actggaacca | 360 |
| ccccggagca | caccccccg | cagctccctg | tatcctgctc | tgactccatc | tctgggcgca | 420 |
| aagccaaaac | cacaggtgct | gagcgactcc | ggaggaccac | tgattgacct | gctgacagag | 480 |
| gaccccccac | cataccgaga | tcctcggcct | ccaccaagcg | accgcgatgg | aaatggagga | 540 |
| gaggctactc | ctgccggcga | agcccctgac | ccatctccaa | tggctagtag | gctgcgcggc | 600 |
| aggcgcgagc | ctccagtggc | agatagcacc | acatcccagg | ccttccctct | gagggctggg | 660 |
| ggaaatgggc | agctccagta | ttggccattt | tctagttcag | acctgtacaa | ctggaagaac | 720 |
| aataacccct | ctttcagtga | ggaccccggc | aaactgaccg | ccctgatcga | atccgtgctg | 780 |
| attacccatc | agcccacatg | ggacgattgt | cagcagctcc | tgggcaccct | gctgaccgga | 840 |
| gaggaaaagc | agcgcgtgct | gctgaggct | cgcaaagcag | tccgagggga | cgatggacgg | 900 |
| cccacacagc | tccctaatga | ggtggacgcc | gcttttccac | tggaaagacc | cgactgggat | 960 |
| tatactaccc | aggcagggag | aaaccacctg | gtccattaca | ggcagctcct | gctggcaggc | 1020 |
| ctgcagaatg | ccgggagatc | ccccaccaac | ctggccaagg | tgaaaggcat | cacacagggg | 1080 |
| cctaatgagt | caccaagcgc | ctttctggag | aggctgaagg | aagcttaccg | acggtatacc | 1140 |
| ccatacgacc | ctgaggaccc | cggacaggaa | acaaacgtct | ccatgtcttt | catctggcag | 1200 |
| tctgccccag | acattgggcg | gaagctggag | agactggaag | acctgaagaa | caagaccctg | 1260 |
| ggcgacctgg | tgcgggaggc | tgaaaagatc | ttcaacaaac | gggagacccc | cgaggaaaga | 1320 |
| gaggaaagga | ttagaaggga | aactgaggaa | aaggaggaac | gccgacggac | cgaggacgaa | 1380 |
| cagaaggaga | agaacgaga | tcggcggcg | caccgggaga | tgtcaaagct | gctggccacc | 1440 |
| gtggtcagcg | gacagaaaca | ggacagacag | ggaggagagc | gacggagaag | ccagctcgac | 1500 |
| agggatcagt | gcgcatactg | taaggaaaaa | ggccattggg | ccaaggattg | ccccaaaaag | 1560 |
| ccaagaggac | caagaggacc | aagaccacag | acatcactgc | tgaccctgga | cgacgatcca | 1620 |
| gccgttattg | aacagctgt | taagggaaag | gaggctgtac | acagtgatct | aggctactgg | 1680 |
| attgagagtg | agaagaatga | cacatggagg | ctgaagaggg | cccatctgat | cgagatgaaa | 1740 |
| acatgtgaat | ggccaaagtc | ccacacattg | tggacagatg | gaatagaagt | tagtgatctg | 1800 |

| | |
|---|---|
| atcataccca agtctttagc tgggccactc agccatcacg ataccagaga gggctacagg | 1860 |
| acccaaatga aagggccatg gcacagtgaa gagcttgaaa ttcggtttga ggaatgccca | 1920 |
| ggcactaagg tccacgtgga ggaaacatgt ggaacgagag gaccatctct gagatcaacc | 1980 |
| actgcaagcg gaagggtgat cgaggaatgg tgctgcaggg agtgcacaat gccctctctg | 2040 |
| tcgttccggg ctaaagatgg ctgttggtat ggagttgaga taaggcccag gaaagaacca | 2100 |
| gaaagcaact tagtaaggtc aatggtgact gcaggatcat aa | 2142 |

<210> SEQ ID NO 23
<211> LENGTH: 6575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | |
|---|---|
| ctagagagct tggcccattg catacgttgt atccatatca taatatgtac atttatattg | 60 |
| gctcatgtcc aacattaccg ccatgttgac attgattatt gactagttat taatagtaat | 120 |
| caattacggg gtcattagtt catagcccat atatggagtt ccgcgttaca taacttacgg | 180 |
| taaatggccc gcctggctga ccgcccaacg accccgccc attgacgtca ataatgacgt | 240 |
| atgttcccat agtaacgcca atagggactt tccattgacg tcaatgggtg gagtatttac | 300 |
| ggtaaactgc ccacttggca gtacatcaag tgtatcatat gccaagtacg ccccctattg | 360 |
| acgtcaatga cggtaaatgg cccgcctggc attatgccca gtacatgacc ttatgggact | 420 |
| ttcctacttg gcagtacatc tacgtattag tcatcgctat taccatggtg atgcggtttt | 480 |
| ggcagtacat caatgggcgt ggatagcggt ttgactcacg gggatttcca agtctccacc | 540 |
| ccattgacgt caatgggagt ttgttttggc accaaaatca acgggacttt ccaaaatgtc | 600 |
| gtaacaactc cgccccattg acgcaaatgg gcggtaggcg tgtacggtgg gaggtctata | 660 |
| taagcagagc tcgtttagtg aaccgtcaga tcgcctggag acgccatcca cgctgttttg | 720 |
| acctccatag aagacaccgg gaccgatcca gcctccggtc gaccgatcct gagaacttca | 780 |
| gggtgagttt ggggacccct tgattgttct tcttttttcgc tattgtaaaa ttcatgttat | 840 |
| atggaggggg caaagttttc agggtgttgt ttagaatggg aagatgtccc ttgtatcacc | 900 |
| atggacccc atgataattt tgtttctttc actttctact ctgttgacaa ccattgtctc | 960 |
| ctcttatttt cttttcattt tcttgtaact ttttcgttaa actttagctt gcatttgtaa | 1020 |
| cgaattttta aattcacttt tgtttatttg tcagattgta agtactttct ctaatcactt | 1080 |
| ttttttcaag gcaatcaggg tatattatat tgtacttcag cacagtttta gagaacaatt | 1140 |
| gttataatta aatgataagg tagaatattt ctgcatataa attctggctg gcgtggaaat | 1200 |
| attcttattg gtagaaacaa ctacatcctg gtcatcatcc tgcctttctc tttatggtta | 1260 |
| caatgatata cactgtttga gatgaggata aaatactctg agtccaaacc gggcccctct | 1320 |
| gctaaccatg ttcatgcctt cttctttttc ctacagctcc tgggcaacgt gctggttatt | 1380 |
| gtgctgtctc atcatttgg caaagaattc ctcgaggttt aaacgaattc cgccaccatg | 1440 |
| gagttgctaa tcctcaaagc aaatgcaatt accacaatcc tcactgcagt cacattttgt | 1500 |
| tttgcttctg gtcaaaacat cactgaagaa ttttatcaat caacatgcag tgcagttagc | 1560 |
| aaaggctatc ttagtgctct gagaactggt tggtatacca gtgttataac tatagaatta | 1620 |
| agtaatatca aggaaaataa gtgtaatgga acagatgcta aggtaaaatt gataaaacaa | 1680 |

```
gaattagata aatataaaaa tgctgtaaca gaattgcagt tgctcatgca aagcacacca    1740
ccaacaaaca atcgagccag aagagaacta ccaaggttta tgaattatac actcaacaat    1800
gccaaaaaaa ccaatgtaac attaagcaag aaaaggaaaa gaagatttct tggtttttttg   1860 ttaggtgttg gatctgcaat cgccagtggc gttgctgtat ctaaggtcct gcacctagaa    1920
ggggaagtga acaagatcaa aagtgctcta ctatccacaa acaaggctgt agtcagctta    1980
tcaaatggag ttagtgtctt aaccagcaaa gtgttagacc tcaaaaacta tatagataaa    2040
caattgttac ctattgtgaa caagcaaagc tgcagcatat caaatataga aactgtgata    2100
gagttccaac aaaagaacaa cagactacta gagattacca gggaatttag tgttaatgca    2160
ggtgtaacta cacctgtaag cacttacatg ttaactaata gtgaattatt gtcattaatc    2220
aatgatatgc ctataacaaa tgatcagaaa agttaatgt ccaacaatgt tcaaatagtt     2280
agacagcaaa gttactctat catgtccata ataaagagg aagtcttagc atatgtagta     2340
caattaccac tatatggtgt tatagataca ccctgttgga aactacacac atcccctcta    2400
tgtacaacca acacaaaaga agggtccaac atctgtttaa caagaactga cagaggatgg    2460
tactgtgaca atgcaggatc agtatctttc ttcccacaag ctgaaacatg taaagttcaa    2520
tcaaatcgag tattttgtga cacaatgaac agtttaacat taccaagtga aataaatctc    2580
tgcaatgttg acatattcaa ccccaaatat gattgtaaaa ttatgacttc aaaaacagat    2640
gtaagcagct ccgttatcac atctctagga gccattgtgt catgctatgg caaaactaaa    2700
tgtacagcat ccaataaaaa tcgtggaatc ataaagacat tttctaacgg gtgcgattat    2760
gtatcaaata aagggatgga cactgtgtct gtaggtaaca cattatatta tgtaaataag    2820
caagaaggta aaagtctcta tgtaaaaggt gaaccaataa taaatttcta tgacccatta    2880
gtattcccct ctgatgaatt tgatgcatca atatctcaag tcaacgagaa gattaaccag    2940
agcctagcat ttattcgtaa atccgatgaa ttattacata atgtaaatgc tggtaaatcc    3000
accacaaata tcatgataac tactataatt atagtgatta tagtaatatt gttatcatta    3060
attgctgttg gactgctctt atactgtaag gccagaagca caccagtcac actaagcaaa    3120
gatcaactga gtggtataaa taatattgca tttagtaact aagaattcca cgtgggatcc    3180
gtcgaggaat tcactcctca ggtgcaggct gcctatcaga aggtggtggc tggtgtggcc    3240
aatgccctgg ctcacaaata ccactgagat cttttttccct ctgccaaaaa ttatggggac   3300
atcatgaagc cccttgagca tctgacttct ggctaataaa ggaaatttat tttcattgca    3360
atagtgtgtt ggaattttt gtgtctctca ctcggaagga catatgggag ggcaaatcat     3420
ttaaaacatc agaatgagta tttggtttag agtttggcaa catatgccca tatgctggct    3480
gccatgaaca aaggttggct ataaagaggt catcagtata tgaaacagcc ccctgctgtc    3540
cattccttat tccatagaaa agccttgact tgaggttaga ttttttttat attttgtttt    3600
gtgttatttt tttctttaac atccctaaaa ttttccttac atgttttact agccagattt    3660
ttcctcctct cctgactact cccagtcata gctgtccctc ttctcttatg gagatccctc    3720
gacggatcgg ccgcaattcg taatcatgtc atagctgttt cctgtgtgaa attgttatcc    3780
gctcacaatt ccacacaaca tacgagccgg aagcataaag tgtaaagcct ggggtgccta    3840
atgagtgagc taactcacat taattgcgtt gcgctcactg cccgctttcc agtcgggaaa    3900
cctgtcgtgc cagctgcatt aatgaatcgg ccaacgcgcg gggagaggcg gtttgcgtat    3960
tgggcgctct tccgcttcct cgctcactga ctcgctgcgc tcggtcgttc ggctgcggcg    4020
agcggtatca gctcactcaa aggcggtaat acggttatcc acagaatcag gggataacgc    4080
```

```
aggaaagaac atgtgagcaa aaggccagca aaaggccagg aaccgtaaaa aggccgcgtt   4140
gctggcgttt ttccataggc tccgcccccc tgacgagcat cacaaaaatc gacgctcaag   4200
tcagaggtgg cgaaacccga caggactata agataccag gcgtttcccc ctggaagctc    4260
cctcgtgcgc tctcctgttc cgaccctgcc gcttaccgga tacctgtccg cctttctccc   4320
ttcgggaagc gtggcgcttt ctcatagctc acgctgtagg tatctcagtt cggtgtaggt   4380
cgttcgctcc aagctgggct gtgtgcacga accccccgtt cagcccgacc gctgcgcctt   4440
atccggtaac tatcgtcttg agtccaaccc ggtaagacac gacttatcgc cactggcagc   4500
agccactggt aacaggatta gcagagcgag gtatgtaggc ggtgctacag agttcttgaa   4560
gtggtggcct aactacggct acactagaag aacagtattt ggtatctgcg ctctgctgaa   4620
gccagttacc ttcggaaaaa gagttggtag ctcttgatcc ggcaaacaaa ccaccgctgg   4680
tagcggtggt ttttttgttt gcaagcagca gattacgcgc agaaaaaaag gatctcaaga   4740
agatcctttg atcttttcta cggggtctga cgctcagtgg aacgaaaact cacgttaagg   4800
gattttggtc atgagattat caaaaaggat cttcacctag atccttttaa attaaaaatg   4860
aagttttaaa tcaatctaaa gtatatatga gtaaacttgg tctgacagtt accaatgctt   4920
aatcagtgag gcacctatct cagcgatctg tctatttcgt tcatccatag ttgcctgact   4980
ccccgtcgtg tagataacta cgatacggga gggcttacca tctggcccca gtgctgcaat   5040
gataccgcga gacccacgct caccggctcc agatttatca gcaataaacc agccagccgg   5100
aagggccgag cgcagaagtg gtcctgcaac tttatccgcc tccatccagt ctattaattg   5160
ttgccgggaa gctagagtaa gtagttcgcc agttaatagt ttgcgcaacg ttgttgccat   5220
tgctacaggc atcgtggtgt cacgctcgtc gtttggtatg gcttcattca gctccggttc   5280
ccaacgatca aggcgagtta catgatcccc catgttgtgc aaaaaagcgg ttagctcct   5340 tcggtcctcc gatcgttgtc agaagtaagt tggccgcagt gttatcactc atggttatgg   5400
cagcactgca taattctctt actgtcatgc catccgtaag atgcttttct gtgactggtg   5460
agtactcaac caagtcattc tgagaatagt gtatgcggcg accgagttgc tcttgcccgg   5520
cgtcaatacg ggataatacc gcgccacata gcagaacttt aaaagtgctc atcattggaa   5580
aacgttcttc ggggcgaaaa ctctcaagga tcttaccgct gttgagatcc agttcgatgt   5640
aacccactcg tgcacccaac tgatcttcag catcttttac tttcaccagc gtttctgggt   5700
gagcaaaaac aggaaggcaa aatgccgcaa aaagggaat aagggcgaca cggaaatgtt    5760
gaatactcat actcttcctt tttcaatatt attgaagcat ttatcagggt tattgtctca   5820
tgagcggata catatttgaa tgtatttaga aaaataaaca ataggggtt ccgcgcacat    5880 ttccccgaaa agtgccacct aaattgtaag cgttaatatt tgttaaaat tcgcgttaaa    5940 tttttgttaa atcagctcat tttttaacca ataggccgaa atcggcaaaa tcccttataa   6000
atcaaaagaa tagaccgaga tagggttgag tgttgttcca gtttggaaca agagtccact   6060
attaaagaac gtggactcca acgtcaaagg gcgaaaaacc gtctatcagg gcgatggccc   6120
actacgtgaa ccatcaccct aatcaagttt ttggggtcg aggtgccgta aagcactaaa    6180
tcggaaccct aaagggagcc ccgatttag agcttgacgg ggaaagccgg cgaacgtggc   6240
gagaaaggaa gggaagaaag cgaaaggagc gggcgctagg gcgctggcaa gtgtagcggt   6300
cacgctgcgc gtaaccacca cacccgccgc gcttaatgcg ccgctacagg gcgcgtccca   6360
ttcgccattc aggctgcgca actgttggga agggcgatcg gtgcgggcct cttcgctatt   6420
```

-continued

| | |
|---|---|
| acgccagctg gcgaaagggg gatgtgctgc aaggcgatta agttgggtaa cgccagggtt | 6480 |
| ttcccagtca cgacgttgta aaacgacggc cagtgagcgc gcgtaatacg actcactata | 6540 |
| gggcgaattg gagctccacc gcggtggcgg ccgct | 6575 |

<210> SEQ ID NO 24
<211> LENGTH: 6611
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | |
|---|---|
| ctagagagct tggcccattg catacgttgt atccatatca taatatgtac atttatattg | 60 |
| gctcatgtcc aacattaccg ccatgttgac attgattatt gactagttat taatagtaat | 120 |
| caattacggg gtcattagtt catagcccat atatggagtt ccgcgttaca aacttacgg | 180 |
| taaatggccc gcctggctga ccgcccaacg acccccgccc attgacgtca ataatgacgt | 240 |
| atgttcccat agtaacgcca tagggacttt tccattgacg tcaatgggtg gagtatttac | 300 |
| ggtaaactgc ccacttggca gtacatcaag tgtatcatat gccaagtacg ccccctattg | 360 |
| acgtcaatga cggtaaatgg cccgcctggc attatgccca gtacatgacc ttatgggact | 420 |
| ttcctacttg gcagtacatc tacgtattag tcatcgctat taccatggtg atgcggtttt | 480 |
| ggcagtacat caatgggcgt ggatagcggt ttgactcacg gggatttcca agtctccacc | 540 |
| ccattgacgt caatgggagt ttgttttggc accaaaatca acgggacttt ccaaaatgtc | 600 |
| gtaacaactc cgccccattg acgcaaatgg gcggtaggcg tgtacggtgg aggtctata | 660 |
| taagcagagc tcgtttagtg aaccgtcaga tcgcctggag acgccatcca cgctgttttg | 720 |
| acctccatag aagacaccgg gaccgatcca gcctccggtc gaccgatcct gagaacttca | 780 |
| gggtgagttt ggggacccct tgattgttct tcttttttcgc tattgtaaaa ttcatgttat | 840 |
| atggaggggg caaagttttc agggtgttgt ttagaatggg aagatgtccc ttgtatcacc | 900 |
| atggacccct catgataatt tgtttcttt actttctact ctgttgacaa ccattgtctc | 960 |
| ctcttatttt cttttcattt tcttgtaact ttttcgttaa actttagctt gcatttgtaa | 1020 |
| cgaatttta aattcacttt tgtttatttg tcagattgta agtactttct ctaatcactt | 1080 |
| ttttttcaag gcaatcaggg tatattatat tgtacttcag cacagtttta gagaacaatt | 1140 |
| gttataatta aatgataagg tagaatattt ctgcatataa attctggctg gcgtggaaat | 1200 |
| attcttattg gtagaaacaa ctacatcctg gtcatcatcc tgccttttct tttatggtta | 1260 |
| caatgatata cactgtttga gatgaggata aaatactctg agtccaaacc gggccccttct | 1320 |
| gctaaccatg ttcatgcctt cttcttttc ctacagctcc tgggcaacgt gctggttatt | 1380 |
| gtgctgtctc atcattttgg caaagaattc ctcgaggttt aaacgaattc gccaccatg | 1440 |
| gagttgctaa tcctcaaagc aaatgcaatt accacaatcc tcactgcagt cacatttgt | 1500 |
| tttgcttctg gtcaaaacat cactgaagaa ttttatcaat caacatgcag tgcagttagc | 1560 |
| aaaggctatc ttagtgctct gagaactggt tggtatacca gtgttataac tatagaatta | 1620 |
| agtaatatca aggaaaataa gtgtaatgga acagatgcta aggtaaaatt gataaaacaa | 1680 |
| gaattagata atatataaaa tgctgtaaca gaattgcagt tgctcatgca aagcacacca | 1740 |
| ccaacaaaca atcgagccag aagagaacta ccaaggttta tgaattatac actcaacaat | 1800 |
| gccaaaaaaa ccaatgtaac attaagcaag aaaaggaaaa gaagatttct tggttttttg | 1860 |

```
ttaggtgttg gatctgcaat cgccagtggc gttgctgtat ctaaggtcct gcacctagaa    1920
ggggaagtga acaagatcaa aagtgctcta ctatccacaa acaaggctgt agtcagctta    1980
tcaaatggag ttagtgtctt aaccagcaaa gtgttagacc tcaaaaacta tatagataaa    2040
caattgttac ctattgtgaa caagcaaagc tgcagcatat caaatataga aactgtgata    2100
gagttccaac aaaagaacaa cagactacta gagattacca gggaatttag tgttaatgca    2160
ggtgtaacta cacctgtaag cacttacatg ctaactaata gtgaattatt gtcattaatc    2220
aatgatatgc ctataacaaa tgatcagaaa aagttaatgt ccaacaatgt tcaaatagtt    2280
agacagcaaa gttactctat catgtccata ataaaagagg aagtcttagc atatgtagta    2340
caattaccac tatatggtgt tatagataca ccctgttgga aactacacac atcccctcta    2400
tgtacaacca acacaaaaga agggtccaac atctgtttaa caagaactga cagaggatgg    2460
tactgtgaca atgcaggatc agtatctttc ttcccacaag ctgaaacatg taaagttcaa    2520
tcaaatcgag tattttgtga cacaatgaac agtttaacat taccaagtga aataaatctc    2580
tgcaatgttg acatattcaa ccccaaatat gattgtaaaa ttatgacttc aaaaacagat    2640
gtaagcagct ccgttatcac atctctagga gccattgtgt catgctatgg caaaactaaa    2700
tgtacagcat ccaataaaaa tcgtggaatc ataaagacat tttctaacgg gtgcgattat    2760
gtatcaaata aagggatgga cactgtgtct gtaggtaaca cattatatta tgtaaataag    2820
caagaaggta aaagtctcta tgtaaaaggt gaaccaataa taaatttcta tgacccatta    2880
gtattcccct ctgatgaatt tgatgcatca atatctcaag tcaacgagaa gattaaccag    2940
agcctagcat ttattcgtaa atccgatgaa ttattacata tgttaacgc tggtaaaagt    3000 actacaaata tcatgataac tactactcgt tggttcagta gttggaaaag ctctattgcc    3060
tcttttttct ttatcatagg gttaatcatt ggactattct tggttctccg agttggtatc    3120
catctttgca ttaaattaaa gcacaccaag aaaagacaga tttatacaga catagagatg    3180
aaccgacttg gaaagtaaga attcgatatc ggatccgtcg aggaattcac tcctcaggtg    3240
caggctgcct atcagaaggt ggtggctggt gtggccaatg ccctggctca caataccac    3300 tgagatcttt ttccctctgc caaaaattat ggggacatca tgaagcccct tgagcatctg    3360
acttctggct aataaaggaa atttattttc attgcaatag tgtgttggaa ttttttgtgt    3420
ctctcactcg gaaggacata tgggagggca aatcatttaa aacatcagaa tgagtatttg    3480
gtttagagtt tggcaacata tgcccatatg ctggctgcca tgaacaaagg ttggctataa    3540
agaggtcatc agtatatgaa acagccccct gctgtccatt ccttattcca tagaaaagcc    3600
ttgacttgag gttagatttt ttttatattt tgttttgtgt tatttttttc tttaacatcc    3660
ctaaaatttt ccttacatgt tttactagcc agatttttcc tcctctcctg actactccca    3720
gtcatagctg tccctcttct cttatggaga tccctcgacg gatcggccgc aattcgtaat    3780
catgtcatag ctgtttcctg tgtgaaattg ttatccgctc acaattccac acaacatacg    3840
agccggaagc ataaagtgta aagcctgggg tgcctaatga gtgagctaac tcacattaat    3900
tgcgttgcgc tcactgcccg ctttccagtc gggaaacctg tcgtgccagc tgcattaatg    3960
aatcggccaa cgcgcgggga gaggcggttt gcgtattggg cgctcttccg cttcctcgct    4020
cactgactcg ctgcgctcgg tcgttcggct gcggcgagcg gtatcagctc actcaaaggc    4080
ggtaatacgg ttatccacag aatcagggga taacgcagga agaacatgt gagcaaaagg    4140 ccagcaaaag gccaggaacc gtaaaaaggc cgcgttgctg gcgttttcc ataggctccg    4200 ccccccctgac gagcatcaca aaaatcgacg ctcaagtcag aggtggcgaa acccgacagg    4260
```

```
actataaaga taccaggcgt ttcccccctgg aagctccctc gtgcgctctc ctgttccgac   4320
cctgccgctt accggatacc tgtccgcctt tctcccttcg ggaagcgtgg cgctttctca   4380
tagctcacgc tgtaggtatc tcagttcggt gtaggtcgtt cgctccaagc tgggctgtgt   4440
gcacgaaccc cccgttcagc ccgaccgctg cgccttatcc ggtaactatc gtcttgagtc   4500
caacccggta agacacgact tatcgccact ggcagcagcc actggtaaca ggattagcag   4560
agcgaggtat gtaggcggtg ctacagagtt cttgaagtgg tggcctaact acggctacac   4620
tagaagaaca gtatttggta tctgcgctct gctgaagcca gttaccttcg gaaaaagagt   4680
tggtagctct tgatccggca aacaaaccac cgctggtagc ggtggttttt ttgtttgcaa   4740
gcagcagatt acgcgcagaa aaaaggatc tcaagaagat cctttgatct tttctacggg   4800
gtctgacgct cagtggaacg aaaactcacg ttaagggatt ttggtcatga gattatcaaa   4860
aaggatcttc acctagatcc ttttaaatta aaaatgaagt tttaaatcaa tctaaagtat   4920
atatgagtaa acttggtctg acagttacca atgcttaatc agtgaggcac ctatctcagc   4980
gatctgtcta tttcgttcat ccatagttgc ctgactcccc gtcgtgtaga taactacgat   5040
acgggagggc ttaccatctg gccccagtgc tgcaatgata ccgcgagacc cacgctcacc   5100
ggctccagat ttatcagcaa taaaccagcc agccggaagg gccgagcgca gaagtggtcc   5160
tgcaacttta tccgcctcca tccagtctat taattgttgc cgggaagcta gagtaagtag   5220
ttcgccagtt aatagtttgc gcaacgttgt tgccattgct acaggcatcg tggtgtcacg   5280
ctcgtcgttt ggtatggctt cattcagctc cggttcccaa cgatcaaggc gagttacatg   5340
atcccccatg ttgtgcaaaa aagcgggtta gctccttcgg tcctccgatc gttgtcagaa   5400
gtaagttggc cgcagtgtta tcactcatgg ttatggcagc actgcataat tctcttactg   5460
tcatgccatc cgtaagatgc ttttctgtga ctggtgagta ctcaaccaag tcattctgag   5520
aatagtgtat gcggcgaccg agttgctctt gcccggcgtc aatacgggat aataccgcgc   5580
cacatagcag aactttaaaa gtgctcatca ttggaaaacg ttcttcgggg cgaaaactct   5640
caaggatctt accgctgttg agatccagtt cgatgtaacc cactcgtgca cccaactgat   5700
cttcagcatc ttttactttc accagcgttt ctgggtgagc aaaaacagga aggcaaaatg   5760
ccgcaaaaaa gggaataagg gcgacacgga aatgttgaat actcatactc ttcctttttc   5820
aatattattg aagcatttat cagggttatt gtctcatgag cggatacata tttgaatgta   5880
tttagaaaaa taaacaaata ggggttccgc gcacatttcc ccgaaaagtg ccacctaaat   5940
tgtaagcgtt aatattttgt taaaattcgc gttaaatttt tgttaaatca gctcattttt   6000
taaccaatag gccgaaatcg gcaaaatccc ttataaatca aaagaataga ccgagatagg   6060
gttgagtgtt gttccagttt ggaacaagag tccactatta agaacgtgg actccaacgt   6120
caaagggcga aaaaccgtct atcagggcga tggcccacta cgtgaaccat cacctaatc   6180
aagttttttg gggtcgaggt gccgtaaagc actaaatcgg aacctaaag ggagcccccg   6240
atttagagct tgacggggaa agccggcgaa cgtggcgaga aggaaggga agaaagcgaa   6300
aggagcgggc gctagggcgc tggcaagtgt agcggtcacg ctgcgcgtaa ccaccacacc   6360
cgccgcgctt aatgcgccgc tacagggcgc gtcccattcg ccattcaggc tgcgcaactg   6420
ttgggaaggg cgatcggtgc gggcctcttc gctattacgc cagctggcga aggggggatg   6480
tgctgcaagg cgattaagtt gggtaacgcc agggttttcc cagtcacgac gttgtaaaac   6540
gacggccagt gagcgcgcgt aatacgactc actatagggc gaattggagc tccaccgcgg   6600
```
tggcggccgc t                                                          6611

<210> SEQ ID NO 25
<211> LENGTH: 2187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ctcgaggttt aaacgaattc cgccaccatg ggacagaccg tgacaacacc cctgagcctg      60
acactgggac attggaagga cgtggagcgc atcgcacata accagagcgt ggacgtgaag     120
aagcggagat gggtgacctt ctgctccgcc gagtggccca ccttcaacgt gggatggccc     180
cgggacggca ccttcaacag agatctgatc acacaggtga agatcaaggt gttttctcca     240
ggaccacacg gacacccaga ccaggtgccc tatatcgtga cctggaggc cctggccttc      300
gatccacctc catgggtgaa gccttttgtg cacccaaagc cacctccacc actgcctcca     360
agcgcccctt ccctgccact ggagccacct cggagcaccc cacccagaag ctccctgtat     420
cccgccctga cacctagcct gggggccaag cctaagccac aggtgctgtc cgactctgga     480
ggaccactga tcgacctgct gaccgaggac cccccaccat accgcgatcc ccggcctcca     540
ccatccgacc gggatggaaa tgaggagag gcaacacctg ccggcgaggc ccccgaccct     600
agcccaatgg cctcccgcct gcggggcagg cgcgagcctc cagtggccga ttctaccaca     660
agccaggcat ccctctgag agcaggagga aatggccagc tccagtattg gccatttct      720
agctccgacc tgtacaactg gaagaacaat aaccctagct tctccgagga ccccggcaag     780
ctgaccgccc tgatcgagag cgtgctgatc acccaccagc ccacatggga cgattgtcag     840
cagctcctgg gcaccctgct gaccggagag gagaagcaga gggtgctgct ggaggcaagg     900
aaggccgtga gggcgacga tggccgccca acccagctcc caaatgaggt ggatgccgcc     960
tttcctctgg agcggccaga ctgggattat accacacagg ccggcagaaa ccacctggtg    1020
cactacagac agctcctgct ggccggcctg cagaatgccg gcagaagccc caccaacctg    1080
gccaaggtga agggcatcac acagggcccc aatgagtctc ctagcgcctt tctggagcgc    1140
ctgaaggagg cctaccggag atatacccca tacgaccctg aggaccccgg acaggagaca    1200
aacgtgtcca tgtctttcat ctggcagagc gcccccgaca tcggcaggaa gctggagcgc    1260
ctggaggacc tgaagaataa gaccctgggc gatctggtga gggaggccga aagatcttc     1320
aacagcgccg agacacctga ggagagagag gagcggatca cagggagac agaggagaag    1380
gaggagcgga gaaggacaga ggacgagcag aaggagaagg agagggatcg ccggagacac    1440
cgcgagatga gcaagctgct ggccaccgtg gtgtccggac agaagcagga caggcaggga    1500
ggagagcggc ggcggagcca gctcgacaga gatcagtgcg cctattgtaa ggagaagggc    1560
cactgggcca aggattgccc caagaagcct cgcggcccac ggggcccag acctcagacc    1620
tccctgctga cactggacga tgatccagcc gtgatcggca cagccgtgaa gggcaaggag    1680
gccgtgcact ctgacctggg ctactggatc gagagcgaga agaatgatac ctggaggctg    1740
aagcgcgccc acctgatcga gatgaagaca tgcgagtggc ctaagtccca caccctgtgg    1800
acagacggca tcgaggagtc tgatctgatc atccccaagt ccctggccgg ccctctgtct    1860
caccacaaca ccaggagggg ctatcgcaca cagatgaagg ccccctggca cagcgaggag    1920
ctggagatca ggtttgagga gtgccctggc accaaggtgc atgtggagga gacatgtggc    1980
```

```
-continued acaaggggcc catccctgcg ctctaccaca gccagcggca gagtgatcga ggagtggtgc    2040
tgtagagagt gcacaatgcc acctctgagc ttccgcgcaa aggacggctg ttggtacggc    2100
atggagatcc gccctagaaa agagcccgag agcaatctgg tcaggtcaat ggtcaccgct    2160
gggtcctaag aattccacgt gggatcc                                        2187
```

VACCINE COMPOSITIONS FOR TREATMENT OF ZIKA VIRUS

CROSS REFERENCE TO RELATED APPLICATIONS

This application claims the benefit of U.S. Provisional Application No. 62/363,545, filed Jul. 18, 2016, and of U.S. Provisional Application No. 62/413,007, filed Oct. 26, 2016, the contents of both of which are incorporated by reference herein in their entirety.

SEQUENCE LISTING

The specification includes a Sequence Listing in the form of an ASCII compliant text file named "2007801-0120_SL.txt", which was created on Jul. 20, 2017 and has a size of 108,123 bytes, the contents of which are hereby incorporated by reference in their entirety.

FIELD OF THE INVENTION

This invention is in the field of vaccines, in particular virus like particle vaccines for Zika virus (ZIKV).

BACKGROUND

ZIKV is a non-segmented, single stranded positive sense RNA virus belonging to the family Flaviviridae in the genus Flavivirus. It is enveloped and icosahedral and it is related to dengue, yellow fever and West Nile virus. ZIKV is spread primarily by mosquitos in the *Aedes* genus, primarily *Aedes aegypti*. However, ZIKV can also be spread in the human population by sexual transmission, even in circumstances where the infected partner has no symptoms of infection. ZIKV can be found in the sperm of infected subjects for up to six months following infection thus creating a longterm risk of exposure for partners and unborn children. ZIKV can also be transmitted through blood transfusion.

ZIKV causes infection in humans, which causes fever, rash, joint pain and headache. Although the symptoms of Zika fever are mild in most patients, infection in adults has been associated with rare cases of Guillain-Barre Syndrome, an autoimmune disease causing muscle weakness, pain and even death (Cor-Lormeau et al., 2016, Lancet 387: 1531-39). Furthermore, infection during pregnancy has been associated with microcephaly, and other severe brain malformations in some babies including loss of normal brain tissue, abnormal brain folding and calcification (infection-related scarring) (Soares de Oliveira-Szeinfeld et al., 2016, Radiology 281: 203-218). ZIKV exposure in utero has also be linked to eye defects, hearing loss and impaired growth. Recent studies in mice have shown that ZIKV infection causes damage to the testes of male mice with a resulting reduction in sperm count and reduced rates of pregnancy in female mice mated with the ZIKV-infected males (Govero, J. et al., (2016) Nature 540: 438-448).

ZIKV was first discovered in a monkey in Uganda in 1947 and was identified in humans shortly thereafter. Sporatic outbreaks occurred in Africa and Asia in the 1960's and 1980's. Between 2007 and 2013, outbreaks occurred in Micronesia and Oceania. Three separate lineages of ZIKV have been identified, two associated with the African outbreaks and one associated with the Asian outbreak. In 2015, an outbreak began in Brazil which quickly spread through 25 additional countries in South America and the Caribbean islands with alarming rates of microcephaly reported (Samarasekera et al., 2016, Lancet 387: 521-524). In January, 2016, the U.S. National Institutes of Health confirmed that the ZIKV outbreak in South America and the Caribbean had reached pandemic levels. On Feb. 1, 2016, the World Health Organization declared the clusters of microcephaly and neurological disorders and their association with ZIKV to be a global public health emergency. In 2016, ZIKV cases were reported in the US states of Florida and Texas which were acquired by local mosquito-borne transmission.

Vaccines have been developed for other flaviruses including yellow fever virus and dengue infection. However, prior to the outbreak of the ZIKV epidemic in the Americas in 2015, little was known about ZIKV immunology. There is currently no commercially available vaccine available for ZIKV.

In June of 2016, the Walter Reed Army Institute of Research and Harvard Medical School published the results of immunological studies using two different vaccine candidates, one a plasmid DNA vaccine and one a purified inactivated virus (PIV) vaccine derived from a ZIKV strain from Puerto Rico (Larocca et al., 2016, Nature: doi: 10.1038). Both vaccines were shown to induce ZIKV specific neutralizing antibodies after a single immunization. These results have demonstrated that it is possible to formulate a vaccine to ZIKV which will induce an immunogenic response. However, no vaccine has yet been shown to be a strong candidate for a human ZIKV vaccine. Plasmid DNA vaccines have proven to be poorly immunogenic in clinical trials in humans (Ferraro et al., 2011, Clin. Infec. Dis. 53: 296-302). Inactivated virus vaccines frequently show a weak immune response in humans, thus requiring the use of multiple booster injections, which may be impractical to track and deliver in developing countries. Furthermore, inactivated vaccines can have adverse side effects.

Accordingly, a need exists for a vaccine against ZIKV.

SUMMARY

The present disclosure provides methods and compositions useful for prophylaxis and/or study of ZIKV infection. These methods and compositions could also be useful to prevent or reduce damage to testes of patients suffering from ZIKV. More particularly, the present disclosure provides methods for production of, and compositions comprising virus like particles (VLPs) expressing antigens from ZIKV which are useful for prevention, treatment, diagnosis and study of ZIKV.

The present disclosure provides virus-like particles which comprise one or more Moloney Murine leukemia virus (MMLV) core proteins and are surrounded by a lipid bilayer membrane. The VLPs include one or more ZIKV polypeptides (e.g., one or more ZIKV polypeptide epitopes) that play a role in induction of virus-neutralizing antibodies. In some embodiments, the ZIKV polypeptides are envelope glycoproteins. In some embodiments, the envelope glycoproteins are ZIKV M and E polypeptides.

In some embodiments, the present disclosure provides VLPs having an envelope that comprises a modified ZIKV envelope glycoprotein. In an embodiment, the present disclosure encompasses production of VLPs having envelopes that include a ZIKV polypeptide in a premature conformation. In a specific embodiment, the modified envelope glycoprotein lacks a furin cleavage site. In another specific embodiment, the modified envelope glycoprotein lacks a glycosylation site. In a preferred embodiment, the modified envelope glycoprotein consists solely of the ZIKV E polypeptide, without the presence of the ZIKV M polypeptide.

In a further embodiment, the modified envelope glycoprotein has been modified such that the transmembrane domain is replaced with the transmembrane domain of another virus. In a particularly preferred embodiment, the VLP has a modified envelope glycoprotein comprising an isolated ZIKV E protein, the transmembrane domain and cytoplasmic tail of which ZIKV E protein have been replaced with the transmembrane domain and cytoplasmic tail from vesicular stomatitis virus (VSV).

In some embodiments, the VLPs of the invention contain one or more epitopes from ZIKV non-structural proteins which are antigens that play a role in induction of cellular immune responses (e.g., T-cell response). As is known to those of skill in the art of immunology, cell mediated immunity is an important aspect of long term immunity and cellular defense against pathogens. In some embodiments, the viral non-structural proteins both stimulate formation of T-helper cells and also induce cytotoxic T lymphocytes (CTL) against ZIKV. In some embodiments, the viral non-structural protein is NS1 from ZIKV.

The present disclosure further provides VLPs comprising variants of the ZIKV NS1 non-structural protein. In some embodiments, a variant of a ZIKV non-structural protein is or comprises a modified NS1 protein. In a preferred embodiment, the modified non-structural NS1 protein is a truncated ZIKV NS1 protein.

The present disclosure further provides bivalent VLPs comprising an ZIKV envelope protein and a ZIKV non-structural protein. In some embodiments, one or both of these proteins are modified proteins. In some embodiments, the modified non-structural protein is a truncated ZIKV NS1.

In a particularly preferred embodiment, the invention comprises a bivalent VLP, wherein the bivalent VLP comprises an isolated ZIKV E protein, the transmembrane domain and cytoplasmic tail of which ZIKV E protein have been replaced with the transmembrane domain and cytoplasmic tail from VSV, and a truncated ZIKV NS1 protein. Significantly, this bivalent VLP has been shown to induce both an antibody response, and a T cell response, and thereby produce a strong immunological defence to ZIKV.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 4 shows the structure of a first expression cassette encoding ZIKV envelope glycoproteins, and a second expression cassette encoding MMLV-GAG and a third expression cassette encoding a GAG/NS1 fusion protein.

FIG. 5 shows a Western blot analysis of purified VLPs expressing ZIKV envelope proteins.

FIG. 7 shows cryoTEM images. (A) shows an image at 110,000× magnification of VLPs incorporating prME (SEQ ID NO: 6)—Gag (0.05 µg/ml ZIKV plasmid). (B) shows an image at 110,000× magnification of VLPs incorporating prMuE (SEQ ID NO: 9)-Gag (0.05 µg/ml ZIKV plasmid).

FIG. 8 shows nsTEM images. (A) shows an image at 40,000× magnification of VLPs incorporating prMuE (SEQ ID NO: 9)—Gag (0.05 µg/ml ZIKV plasmid). (B) shows an image at 40,000× magnification of VLPs incorporating prME (SEQ ID NO: 6)—Gag (0.05 µg/ml ZIKV plasmid). (C) shows an image at 40,000× magnification of VLPs incorporating ZIKV-EG VSV—(SEQ ID NO: 12)—(0.2 µg/ml ZIKV plasmid). (D) shows an image at 40,000× magnification of VLPs incorporating prME156 (SEQ ID NO: 15)—(0.05 mg/ml ZIKV plasmid).

LISTING OF SEQUENCES

Figure 1:
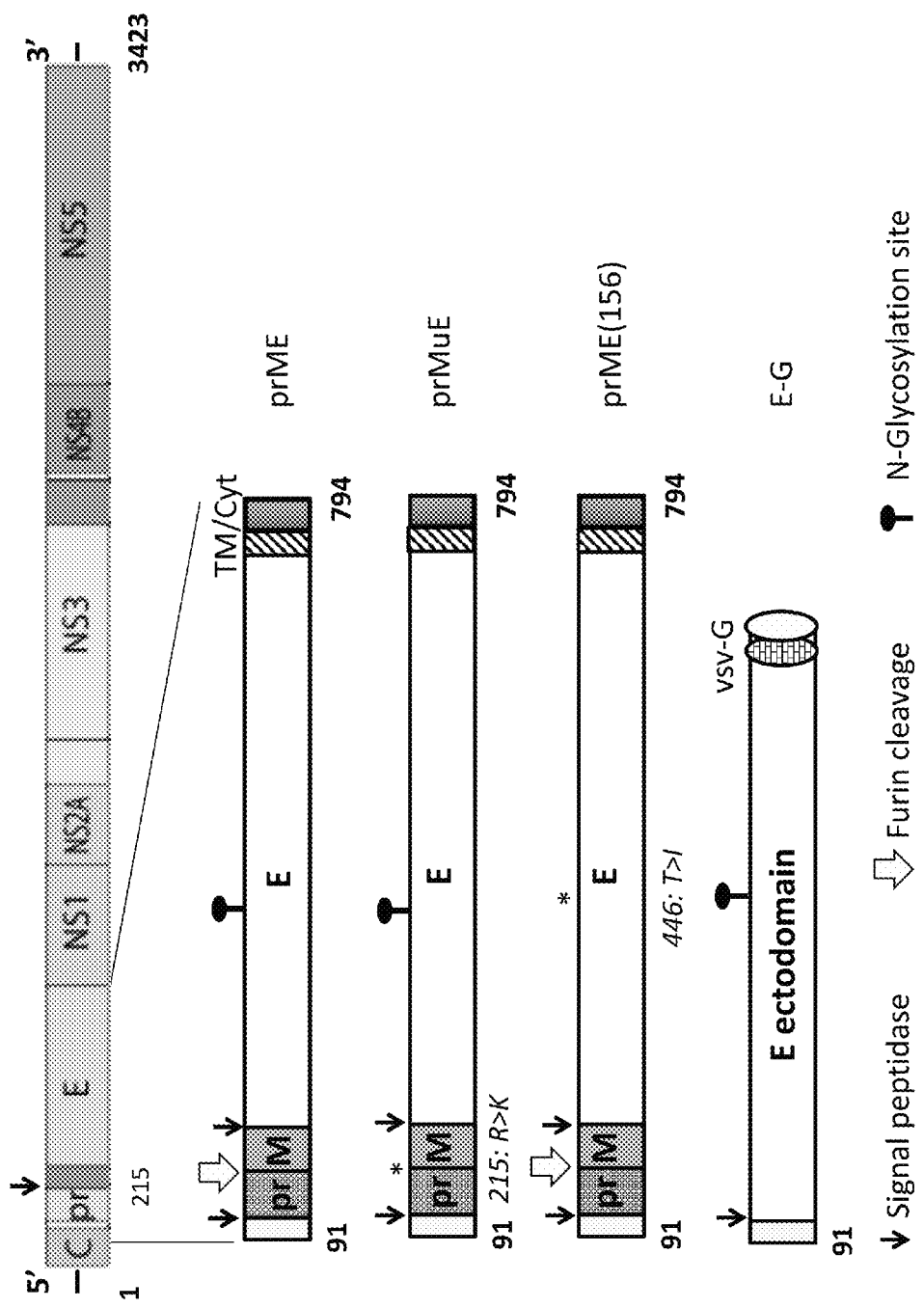
FIG. 1 is a diagram illustrating the structure of the ZIKV envelope genome and mutants described herein.

The following is a list of sequences referred to herein:

```
SEQ ID NO: 1 is an MMLV-Gag Amino Acid Sequence
MGQTVTTPL SLTLGHWKDVERIAHNQSVDVKKRRWVTFCSAEWPTFNVG

WPRDGTFNRDLITQVKIKVFSPGPHGHPDQVPYIVTWEALAFDPPPWVKP

FVHPKPPPPLPPSAPSLPLEPPRSTPPRSSLYPALTPSLGAKPKPQVLSD

SGGPLIDLLTEDPPPYRDPRPPPSDRDGNGGEATPAGEAPDPSPMASRLR

GRREPPVADSTTSQAFPLRAGGNGQLQYWPFSSSDLYNWKNNNPSFSEDP

GKLTALIESVLITHQPTWDDCQQLLGTLLTGEEKQRVLLEARKAVRGDDG

RPTQLPNEVDAAFPLERPDWDYTTQAGRNHLVHYRQLLLAGLQNAGRSPT

NLAKVKGITQGPNESPSAFLERLKEAYRRYTPYDPEDPGQETNVSMSFIW

QSAPDIGRKLERLEDLKNKTLGDLVREAEKIFNKRETPEEREERIRRETE

EKEERRRTEDEQKEKERDRRRHREMSKLLATVVSGQKQDRQGGERRRSQL

DRDQCAYCKEKGHWAKDCPKKPRGPRGPRPQTSLLTLDD

SEQ ID NO: 2 is MMLV-Gag Nucleotide Sequence
ATGGGCCAGACTGTTACCACTCCCTTAAGTTTGACCTTAGGTCACTGGAA

AGATGTCGAGCGGATCGCTCACAACCAGTCGGTAGATGTCAAGAAGAGAC

GTTGGGTTACCTTCTGCTCTGCAGAATGGCCAACCTTTAACGTCGGATGG

CCGCGAGACGGCACCTTTAACCGAGACCTCATCACCCAGGTTAAGATCAA

GGTCTTTTCACCTGGCCCGCATGGACACCCAGACCAGGTCCCCTACATCG

TGACCTGGGAAGCCTTGGCTTTTGACCCCCCTCCCTGGGTCAAGCCCTTT

GTACACCCTAAGCCTCCGCCTCCTCTTCCTCCATCCGCCCCGTCTCTCCC

CCTTGAACCTCCTCGTTCGACCCCGCCTCGATCCTCCCTTTATCCAGCCC

TCACTCCTTCTCTAGGCGCCAAACCTAAACCTCAAGTTCTTTCTGACAGT

GGGGGGCCGCTCATCGACCTACTTACAGAAGACCCCCCGCCTTATAGGGA

CCCAAGACCACCCCCTTCCGACAGGGACGGAAATGGTGGAGAAGCGACCC
```

-continued
CTGCGGGAGAGGCACCGGACCCCTCCCCAATGGCATCTCGCCTACGTGGG

AGACGGGAGCCCCCTGTGGCCGACTCCACTACCTCGCAGGCATTCCCCCT

CCGCGCAGGAGGAAACGGACAGCTTCAATACTGGCCGTTCTCCTCTTCTG

ACCTTTACAACTGGAAAAATAATAACCCTTCTTTTTCTGAAGATCCAGGT

AAACTGACAGCTCTGATCGAGTCTGTTCTCATCACCCATCAGCCCACCTG

GGACGACTGTCAGCAGCTGTTGGGACTCTGCTGACCGGAGAAGAAAAAC

AACGGGTGCTCTTAGAGGCTAGAAAGGCGGTGCGGGCGATGATGGGCGC

CCCACTCAACTGCCCAATGAAGTCGATGCCGCTTTTCCCCTCGAGCGCCC

AGACTGGGATTACACCACCCAGGCAGGTAGGAACCACCTAGTCCACTATC

GCCAGTTGCTCCTAGCGGGTCTCCAAAACGCGGGCAGAAGCCCCCACCAAT

TTGGCCAAGGTAAAAGGAATAACACAAGGGCCCAATGAGTCTCCCTCGGC

CTTCCTAGAGAGACTTAAGGAAGCCTATCGCAGGTACACTCCTTATGACC

CTGAGGACCCAGGGCAAGAAACTAATGTGTCTATGTCTTTCATTTGGCAG

TCTGCCCCAGACATTGGGAGAAAGTTAGAGAGGTTAGAAGATTTAAAAAA

CAAGACGCTTGGAGATTTGGTTAGAGAGGCAGAAAAGATCTTTAATAAAC

GAGAAACCCCGGAAGAAAGAGAGGAACGTATCAGGAGAGAAACAGAGGAA

AAAGAAGAACGCCGTAGGACAGAGGATGAGCAGAAAGAGAAAGAAAGAGA

TCGTAGGAGACATAGAGAGATGAGCAAGCTATTGGCCACTGTCGTTAGTG

GACAGAAACAGGATAGACAGGGAGGAGAACGAAGGAGGTCCCAACTCGAT

CGCGACCAGTGTGCCTACTGCAAAGAAAAGGGGCACTGGGCTAAAGATTG

TCCCAAGAAACCACGAGGACCTCGGGGACCAAGACCCCAGACCTCCCTCC

TGACCCTAGATGAC

SEQ ID NO: 3 is a Codon Optimized
MMLV-Gag Nucleotide Sequence
ATGGGACAGACCGTCACAACACCCCTGAGCCTGACCCTGGGACATTGGAA

AGACGTGGAGAGGATCGCACATAACCAGAGCGTGGACGTGAAGAAACGGA

GATGGGTCACATTCTGCAGTGCTGAGTGGCCAACTTTTAATGTGGGATGG

CCCCGAGACGGCACTTTCAACAGGGATCTGATCACCCAGGTGAAGATCAA

GGTCTTTAGCCCAGGACCTCACGGACATCCAGACCAGGTGCCTTATATCG

TCACCTGGGAGGCACTGGCCTTCGATCCCCCTCCATGGGTGAAGCCATTT

GTCCACCCAAAACCACCTCCACCACTGCCTCCAAGTGCCCCTTCACTGCC

ACTGGAACCACCCCGGAGCACACCACCCCGCAGCTCCCTGTATCCTGCTC

TGACTCCATCTCTGGGCGCAAAGCCAAAACCACAGGTGCTGAGCGACTCC

GGAGGACCACTGATTGACCTGCTGACAGAGGACCCCCCACCATACCGAGA

TCCTCGGCCTCCACCAAGCGACCGCGATGGAAATGGAGGAGAGGCTACTC

CTGCCGGCGAAGCCCCTGACCCATCTCCAATGGCTAGTAGGCTGCGCGGC

AGGCGCGAGCCTCCAGTGGCAGATAGCACCACATCCCAGGCCTTCCCTCT

GAGGGCTGGGGAAATGGGCAGCTCCAGTATTGGCCATTTTCTAGTTCAG

ACCTGTACAACTGGAAGAACAATAACCCCTCTTCAGTGAGGACCCCGGC

AAACTGACCGCCCTGATCGAATCCGTGCTGATTACCCATCAGCCCACATG

-continued
GGACGATTGTCAGCAGCTCCTGGGCACCCTGCTGACCGGAGAGGAAAAGC

AGCGCGTGCTGCTGGAGGCTCGCAAAGCAGTCCGAGGGGACGATGGACGG

CCCACACAGCTCCCTAATGAGGTGGACGCCGCTTTTCCACTGGAAAGACC

CGACTGGGATTATACTACCCAGGCAGGGAGAAACCACCTGGTCCATTACA

GGCAGCTCCTGCTGGCAGGCCTGCAGAATGCCGGGAGATCCCCCACCAAC

CTGGCCAAGGTGAAAGGCATCACACAGGGGCCTAATGAGTCACCAAGCGC

CTTTCTGGAGAGGCTGAAGGAAGCTTACCGACGGTATACCCCATACGACC

CTGAGGACCCCGGACAGGAAACAAACGTCTCCATGTCTTTCATCTGGCAG

TCTGCCCCAGACATTGGGCGGAAGCTGGAGAGACTGGAAGACCTGAAGAA

CAAGACCCTGGGCGACCTGGTGCGGGAGGCTGAAAAGATCTTCAACAAAC

GGGAGACCCCCGAGGAAAGAGAGGAAAGGATTAGAAGGGAAACTGAGGAA

AAGGAGGAACGCCGACGGACCGAGGACGAACAGAAGGAGAAAGAACGAGA

TCGGCGGCGGCACCGGGAGATGTCAAAGCTGCTGGCCACCGTGGTCAGCG

GACAGAAACAGGACAGACAGGGAGGAGAGCGACGGAGAAGCCAGCTCGAC

AGGGATCAGTGCGCATACTGTAAGGAAAAAGGCCATTGGGCCAAGGATTG

CCCCAAAAAGCCAAGAGGACCAAGAGGACCAAGACCACAGACATCACTGC

TGACCCTGGACGAC

SEQ ID NO: 4 is a ZIKV prME amino acid sequence
MLRIINARKEKKRRGADTSVGIVGLLLTTAMAAEVTRRGSAYYMYLDRND

AGEAISFPTTLGMNKCYIQIMDLGHTCDATMSYECPMLDEGVEPDDVDCW

CNTTSTWVVYGTCHHKKGEARRSRRAVTLPSHSTRKLQTRSQTWLESREY

TKHLIRVENWIFRNPGFALAAAAIAWLLGSSTSQKVIYLVMILLIAPAYS

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPEALVEFKDAHAKRQTV

VVLGSQEGAVHTALAGALEAEMDGAKGRLSSGHLKCRLKMDKLRLKGVSY

SLCTAAFTFTKIPAETLHGTVTVEVQYAGTDGPCKVPAQMAVDMQTLTPV

GRLITANPVITESTENSKMMLELDPPFGDSYIVIGVGEKKITHHWHRSGS

TIGKAFEATVRGAKRMAVLGDTAWDFGSVGGALNSLGKGIHQIFGAAFKS

LFGGMSWFSQILIGTLLMWLGLNAKNGSISLMCLALGGVLIFLSTAVSA

SEQ ID NO: 5 is a ZIKV prME Nucleotide Sequence

ATGCTGAGAATAATCAATGCTAGGAAGGAGAAGAAGAGACGAGGCGCAGA

TACTAGTGTCGGAATTGTTGGCCTCCTGCTGACCACAGCTATGGCAGCGG

AGGTCACTAGACGTGGGAGTGCATACTATATGTACTTGGACAGAAACGAT

GCTGGGGAGGCCATATCTTTTCCAACCACATTGGGGATGAATAAGTGTTA

TATACAGATCATGGATCTTGGACACACGTGTGATGCCACCATGAGCTATG

AATGCCCTATGCTGGATGAGGGGGTGGAACCAGATGACGTCGATTGTTGG

-continued
TGCAACACGACGTCAACTTGGGTTGTGTACGGAACCTGCCATCACAAAAA
AGGTGAAGCACGGAGATCTAGAAGAGCTGTGACGCTCCCCTCCCATTCCA
CTAGGAAGCTGCAAACGCGGTCGCAAACCTGGTTGGAATCAAGAGAATAC
ACAAAGCACTTGATTAGAGTCGAAAATTGGATATTCAGGAACCCTGGCTT
CGCGTTAGCAGCAGCTGCCATCGCTTGGCTTTTGGGAAGCTCAACGAGCC
AAAAAGTCATATACTTGGTCATGATACTGCTGATTGCCCCGGCATACAGC
ATCAGGTGCATAGGAGTCAGCAATAGGGACTTTGTGGAAGGTATGTCAGG
TGGGACTTGGGTTGATGTTGTCTTGGAACATGGAGGTTGTGTCACTGTAA
TGGCACAGGACAAACCGACTGTCGACATAGAGCTGGTTACAACAACAGTC
AGCAACATGGCGGAGGTAAGATCCTACTGCTATGAGGCATCAATATCAGA
CATGGCTTCGGACAGCCGCTGCCCAACACAAGGTGAAGCCTACCTTGACA
AGCAATCAGACACTCAATATGTCTGCAAAAGAACGTTAGTGGACAGAGGC
TGGGGAAATGGATGTGGACTTTTTGGCAAAGGGAGCCTGGTGACATGCGC
TAAGTTTGCATGCTCCAAGAAAATGACCGGGAAGAGCATCCAGCCAGAGA
ATCTGGAGTACCGGATAATGCTGTCAGTTCATGGCTCCCAGCACAGTGGG
ATGATCGTTAATGACACAGGACATGAAACTGATGAGAATAGAGCGAAAGT
TGAGATAACGCCCAATTCACCAAGAGCCGAAGCCACCCTGGGGGGGTTTG
GAAGCCTAGGACTTGATTGTGAACCGAGGACAGGCCTTGACTTTTCAGAT
TTGTATTACTTGACTATGAATAACAAGCACTGGCTGGTTCACAAGGAGTG
GTTCCACGACATTCCATTACCTTGGCACGCTGGGGCAGACACCGGAACTC
CACACTGGAACAACAAAGAAGCACTGGTAGAGTTCAAGGACGCACATGCC
AAAAGGCAAACTGTCGTGGTTCTAGGGAGTCAAGAAGGAGCAGTTCACAC
GGCCCTTGCTGGAGCTCTGGAGGCTGAGATGGATGGTGCAAAGGGAAGGC
TGTCCTCTGGCCACTTGAAATGTCGCCTGAAAATGGATAAACTTAGATTG
AAGGGCGTGTCATACTCCTTGTGTACTGCAGCGTTCACATTCACCAAGAT
CCCGGCTGAAACACTGCACGGGACAGTCACAGTGGAGGTACAGTACGCAG
GGACAGATGGACCTTGCAAGGTTCCAGCTCAGATGGCGGTGGACATGCAA
ACTCTGACCCCAGTGGGAGGTTGATAACGCTAACCCCGTAATCACTGA
AAGCACTGAGAACTCTAAGATGATGCTGGAACTTGATCCACCATTTGGGG
ACTCTTACATTGTCATAGGAGTCGGGGAGAAGAAGATCACCCACCACTGG
CACAGGAGTGGCAGCACCATTGGAAAAGCATTTGAAGCCACTGTGAGAGG
TGCCAAGAGAATGGCAGTCTTGGGAGACACAGCCTGGGACTTTGGATCAG
TTGGAGGCGCTCTCAACTCATTGGGCAAGGGCATCCATCAAATCTTTGGA
GCAGCTTTCAAATCATTGTTTGGAGGAATGTCCTGGTTCTCACAAATTCT
CATTGGAACGTTGCTGATGTGGTTGGGTCTGAACGCAAAGAATGGATCTA
TTTCCCTTATGTGCTTGGCCTTAGGGGGAGTGTTGATCTTCTTATCCACA
GCCGTCTCTGCTTAA SEQ ID NO: 6 is a Codon Optimized
ZIKV prME Nucleotide Sequence
ATGCTGAGGATCATCAATGCCCGCAAGGAGAAGAAGCGGAGAGGAGCCGA
CACAAGCGTGGGCATCGTGGGCCTGCTGCTGACCACAGCAATGGCCGCCG
AGGTGACCAGGAGGGGCAGCGCCTACTATATGTACCTGGACCGGAATGAT
GCCGGCGAGGCCATCTCCTTTCCCACCACACTGGGCATGAACAAGTGCTA
CATCCAGATCATGGACCTGGGCCACATGTGCGATGCCACCATGTCCTATG
AGTGTCCAATGCTGGACGAGGGCGTGGAGCCCGACGATGTGGATTGCTGG
TGTAACACCACATCTACATGGGTGGTGTACGGCACCTGTCACCACAAGAA
GGGAGAGGCCCGGCGGAGCCGGCGGGCCGTGACACTGCCTTCCCACTCTA
CCCCGGAAGCTGCAGACAAGAAGCCAGACCTGGCTGGAGTCCCGGGAGTAT
ACCAAGCACCTGATCCGGGTGGAGAACTGGATCTTTAGAAATCCAGGATT
CGCCCTGGCCGCCGCCGCCATCGCATGGCTGCTGGGCAGCTCCACCAGCC
AGAAAGTGATCTACCTGGTCATGATCCTGCTGATCGCCCCTGCCTATTCT
ATCAGGTGCATCGGCGTGAGCAACCGGGACTTCGTGGAGGGAATGTCCGG
AGGCACCTGGGTGGATGTGGTGCTGGAGCACGGCGGCTGCGTGACAGTGA
TGGCCCAGGACAAGCCAACCGTGGACATCGAGCTGGTGACCACAACCGTG
TCCAACATGGCCGAGGTGCGGTCTTACTGCTATGAGGCCAGCATCTCCGA
CATGGCCTCTGATAGCAGATGTCCCACCCAGGGCGAGGCCTACCTGGACA
AGCAGTCCGATACACAGTACGTGTGCAAGAGGACCCTGGTGGACAGGGGA
TGGGGAAATGGATGTGGCCTGTTTGGCAAGGGCTCTCTGGTGACATGCGC
CAAGTTCGCCTGTAGCAAGAAGATGACCGGCAAGTCCATCCAGCCAGAGA
ACCTGGAGTACAGGATCATGCTGTCTGTGCACGGCTCCCAGCACTCTGGC
ATGATCGTGAACGACACAGGCCACGAGACAGATGAGAATAGGGCCAAGGT
GGAGATCACACCTAACTCCCCACGCGCCGAGGCCACCCTGGGCGGATTTG
GCTCTCTGGGCCTGGACTGCGAGCCTCGCACAGGCCTGGACTTCTCCGAT
CTGTACTATCTGACCATGAACAATAAGCACTGGCTGGTGCACAAGGAGTG
GTTTCACGACATCCCACTGCCATGGCACGCAGGAGCCGATACAGGCACCC
CACACTGGAACAATAAGGAGGCCCTGGTGGAGTTCAAGGATGCCCACGCC
AAGAGGCAGACAGTGGTGGTGCTGGGCAGCCAGGAGGGAGCCGTGCACAC
CGCCCTGGCCGGGGCCCTGGAGGCAGAGATGGACGGAGCCAAGGGCCGCC
TGTCTAGCGGACACCTGAAGTGCCGGCTGAAGATGGATAAGCTGAGACTG
AAGGGCGTGTCCTACTCTCTGTGCACCGCCGCCTTCACCTTCACCAAGAT
CCCCGCCGAGACACTGCACGGCACAGTGACCGTGGAGGTGCAGTATGCCG
GCACAGACGGCCCCTGTAAGGTGCCTGCCCAGATGGCCGTGGATATGCAG
ACACTGACCCCTGTGGGCCGGCTGATCACCGCAAATCCAGTGATCACAGA
GTCTACCGAGAACAGCAAGATGATGCTGGAGCTGGACCCCCCTTTTGGCG
ATAGCTATATCGTGATCGGCGTGGGCGAGAAGAAGATCACACACCACTGG
CACAGAAGCGGCTCCACAATCGGCAAGGCCTTTGAGGCAACCGTGCGGGG
AGCCAAGAGAATGGCCGTGCTGGGCGACACCGCATGGGATTTCGGCTCTG
TGGGAGGGGCACTGAACAGCCTGGGGAAGGGCATCCACCAGATCTTCGGA
GCCGCCTTTAAGTCCCTGTTCGGCGGCATGAGCTGGTTTTCCCAGATCCT

GATCGGCACCCTGCTGATGTGGCTGGGCCTGAACGCCAAGAATGGCTCTA

TCAGCCTGATGTGCCTGGCCCTGGGCGGCGTGCTGATCTTCCTGTCCACC

GCCGTGTCTGCCTGA

SEQ ID NO: 7 is a ZIKV prMuE amino acid sequence
MLRIINARKEKKRRGADTSVGIVGLLLTTAMAAEVTRRGSAYYMYLDRND

AGEAISFPTTLGMNKCYIQIMDLGHTCDATMSYECPMLDEGVEPDDVDCW

CNTTSTWVVYGTCHHKKGEARRSRKAVTLPSHSTRKLQTRSQTWLESREY

TKHLIRVENWIFRNPGFALAAAAIAWLLGSSTSQKVIYLVMILLIAPAYS

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNAKNGSISLMCLALGGVLIFLST

AVSA

SEQ ID NO: 8 is a ZIKV prMuE Nucleotide Sequence
ATGCTGAGAATAATCAATGCTAGGAAGGAGAAGAAGAGACGAGGCGCAGA

TACTAGTGTCGGAATTGTTGGCCTCCTGCTGACCACAGCTATGGCAGCGG

AGGTCACTAGACGTGGGAGTGCATACTATATGTACTTGGACAGAAACGAT

GCTGGGGAGGCCATATCTTTTCCAACCACATTGGGGATGAATAAGTGTTA

TATACAGATCATGGATCTTGGACACACGTGTGATGCCACCATGAGCTATG

AATGCCCTATGCTGGATGAGGGGGTGGAACCAGATGACGTCGATTGTTGG

TGCAACACGACGTCAACTTGGGTTGTGTACGGAACCTGCCATCACAAAAA

AGGTGAAGCACGGAGATCTAGAAAAGCTGTGACGCTCCCCTCCCATTCCA

CTAGGAAGCTGCAAACGCGGTCGCAAACCTGGTTGGAATCAAGAGAATAC

ACAAAGCACTTGATTAGAGTCGAAAATTGGATATTCAGGAACCCTGGCTT

CGCGTTAGCAGCAGCTGCCATCGCTTGGCTTTTGGGAAGCTCAACGAGCC

AAAAAGTCATATACTTGGTCATGATACTGCTGATTGCCCCGGCATACAGC

ATCAGGTGCATAGGAGTCAGCAATAGGGACTTTGTGGAAGGTATGTCAGG

TGGGACTTGGGTTGATGTTGTCTTGGAACATGGAGGTTGTGTCACTGTAA

TGGCACAGGACAAACCGACTGTCGACATAGAGCTGGTTACAACAACAGTC

AGCAACATGGCGGAGGTAAGATCCTACTGCTATGAGGCATCAATATCAGA

CATGGCTTCGGACAGCCGCTGCCCAACACAAGGTGAAGCCTACCTTGACA

AGCAATCAGACACTCAATATGTCTGCAAAAGAACGTTAGTGGACAGAGGC

TGGGGAAATGGATGTGGACTTTTTGGCAAAGGGAGCCTGGTGACATGCGC

TAAGTTTGCATGCTCCAAGAAAATGACCGGGAAGAGCATCCAGCCAGAGA

ATCTGGAGTACCGGATAATGCTGTCAGTTCATGGCTCCCAGCACAGTGGG

ATGATCGTTAATGACACAGGACATGAAACTGATGAGAATAGAGCGAAAGT

TGAGATAACGCCCAATTCACCAAGAGCCGAAGCCACCCTGGGGGGGTTTG

GAAGCCTAGGACTTGATTGTGAACCGAGGACAGGCCTTGACTTTTCAGAT

TTGTATTACTTGACTATGAATAACAAGCACTGGCTGGTTCACAAGGAGTG

GTTCCACGACATTCCATTACCTTGGCACGCTGGGGCAGACACCGGAACTC

CACACTGGAACAACAAAGAAGCACTGGTAGAGTTCAAGGACGCACATGCC

AAAAGGCAAACTGTCGTGGTTCTAGGGAGTCAAGAAGGAGCAGTTCACAC

GGCCCTTGCTGGAGCTCTGGAGGCTGAGATGGATGGTGCAAAGGGAAGGC

TGTCCTCTGGCCACTTGAAATGTCGCCTGAAAATGGATAAACTTAGATTG

AAGGGCGTGTCATACTCCTTGTGTACTGCAGCGTTCACATTCACCAAGAT

CCCGGCTGAAACACTGCACGGGACAGTCACAGTGGAGGTACAGTACGCAG

GGACAGATGGACCTTGCAAGGTTCCAGCTCAGATGGCGGTGGACATGCAA

ACTCTGACCCCAGTTGGGAGGTTGATAACCGCTAACCCCGTAATCACTGA

AAGCACTGAGAACTCTAAGATGATGCTGGAACTTGATCCACCATTTGGGG

ACTCTTACATTGTCATAGGAGTCGGGGAGAAGAAGATCACCCACCACTGG

CACAGGAGTGGCAGCACCATTGGAAAAGCATTTGAAGCCACTGTGAGAGG

TGCCAAGAGAATGGCAGTCTTGGGAGACACAGCCTGGGACTTTGGATCAG

TTGGAGGCGCTCTCAACTCATTGGGCAAGGGCATCCATCAAATCTTTGGA

GCAGCTTTCAAATCATTGTTTGGAGGAATGTCCTGGTTCTCACAAATTCT

CATTGGAACGTTGCTGATGTGGTTGGGTCTGAACGCAAAGAATGGATCTA

TTTCCCTTATGTGCTTGGCCTTAGGGGGAGTGTTGATCTTCTTATCCACA

GCCGTCTCTGCTTAA

SEQ ID NO: 9 is a Codon Optimized
ZIKV prMuE Nucleotide Sequence
ATGCTGAGGATCATCAATGCCCGCAAGGAGAAGAAGCGGAGAGGAGCCGA

CACAAGCGTGGGCATCGTGGGCCTGCTGCTGACCACAGCAATGGCCGCCG

AGGTGACCAGGAGGGGCAGCGCCTACTATATGTACCTGGACCGGAATGAT

GCCGGCGAGGCCATCTCCTTTCCCACCACACTGGGCATGAACAAGTGCTA

CATCCAGATCATGGACCTGGGCCACACATGCGATGCCACCATGTCCTATG

AGTGTCCAATGCTGGACGAGGGCGTGGAGCCCGACGATGTGGATTGCTGG

TGTAACACCACATCTACATGGGTGGTGTACGGCACCTGTCACCACAAGAA

GGGAGAGGCCCGGCGGAGCCGGAAAGCCGTGACACTGCCTTCCCACTCTA

CCCGGAAGCTGCAGACAAGAAGCCAGACCTGGCTGGAGTCCCGGGAGTAT

ACCAAGCACCTGATCCGGGTGGAGAACTGGATCTTTAGAAATCCAGGATT

CGCCCTGGCCGCCGCCGCCATCGCATGGCTGCTGGGCAGCTCCACCAGCC

AGAAAGTGATCTACCTGGTCATGATCCTGCTGATCGCCCCTGCCTATTCT

ATCAGGTGCATCGGCGTGAGCAACCGGGACTTCGTGGAGGGAATGTCCGG

AGGCACCTGGGTGGATGTGGTGCTGGAGCACGGCGGCTGCGTGACAGTGA

-continued

TGGCCCAGGACAAGCCAACCGTGGACATCGAGCTGGTGACCACAACCGTG

TCCAACATGGCCGAGGTGCGGTCTTACTGCTATGAGGCCAGCATCTCCGA

CATGGCCTCTGATAGCAGATGTCCCACCCAGGGCGAGGCCTACCTGGACA

AGCAGTCCGATACACAGTACGTGTGCAAGAGGACCCTGGTGGACAGGGGA

TGGGGAAATGGATGTGGCCTGTTTGGCAAGGGCTCTCTGGTGACATGCGC

CAAGTTCGCCTGTAGCAAGAAGATGACCGGCAAGTCCATCCAGCCAGAGA

ACCTGGAGTACAGGATCATGCTGTCTGTGCACGGCTCCCAGCACTCTGGC

ATGATCGTGAACGACACAGGCCACGAGACAGATGAGAATAGGGCCAAGGT

GGAGATCACACCTAACTCCCCACGCGCCGAGGCCACCCTGGGCGGATTTG

GCTCTCTGGGCCTGGACTGCGAGCCTCGCACAGGCCTGGACTTCTCCGAT

CTGTACTATCTGACCATGAACAATAAGCACTGGCTGGTGCACAAGGAGTG

GTTTCACGACATCCCACTGCCATGGCACGCAGGAGCCGATACAGGCACCC

CACACTGGAACAATAAGGAGGCCCTGGTGGAGTTCAAGGATGCCCACGCC

AAGAGGCAGACAGTGGTGGTGCTGGGCAGCCAGGAGGAGCCGTGCACAC

CGCCCTGGCCGGGGCCCTGGAGGCAGAGATGGACGGAGCCAAGGGCCGCC

TGTCTAGCGGACACCTGAAGTGCCGGCTGAAGATGGATAAGCTGAGACTG

AAGGGCGTGTCCTACTCTCTGTGCACCGCCGCCTTCACCTTCACCAAGAT

CCCCGCCGAGACACTGCACGGCACAGTGACCGTGGAGGTGCAGTATGCCG

GCACAGACGGCCCCTGTAAGGTGCCTGCCCAGATGGCCGTGGATATGCAG

ACACTGACCCCTGTGGGCCGGCTGATCACCGCAAATCCAGTGATCACAGA

GTCTACCGAGAACAGCAAGATGATGCTGGAGCTGGACCCCCCTTTTGGCG

ATAGCTATATCGTGATCGGCGTGGGCGAGAAGAAGATCACACACCACTGG

CACAGAAGCGGCTCCACAATCGGCAAGGCCTTTGAGGCAACCGTGCGGGG

AGCCAAGAGAATGGCCGTGCTGGGCGACACCGCATGGGATTTCGGCTCTG

TGGGAGGGGCACTGAACAGCCTGGGGAAGGGCATCCACCAGATCTTCGGA

GCCGCCTTTAAGTCCCTGTTCGGCGGCATGAGCTGGTTTTCCCAGATCCT

GATCGGCACCCTGCTGATGTGGCTGGGCCTGAACGCCAAGAATGGCTCTA

TCAGCCTGATGTGCCTGGCCCTGGGCGGCGTGCTGATCTTCCTGTCCACC

GCCGTGTCTGCCTGA

SEQ ID NO: 10 is a ZIKV EG amino acid sequence
MLRIINARKEKKRRGADTSVGIVGLLLTTAMAIRCIGVSNRDFVEGMSGG

TWVDVVLEHGGCVTVMAQDKPTVDIELVTTTVSNMAEVRSYCYEASISDM

ASDSRCPTQGEAYLDKQSDTQYVCKRTLVDRGWGNGCGLFGKGSLVTCAK

FACSKKMTGKSIQPENLEYRIMLSVHGSQHSGMIVNDTGHETDENRAKVE

ITPNSPRAEATLGGFGSLGLDCEPRTGLDFSDLYYLTMNNKHWLVHKEWF

HDIPLPWHAGADTGTPHWNNKEALVEFKDAHAKRQTVVVLGSQEGAVHTA

LAGALEAEMDGAKGRLSSGHLKCRLKMDKLRLKGVSYSLCTAAFTFTKIP

AETLHGTVTVEVQYAGTDGPCKVPAQMAVDMQTLTPVGRLITANPVITES

TENSKMMLELDPPFGDSYIVIGVGEKKITHHWHRSGSTIGKAFEATVRGA

-continued
KRMAVLGDTAWDFGSVGGALNSLGKGIHQIFGAAFKS<u>FFFIIGLIIGLFL</u>

<u>VLRVGIELCIKLKHTKKRQIYTDIEMNRLGK</u>

SEQ ID NO: 11 is a ZIKV EG Nucleotide Sequence
ATGCTGAGAATAATCAATGCTAGGAAGGAGAAGAAGAGACGAGGCGCAGA

TACTAGTGTCGGAATTGTTGGCCTCCTGCTGACCACAGCTATGGCAATCA

GGTGCATAGGAGTCAGCAATAGGGACTTTGTGGAAGGTATGTCAGGTGGG

ACTTGGGTTGATGTTGTCTTGGAACATGGAGGTTGTGTCACTGTAATGGC

ACAGGACAAACCGACTGTCGACATAGAGCTGGTTACAACAACAGTCAGCA

ACATGGCGGAGGTAAGATCCTACTGCTATGAGGCATCAATATCAGACATG

GCTTCGGACAGCCGCTGCCCAACACAAGGTGAAGCCTACCTTGACAAGCA

ATCAGACACTCAATATGTCTGCAAAAGAACGTTAGTGGACAGAGGCTGGG

GAAATGGATGTGGACTTTTTGGCAAAGGGAGCCTGGTGACATGCGCTAAG

TTTGCATGCTCCAAGAAAATGACCGGGAAGAGCATCCAGCCAGAGAATCT

GGAGTACCGGATAATGCTGTCAGTTCATGGCTCCCAGCACAGTGGGATGA

TCGTTAATGACACAGGACATGAAACTGATGAGAATAGAGCGAAAGTTGAG

ATAACGCCCAATTCACCAAGAGCCGAAGCCACCCTGGGGGGGTTTGGAAG

CCTAGGACTTGATTGTGAACCGAGGACAGGCCTTGACTTTTCAGATTTGT

ATTACTTGACTATGAATAACAAGCACTGGCTGGTTCACAAGGAGTGGTTC

CACGACATTCCATTACCTTGGCACGCTGGGCAGACACCGGAACTCCACA

CTGGAACAACAAAGAAGCACTGGTAGAGTTCAAGGACGCACATGCCAAAA

GGCAAACTGTCGTGGTTCTAGGGAGTCAAGAAGGAGCAGTTCACACGGCC

CTTGCTGGAGCTCTGGAGGCTGAGATGGATGGTGCAAAGGGAAGGCTGTC

CTCTGGCCACTTGAAATGTCGCCTGAAAATGGATAAACTTAGATTGAAGG

GCGTGTCATACTCCTTGTGTACTGCAGCGTTCACATTCACCAAGATCCCG

GCTGAAACACTGCACGGGACAGTCACAGTGGAGGTACAGTACGCAGGGAC

AGATGGACCTTGCAAGGTTCCAGCTCAGATGGCGGTGGACATGCAAACTC

TGACCCCAGTTGGGAGGTTGATAACCGCTAACCCCGTAATCACTGAAAGC

ACTGAGAACTCTAAGATGATGCTGGAACTTGATCCACCATTTGGGGACTC

TTACATTGTCATAGGAGTCGGGGAGAAGAAGATCACCCACCACTGGCACA

GGAGTGGCAGCACCATTGGAAAAGCATTTGAAGCCACTGTGAGAGGTGCC

AAGAGAATGGCAGTCTTGGGAGACACAGCCTGGGACTTTGGATCAGTTGG

AGGCGCTCTCAACTCATTGGGCAAGGGCATCCATCAAATCTTTGGAGCAG

CTTTCAAATCTTTTTTCTTTATCATAGGGTTAATCATTGGACTATTCTTG

GTTCTCCGAGTTGGTATCCATCTTTGCATTAAATTAAAGCACACCAAGAA

AAGACAGATTTATACAGACATAGAGATGAACCGACTTGGAAAGTAA

SEQ ID NO: 12 is a Codon Optimized
ZIKV EG Nucleotide Sequence
ATGCTGCGGATCATCAATGCCAGAAAGGAGAAGAAGCGGAGAGGAGCCGA

CACCAGCGTGGGAATCGTGGGCCTGCTGCTGACCACAGCCATGGCCATCC

GGTGCATCGGCGTGTCTAACAGAGACTTTGTGGAGGGAATGAGCGGAGGC

ACCTGGGTGGATGTGGTGCTGGAGCACGGCGGCTGCGTGACAGTGATGGC
CCAGGACAAGCCTACCGTGGACATCGAGCTGGTGACCACAACCGTGTCTA
ATATGGCCGAGGTGCGGAGCTACTGCTATGAGGCCTCTATCAGCGACATG
GCCTCCGACAGCCGGTGTCCAACCCAGGGAGAGGCATACCTGGACAAGCA
GAGCGATACACAGTACGTGTGCAAGAGGACCCTGGTGGATCGCGGCTGGG
GCAATGGCTGTGGCCTGTTTGGCAAGGGCTCCCTGGTGACATGCGCCAAG
TTCGCCTGTTCCAAGAAGATGACCGGCAAGTCTATCCAGCCAGAGAACCT
GGAGTACAGGATCATGCTGTCTGTGCACGGCTCCCAGCACTCTGGCATGA
TCGTGAACGACACAGGCCACGAGACAGATGAGAATAGGGCCAAGGTGGAG
ATCACACCTAACTCCCCACGCGCCGAGGCCACCCTGGGCGGATTTGGCTC
TCTGGGCCTGGACTGCGAGCCCAGAACAGGCCTGGACTTCAGCGATCTGT
ACTATCTGACCATGAACAATAAGCACTGGCTGGTGCACAAGGAGTGGTTT
CACGACATCCCACTGCCATGGCACGCAGGAGCCGATACAGGCACCCCTCA
CTGGAACAATAAGGAGGCCCTGGTGGAGTTCAAGGATGCCCACGCCAAGA
GGCAGACAGTGGTGGTGCTGGGCTCCCAGGAGGGAGCCGTGCACACCGCC
CTGGCCGGGGCCCTGGAGGCAGAGATGGACGGAGCCAAGGGCCGCCTGAG
CTCCGGACACCTGAAGTGCAGGCTGAAGATGGATAAGCTGCGCCTGAAGG
GCGTGAGCTACTCCCTGTGCACAGCCGCCTTTACATTCACCAAGATCCCC
GCCGAGACACTGCACGGCACAGTGACCGTGGAGGTGCAGTATGCAGGCAC
AGACGGACCATGCAAGGTGCCTGCACAGATGGCCGTGGATATGCAGACAC
TGACCCCAGTGGGCCGGCTGATCACCGCAAATCCCGTGATCACAGAGAGC
ACCGAGAACTCCAAGATGATGCTGGAGCTGGACCCCCCTTTTGGCGATTC
CTACATCGTGATCGGCGTGGGCGAGAAGAAGATCACACACCACTGGCACA
GATCTGGCAGCACAATCGGCAAGGCCTTTGAGGCAACCGTGAGGGGAGCC
AAGAGGATGGCCGTGCTGGGCGACACCGCATGGGATTTCGGCAGCGTGGG
AGGGGCACTGAACAGCCTGGGGAAGGGCATCCACCAGATCTTTGGAGCCG
CCTTCAAGTCTTTCTTTTTCATCATCGGCCTGATCATCGGCCTGTTCCTG
GTGCTGCGGGTGGGCATCCACCTGTGCATCAAGCTGAAGCACACAAAGAA
GCGGCAGATCTATACCGACATCGAGATGAACAGACTGGGCAAGTGA

SEQ ID NO: 13 is a ZIKV prME156
amino acid sequence
MLRIINARKEKKRRGADTSVGIVGLLLTTAMAAEVTRRGSAYYMYLDRND
AGEAISFPTTLGMNKCYIQIMDLGHTCDATMSYECPMLDEGVEPDDVDCW
CNTTSTWVVYGTCHHKKGEARRSRRAVTLPSHSTRKLQTRSQTWLESREY
TKHLIRVENWIFRNPGFALAAAAIAWLLGSSTSQKVIYLVMILLIAPAYS
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDIGHETDENRAKVEITPNSPRAEATLGGFGSLGLDCEPRTGLDFSD
LYYLTMNNKHWLVHKEWFHDIPLPWHAGADTGTPHWNNKEALVEFKDAHA KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNAKNGSISLMCLALGGVLIFLST
AVSA SEQ ID NO: 14 is a ZIKV prME156
Nucleotide Sequence
ATGCTGAGAATAATCAATGCTAGGAAGGAGAAGAAGAGACGAGGCGCAGA
TACTAGTGTCGGAATTGTTGGCCTCCTGCTGACCACAGCTATGGCAGCGG
AGGTCACTAGACGTGGGAGTGCATACTATATGTACTTGGACAGAAACGAT
GCTGGGGAGGCCATATCTTTTCCAACCACATTGGGGATGAATAAGTGTTA
TATACAGATCATGGATCTTGGACACACGTGTGATGCCACCATGAGCTATG
AATGCCCTATGCTGGATGAGGGGGTGGAACCAGATGACGTCGATTGTTGG
TGCAACACGACGTCAACTTGGGTTGTGTACGGAACCTGCCATCACAAAAA
AGGTGAAGCACGGAGATCTAGAAGAGCTGTGACGCTCCCCTCCCATTCCA
CTAGGAAGCTGCAAACGCGGTCGCAAACCTGGTTGGAATCAAGAGAATAC
ACAAAGCACTTGATTAGAGTCGAAAATTGGATATTCAGGAACCCTGGCTT
CGCGTTAGCAGCAGCTGCCATCGCTTGGCTTTTGGGAAGCTCAACGAGCC
AAAAAGTCATATACTTGGTCATGATACTGCTGATTGCCCCGGCATACAGC
ATCAGGTGCATAGGAGTCAGCAATAGGGACTTTGTGGAAGGTATGTCAGG
TGGGACTTGGGTTGATGTTGTCTTGGAACATGGAGGTTGTGTCACTGTAA
TGGCACAGGACAAACCGACTGTACATAGAGCTGGTTACAACAACAGTCAG
CAACATGGCGGAGGTAAGATCCTACTGCTATGAGGCATCAATATCAGACA
TGGCTTCGGACAGCCGCTGCCCAACACAAGGTGAAGCCTACCTTGACAAG
CAATCAGACACTCAATATGTCTGCAAAAGAACGTTAGTGGACAGAGGCTG
GGGAAATGGATGTGGACTTTTTGGCAAAGGGAGCCTGGTGACATGCGCTA
AGTTTGCATGCTCCAAGAAAATGACCGGGAAGAGCATCCAGCCAGAGAAT
CTGGAGTACCGGATAATGCTGTCAGTTCATGGCTCCCAGCACAGTGGGAT
GATCGTTAATGACATTGGACATGAAACTGATGAGAATAGAGCGAAAGTTG
AGATAACGCCCAATTCACCAAGAGCCGAAGCCACCCTGGGGGGGTTTGGA
AGCCTAGGACTTGATTGTGAACCGAGGACAGGCCTTGACTTTTCAGATTT
GTATTACTTGACTATGAATAACAAGCACTGGCTGGTTCACAAGGAGTGGT
TCCACGACATTCCATTACCTTGGCACGCTGGGGCAGACACCGGAACTCCA
CACTGGAACAACAAAGAAGCACTGGTAGAGTTCAAGGACGCACATGCCAA
AAGGCAAACTGTCGTGGTTCTAGGGAGTCAAGAAGGAGCAGTTCACACGG
CCCTTGCTGGAGCTCTGGAGGCTGAGATGGATGGTGCAAAGGGAAGGCTG
TCCTCTGGCCACTTGAAATGTCGCCTGAAAATGGATAAACTTAGATTGAA
GGGCGTGTCATACTCCTTGTGTACTGCAGCGTTCACATTCACCAAGATCC
CGGCTGAAACACTGCACGGGACAGTCACAGTGGAGGTACAGTACGCAGGG ACAGATGGACCTTGCAAGGTTCCAGCTCAGATGGCGGTGGACATGCAAAC
TCTGACCCCAGTTGGGAGGTTGATAACCGCTAACCCCGTAATCACTGAAA
GCACTGAGAACTCTAAGATGATGCTGGAACTTGATCCACCATTTGGGGAC
TCTTACATTGTCATAGGAGTCGGGGAGAAGAAGATCACCCACCACTGGCA
CAGGAGTGGCAGCACCATTGGAAAAGCATTTGAAGCCACTGTGAGAGGTG
CCAAGAGAATGGCAGTCTTGGGAGACACAGCCTGGGACTTTGGATCAGTT
GGAGGCGCTCTCAACTCATTGGGCAAGGGCATCCATCAAATCTTTGGAGC
AGCTTTCAAATCATTGTTTGGAGGAATGTCCTGGTTCTCACAAATTCTCA
TTGGAACGTTGCTGATGTGGTTGGGTCTGAACGCAAAGAATGGATCTATT
TCCCTTATGTGCTTGGCCTTAGGGGGAGTGTTGATCTTCTTATCCACAGC
CGTCTCTGCTTAA SEQ ID NO: 15 is a Codon Optimized ZIKV prME156
Nucleotide Sequence
ATGCTGAGGATCATCAATGCCCGCAAGGAGAAGAAGCGGAGAGGAGCCGAC
ACAAGCGTGGGCATCGTGGGCCTGCTGCTGACCACAGCAATGGCCGCCGAG
GTGACCAGGAGGGGCAGCGCCTACTATATGTACCTGGACCGGAATGATGCC
GGCGAGGCCATCTCCTTTCCCACCACACTGGGCATGAACAAGTGCTACATC
CAGATCATGGACCTGGGCCACACATGCGATGCCACCATGTCCTATGAGTGT
CCAATGCTGGACGAGGGCGTGGAGCCCGACGATGTGGATTGCTGGTGTAAC
ACCACATCTACATGGGTGGTGTACGGCACCTGTCACCACAAGAAGGGAGAG
GCCCGGCGGAGCCGGCGGGCCGTGACACTGCCTTCCCACTCTACCCGGAAG
CTGCAGACAAGAAGCCAGACCTGGCTGGAGTCCCGGGAGTATACCAAGCAC
CTGATCCGGGTGGAGAACTGGATCTTTAGAAATCCAGGATTCGCCCTGGCC
GCCGCCGCCATCGCATGGCTGCTGGGCAGCTCCACCAGCCAGAAAGTGATC
TACCTGGTCATGATCCTGCTGATCGCCCCTGCCTATTCTATCAGGTGCATC
GGCGTGAGCAACCGGGACTTCGTGGAGGGAATGTCCGGAGGCACCTGGGTG
GATGTGGTGCTGGAGCACGGCGGCTGCGTGACAGTGATGGCCCAGGACAAG
CCAACCGTGGACATCGAGCTGGTGACCACAACCGTGTCCAACATGGCCGAG
GTGCGGTCTTACTGCTATGAGGCCAGCATCTCCGACATGGCCTCTGATAGC
AGATGTCCCACCCAGGGCGAGGCCTACCTGGACAAGCAGTCCGATACACAG
TACGTGTGCAAGAGGACCCTGGTGGACAGGGGATGGGGAAATGGATGTGGC
CTGTTTGGCAAGGGCTCTCTGGTGACATGCGCCAAGTTCGCCTGTAGCAAG
AAGATGACCGGCAAGTCCATCCAGCCAGAAACCTGGAGTACAGGATCATG
CTGTCTGTGCACGGCTCCCAGCACTCTGGCATGATCGTGAACGACATTGGC
CACGAGACAGATGAGAATAGGGCCAAGGTGGAGATACACACCTAACTCCCCA
CGCGCCGAGGCCACCCTGGGCGGATTTGGCTCTCTGGGCCTGGACTGCGAG
CCTCGCACAGGCCTGGACTTCTCCGATCTGTACTATCTGACCATGAACAAT
AAGCACTGGCTGGTGCACAAGGAGTGGTTTCACGACATCCCACTGCCATGG
CACGCAGGAGCCGATACAGGCACCCCACACTGGAACAATAAGGAGGCCCTG
GTGGAGTTCAAGGATGCCCACGCCAAGAGGCAGACAGTGGTGGTGCTGGGC AGCCAGGAGGGAGCCGTGCACACCGCCCTGGCCGGGGCCCTGGAGGCAGAG
ATGGACGGAGCCAAGGGCCGCCTGTCTAGCGGACACCTGAAGTGCCGGCTG
AAGATGGATAAGCTGAGACTGAAGGGCGTGTCCTACTCTCTGTGCACCGCC
GCCTTCACCTTCACCAAGATCCCCGCCGAGACACTGCACGGCACAGTGACC
GTGGAGGTGCAGTATGCCGGCACAGACGGCCCCCTGTAAGGTGCCTGCCCAG
ATGGCCGTGGATATGCAGACACTGACCCCTGTGGGCCGGCTGATCACCGCA
AATCCAGTGATCACAGAGTCTACCGAGAACAGCAAGATGATGCTGGAGCTG
GACCCCCCTTTTGGCGATAGCTATATCGTGATCGGCGTGGGCGAGAAGAAG
ATCACACACCACTGGCACAGAAGCGGCTCCACAATCGGCAAGGCCTTTGAG
GCAACCGTGCGGGGAGCCAAGAGAATGGCCGTGCTGGGCGACACCGCATGG
GATTTCGGCTCTGTGGGAGGGGCACTGAACAGCCTGGGGAAGGGCATCCAC
CAGATCTTCGGAGCCGCCTTTAAGTCCCTGTTCGGCGGCATGAGCTGGTTT
TCCCAGATCCTGATCGGCACCCTGCTGATGTGGCTGGGCCTGAACGCCAAG
AATGGCTCTATCAGCCTGATGTGCCTGGCCCTGGGCGGCGTGCTGATCTTC
CTGTCCACCGCCGTGTCTGCCTGA SEQ ID NO: 16 is a GAG/NSI amino acid sequence
MGQTVTTPLSLTLGHWKDVERIAHNQSVDVKKRRWVTFCSAEWPTFNVGWP
RDGTFNRDLITQVKIKVFSPGPHGHPDQVPYIVTWEALAFDPPPWVKPFVH
PKPPPPLPPSAPSLPLEPPRSTPPRSSLYPALTPSLGAKPKPQVLSDSGGP
LIDLLTEDPPPYRDPRPPPSDRDGNGGEATPAGEAPDPSPMASRLRGRREP
PVADSTTSQAFPLRAGGNGQLQYWPFSSSDLYNWKNNNPSFSEDPGKLTAL
IESVLITHQPTWDDCQQLLGTLLTGEEKQRVLLEARKAVRGDDGRPTQLPN
EVDAAFPLERPDWDYTTQAGRNHLVHYRQLLLAGLQNAGRSPTNLAKVKGI
TQGPNESPSAFLERLKEAYRRYTPYDPEDPGQETNVSMSFIWQSAPDIGRK
LERLEDLKNKTLGDLVREAEKIFNKRETPEEREERIRRETEEKEERRRTED
EQKEKERDRRRHREMSKLLATVVSGQKQDRQGGERRRSQLDRDQCAYCKEK
GHWAKDCPKKPRGPRGPRPQTSLLTLDD<u>VGCSVDFSKKETRCGTGVFVYND
VEAWRDRYKYHPDSPRRLAAAVKQAWEDGICGISSVSRMENIMWRSVEGEL
NAILEENGVQLTVVVGSVKNPMWRGPQRLPVPVNELPHGWKAWGKSYFVRA
AKTNNSFVVDGDTLKECPLKHRAWNSFLVEDHGFGVFHTSVWLKVREDYSL
ECDPAVIGTAVKGKEAVHSDLGYWIESEKNDTWRLKRAHLIEMKTCEWPKS
HTLWTDGIEESDLIIPKSLAGPLSHHNTREGYRTQMKGPWHSEELEIRFEE
CPGTKVHVEETCGTRGPSLRSTTASGRVIEEWCCRECTMPPLSFRAKDGCW
YGMEIRPRKEPESNLVRSMVTAGS</u>

SEQ ID NO: 17 is a GAG/NSI Nucleotide Sequence
ATGGGACAGACCGTCACAACACCCCTGAGCCTGACCCTGGGACATTGGAAA
GACGTGGAGAGGATCGCACATAACCAGAGCGTGGACGTGAAGAAACGGAGA
TGGGTCACATTCTGCAGTGCTGAGTGGCCAACTTTTAATGTGGGATGGCCC
CGAGACGGCACTTTCAACAGGGATCTGATCACCCAGGTGAAGATCAAGGTC -continued TTTAGCCCAGGACCTCACGGACATCCAGACCAGGTGCCTTATATCGTCACC
TGGGAGGCACTGGCCTTCGATCCCCCTCCATGGGTGAAGCCATTTGTCCAC
CCAAAACCACCTCCACCACTGCCTCCAAGTGCCCCTTCACTGCCACTGGAA
CCACCCCGGAGCACACCACCCCGCAGCTCCCTGTATCCTGCTCTGACTCCA
TCTCTGGGCGCAAAGCCAAAACCACAGGTGCTGAGCGACTCCGGAGGACCA
CTGATTGACCTGCTGACAGAGGACCCCCCACCATACCGAGATCCTCGGCCT
CCACCAAGCGACCGCGATGGAAATGGAGGAGAGGCTACTCCTGCCGGCGAA
GCCCCTGACCCATCTCCAATGGCTAGTAGGCTGCGCGGCAGGCGCGAGCCT
CCAGTGGCAGATAGCACCACATCCCAGGCCTTCCCTCTGAGGGCTGGGGA
AATGGGCAGCTCCAGTATTGGCCATTTTCTAGTTCAGACCTGTACAACTGG
AAGAACAATAACCCCTCTTTCAGTGAGGACCCCGGCAAACTGACCGCCCTG
ATCGAATCCGTGCTGATTACCCATCAGCCCACATGGGACGATTGTCAGCAG
CTCCTGGGCACCCTGCTGACCGGAGAGGAAAAGCAGCGCGTGCTGCTGGAG
GCTCGCAAAGCAGTCCGAGGGGACGATGGACGGCCCACACAGCTCCCTAAT
GAGGTGGACGCCGCTTTTCCACTGGAAAGACCCGACTGGGATTATACTACC
CAGGCAGGGAGAAACCACCTGGTCCATTACAGGCAGCTCCTGCTGGCAGGC
CTGCAGAATGCCGGGAGATCCCCCACCAACCTGGCCAAGGTGAAAGGCATC
ACACAGGGGCCTAATGAGTCACCAAGCGCCTTTCTGGAGAGGCTGAAGGAA
GCTTACCGACGGTATACCCCATACGACCCTGAGGACCCCGGACAGGAAACA
AACGTCTCCATGTCTTTCATCTGGCAGTCTGCCCCAGACATTGGGCGGAAG
CTGGAGAGACTGGAAGACCTGAAGAACAAGACCCTGGGCGACCTGGTGCGG
GAGGCTGAAAAGATCTTCAACAAACGGGAGACCCCCGAGGAAAGAGAGGAA
AGGATTAGAAGGGAAACTGAGGAAAAGGAGGAACGCCGACGGACCGAGGAC
GAACAGAAGGAGAAAGAACGAGATCGGCGGCGGCACCGGGAGATGTCAAAG
CTGCTGGCCACCGTGGTCAGCGGACAGAAACAGGACAGACAGGGAGGAGAG
CGACGGAGAAGCCAGCTCGACAGGGATCAGTGCGCATACTGTAAGGAAAAA
GGCCATTGGGCCAAGGATTGCCCCAAAAAGCCAAGAGGACCAAGAGGACCA
AGACCACAGACATCACTGCTGACCCTGGACGACGTGGGGTGCTCGGTGGAC
TTCTCAAAGAAGGAGACGAGATGCGGTACAGGGGTGTTCGTCTATAACGAC
GTTGAAGCCTGGAGGGACAGGTACAAGTACCATCCTGACTCCCCCCGTAGA
TTGGCAGCAGCAGTCAAGCAAGCCTGGGAAGATGGTATCTGCGGGATCTCC
TCTGTTTCAAGAATGGAAAACATCATGTGGAGATCAGTAGAAGGGGAGCTC
AACGCAATCCTGGAAGAGAATGGAGTTCAACTGACGGTCGTTGTGGGATCT
GTAAAAAACCCCATGTGGAGAGGTCCACAGAGATTGCCCGTGCCTGTGAAC
GAGCTGCCCCACGCTGGAAGGCTTGGGGGAAATCGTACTTCGTCAGAGCA
GCAAAGACAAATAACAGCTTTGTCGTGGATGGTGACACACTGAAGGAATGC
CCACTCAAACATAGAGCATGGAACAGCTTTCTTGTGGAGGATCATGGGTTC
GGGGTATTTCACACTAGTGTCTGGCTCAAGGTTAGAGAAGATTATTCATTA
GAGTGTGATCCAGCCGTTATTGGAACAGCTGTTAAGGGAAAGGAGGCTGTA
CACAGTGATCTAGGCTACTGGATTGAGAGTGAGAAGAATGACACATGGAGG -continued CTGAAGAGGGCCCATCTGATCGAGATGAAAACATGTGAATGGCCAAAGTCC
CACACATTGTGGACAGATGGAATAGAAGAGAGTGATCTGATCATACCCAAG
TCTTTAGCTGGGCCACTCAGCCATCACAATACCAGAGAGGGCTACAGGACC
CAAATGAAAGGGCCATGGCACAGTGAAGAGCTTGAAATTCGGTTTGAGGAA
TGCCCAGGCACTAAGGTCCACGTGGAGGAAACATGTGGAACGAGAGGACCA
TCTCTGAGATCAACCACTGCAAGCGGAAGGGTGATCGAGGAATGGTGCTGC
AGGGAGTGCACAATGCCCCCACTGTCGTTCCGGGCTAAAGATGGCTGTTGG
TATGGAATGGAGATAAGGCCCAGGAAAGAACCAGAAAGCAACTTAGTAAGG
TCAATGGTGACTGCAGGATCATAA SEQ ID NO: 18 is a Codon Optimized GAG/NS1
Nucleotide Sequence
ATGGGACAGACCGTGACAACACCCCTGAGCCTGACACTGGGACATTGGAAG
GACGTGGAGCGCATCGCACATAACCAGAGCGTGGACGTGAAGAAGCGGAGA
TGGGTGACCTTCTGCTCCGCCGAGTGGCCCACCTTCAACGTGGGATGGCCC
CGGGACGGCACCTTCAACAGAGATCTGATCACACAGGTGAAGATCAAGGTG
TTTTCTCCAGGACCACACGGACACCCAGACCAGGTGCCCTATATCGTGACC
TGGGAGGCCCTGGCCTTCGATCCACCTCCATGGGTGAAGCCTTTTGTGCAC
CCAAAGCCACCTCCACCACTGCCTCCAAGCGCCCCTTCCCTGCCACTGGAG
CCACCTCGGAGCACCCCACCCAGAAGCTCCCTGTATCCCGCCCTGACACCT
AGCCTGGGGGCCAAGCCTAAGCCACAGGTGCTGTCCGACTCTGGAGGACCA
CTGATCGACCTGCTGACCGAGGACCCCCCACCATACCGCGATCCCCGGCCT
CCACCATCCGACCGGGATGGAAATGGAGGAGAGGCAACACCTGCCGGCGAG
GCCCCCGACCCTAGCCCAATGGCCTCCCGCCTGCGGGGCAGGCGCGAGCCT
CCAGTGGCCGATTCTACCACAAGCCAGGCATTCCCTCTGAGAGCAGGAGGA
AATGGCCAGCTCCAGTATTGGCCATTTTCTAGCTCCGACCTGTACAACTGG
AAGAACAATAACCCTAGCTTCTCCGAGGACCCCGGCAAGCTGACCGCCCTG
ATCGAGAGCGTGCTGATCACCCACCAGCCCACATGGGACGATTGTCAGCAG
CTCCTGGGCACCCTGCTGACCGGAGAGGAGAAGCAGAGGGTGCTGCTGGAG
GCAAGGAAGGCCGTGAGAGGCGACGATGGCCGCCCAACCCAGCTCCCAAAT
GAGGTGGATGCCGCCTTTCCTCTGGAGCGGCCAGACTGGGATTATACCACA
CAGGCCGGCAGAAACCACCTGGTGCACTACAGACAGCTCCTGCTGGCCGGC
CTGCAGAATGCCGGCAGAAGCCCCACCAACCTGGCCAAGGTGAAGGGCATC
ACACAGGGCCCAATGAGTCTCCTAGCGCCTTTCTGGAGCGCCTGAAGGAG
GCCTACCGGAGATATACCCCATACGACCCTGAGGACCCCGGACAGGAGACA
AACGTGTCCATGTCTTTCATCTGGCAGAGCCCCCCGACATCGGCAGGAAG
CTGGAGCGCCTGGAGGACCTGAAGAATAAGACCCTGGGCGATCTGGTGAGG
GAGGCCGAGAAGATCTTCAACAAGCGCGAGACACCTGAGGAGAGAGAGGAG
CGGATCAGACGGGAGACAGAGGAGAAGGAGGAGCGGAGAAGGACAGAGGAC
GAGCAGAAGGAGAAGGAGAGGGATCGCCGGAGACACCGCGAGATGAGCAAG
CTGCTGGCCACCGTGGTGTCCGGACAGAAGCAGGACAGGCAGGGAGGAGAG

```
CGGCGGCGGAGCCAGCTCGACAGAGATCAGTGCGCCTATTGTAAGGAGAAG
GGCCACTGGGCCAAGGATTGCCCCAAGAAGCCTCGCGGCCCACGGGGCCCC
AGACCTCAGACCTCCCTGCTGACACTGGACGATGTGGGCTGCTCTGTGGAC
TTCAGCAAGAAGGAGACAAGATGTGGCACAGGCGTGTTCGTGTACAATGAC
GTGGAGGCCTGGAGAGATAGGTACAAGTATCACCCAGACTCCCCCCGGCGG
CTGGCCGCCGCCGTGAAGCAGGCCTGGGAGGATGGCATCTGTGGCATCTCT
AGCGTGTCCAGGATGGAGAACATCATGTGGCGCTCTGTGGAGGGCGAGCTG
AATGCCATCCTGGAGGAGAACGGAGTGCAGCTCACCGTGGTGGTGGGCAGC
GTGAAGAATCCAATGTGGAGGGGACCACAGAGACTGCCAGTGCCCGTGAAC
GAGCTGCCTCACGGATGGAAGGCATGGGGCAAGTCTTACTTCGTGCGGGCC
GCCAAGACCAATAACAGCTTTGTGGTGGACGGCGATACACTGAAGGAGTGC
CCACTGAAGCACAGAGCCTGGAACTCCTTCCTGGTGGAGGACCACGGCTTC
GGCGTGTTTCACACCAGCGTGTGGCTGAAGGTGAGAGAGGACTATTCCCTG
GAGTGTGATCCAGCCGTGATCGGCACAGCCGTGAAGGGCAAGGAGGCCGTG
CACTCTGACCTGGGCTACTGGATCGAGAGCGAGAAGAATGATACCTGGAGG
CTGAAGCGCGCCCACCTGATCGAGATGAAGACATGCGAGTGGCCTAAGTCC
CACACCCTGTGGACAGACGGCATCGAGGAGTCTGATCTGATCATCCCCAAG
TCCCTGGCCGGCCCTCTGTCTCACCACAACACCAGGGAGGGCTATCGCACA
CAGATGAAGGGCCCCTGGCACAGCGAGGAGCTGGAGATCAGGTTTGAGGAG
TGCCCTGGCACCAAGGTGCATGTGGAGGAGACATGTGGCACAAGGGGCCCA
TCCCTGCGCTCTACCACAGCCAGCGGCAGAGTGATCGAGGAGTGGTGCTGT
AGAGAGTGCACAATGCCACCTCTGAGCTTCCGCGCAAAGGACGGCTGTTGG
TACGGCATGGAGATCCGCCCTAGAAAAGAGCCCGAGAGCAATCTGGTCAGG
TCAATGGTCACCGCTGGGTCCTAA

SEQ ID NO: 19 is a GAG/ΔNSI amino acid sequence
MGQTVTTPLSLTLGHWKDVERIAHNQSVDVKKRRWVTFCSAEWPTFNVGW
PRDGTFNRDLITQVKIKVFSPGPHGHPDQVPYIVTWEALAFDPPPWVKPF
VHPKPPPPLPPSAPSLPLEPPRSTPPRSSLYPALTPSLGAKPKPQVLSDS
GGPLIDLLTEDPPPYRDPRPPPSDRDGNGGEATPAGEAPDPSPMASRLRG
RREPPVADSTTSQAFPLRAGGNGQLQYWPFSSSDLYNWKNNNPSFSEDPG
KLTALIESVLITHQPTWDDCQQLLGTLLTGEEKQRVLLEARKAVRGDDGR
PTQLPNEVDAAFPLERPDWDYTTQAGRNHLVHYRQLLLAGLQNAGRSPTN
LAKVKGITQGPNESPSAFLERLKEAYRRYTPYDPEDPGQETNVSMSFIWQ
SAPDIGRKLERLEDLKNKTLGDLVREAEKIFNKRETPEEREERIRRETEE
KEERRRTEDEQKEKERDRRRHREMSKLLATVVSGQKQDRQGGERRRSQLD
RDQCAYCKEKGHWAKDCPKKPRGPRGPRPQTSLLTLDDD<u>PAVIGTAVKG</u>
<u>EAVHSDLGYWIESEKNDTWRLKRAHLIEMKTCEWPKSHTLWTDGIEESDL</u>
<u>IIPKSLAGPLSHHNTREGYRTQMKGPWHSEELEIRFEECPGTKVHVEETC</u>
<u>GTRGPSLRSTTASGRVIEEWCCRECTMPPLSFRAKDGCWYGMEIRPRKEP</u>
<u>ESNLVRSMVTAGS</u>

SEQ ID NO: 20 is a GAG/ΔNSI Nucleotide Sequence
ATGGGACAGACCGTCACAACACCCCTGAGCCTGACCCTGGGACATTGGAA
AGACGTGGAGAGGATCGCACATAACCAGAGCGTGGACGTGAAGAAACGGA
GATGGGTCACATTCTGCAGTGCTGAGTGGCCAACTTTTAATGTGGGATGG
CCCCGAGACGGCACTTTCAACAGGGATCTGATCACCCAGGTGAAGATCAA
GGTCTTTAGCCCAGGACCTCACGGACATCCAGACCAGGTGCCTTATATCG
TCACCTGGGAGGCACTGGCCTTCGATCCCCCTCCATGGGTGAAGCCATTT
GTCCACCCAAAACCACCTCCACCACTGCCTCCAAGTGCCCCTTCACTGCC
ACTGGAACCACCCCGGAGCACACCACCCCGCAGCTCCCTGTATCCTGCTC
TGACTCCATCTCTGGGCGCAAAGCCAAAACCACAGGTGCTGAGCGACTCC
GGAGGACCACTGATTGACCTGCTGACAGAGGACCCCCCACCATACCGAGA
TCCTCGGCCTCCACCAAGCGACCGCGATGGAAATGGAGGAGAGGCTACTC
CTGCCGGCGAAGCCCCTGACCCATCTCCAATGGCTAGTAGGCTGCGCGGC
AGGCGCGAGCCTCCAGTGGCAGATAGCACCACATCCCAGGCCTTCCCTCT
GAGGGCTGGGGGAAATGGGCAGCTCCAGTATTGGCCATTTTCTAGTTCAG
ACCTGTACAACTGGAAGAACAATAACCCCTCTTTCAGTGAGGACCCCGGC
AAACTGACCGCCCTGATCGAATCCGTGCTGATTACCCATCAGCCCACATG
GGACGATTGTCAGCAGCTCCTGGGCACCCTGCTGACCGGAGAGGAAAAGC
AGCGCGTGCTGCTGGAGGCTCGCAAAGCAGTCCGAGGGGACGATGGACGG
CCCACACAGCTCCCTAATGAGGTGGACGCCGCTTTTCCACTGGAAAGACC
CGACTGGGATTATACTACCCAGGCAGGGAGAAACCACCTGGTCCATTACA
GGCAGCTCCTGCTGGCAGGCCTGCAGAATGCCGGAGATCCCCCACCCAAC
CTGGCCAAGGTGAAAGGCATCACACAGGGGCCTAATGAGTCACCAAGCGC
CTTTCTGGAGAGGCTGAAGGAAGCTTACCGACGGTATACCCCATACGACC
CTGAGGACCCCGGACAGGAAACAAACGTCTCCATGTCTTTCATCTGGCAG
TCTGCCCCAGACATTGGGCGGAAGCTGGAGAGACTGGAAGACCTGAAGAA
CAAGACCCTGGGCGACCTGGTGCGGGAGGCTGAAAAGATCTTCAACAAAC
GGGAGACCCCCGAGGAAAGAGAGGAAAGGATTAGAAGGGAAACTGAGGAA
AAGGAGGAACGCCGACGGACCGAGGACGAACAGAAGGAGAAAGAACGAGA
TCGGCGGCGGCACCGGGAGATGTCAAAGCTGCTGGCCACCGTGGTCAGCG
GACAGAAACAGGACAGACAGGGAGGAGAGCGACGGAGAAGCCAGCTCGAC
AGGGATCAGTGCGCATACTGTAAGGAAAAGGCCATTGGGCCAAGGATTG
CCCCAAAAAGCCAAGAGGACCAAGAGGACCAAGACCACAGACATCACTGC
TGACCCTGGACGACGATCCAGCCGTTATTGGAACAGCTGTTAAGGGAAAG
GAGGCTGTACACAGTGATCTAGGCTACTGGATTGAGAGTGAGAAGAATGA
CACATGGAGGCTGAAGAGGGCCCATCTGATCGAGATGAAAACATGTGAAT
GGCCAAAGTCCCACACATTGTGGACAGATGGAATAGAAGAGAGTGATCTG
ATCATACCCAAGTCTTTAGCTGGGCCACTCAGCCATCACAATACCAGAGA
GGGCTACAGGACCCAAATGAAAGGGCCATGGCACAGTGAAGAGCTTGAAA
TTCGGTTTGAGGAATGCCCAGGCACTAAGGTCCACGTGGAGGAAACATGT
GGAACGAGAGGACCATCTCTGAGATCAACCACTGCAAGCGGAAGGGTGAT
```

SEQ ID NO: 21 is a GAG/ΔNSI* amino acid sequence
MGQTVTTPLSLTLGHWKDVERIAHNQSVDVKKRRWVTFCSAEWPTFNVGW
PRDGTFNRDLITQVKIKVFSPGPHGHPDQVPYIVTWEALAFDPPPWVKPF
VHPKPPPPLPPSAPSLPLEPPRSTPPRSSLYPALTPSLGAKPKPQVLSDS
GGPLIDLLTEDPPPYRDPRPPPSDRDGNGGEATPAGEAPDPSPMASRLRG
RREPPVADSTTSQAFPLRAGGNGQLQYWPFSSSDLYNWKNNNPSFSEDPG
KLTALIESVLITHQPTWDDCQQLLGTLLTGEEKQRVLLEARKAVRGDDGR
PTQLPNEVDAAFPLERPDWDYTTQAGRNHLVHYRQLLLAGLQNAGRSPTN
LAKVKGITQGPNESPSAFLERLKEAYRRYTPYDPEDPGQETNVSMSFIWQ
SAPDIGRKLERLEDLKNKTLGDLVREAEKIFNKRETPEEREERIRRETEE
KEERRRTEDEQKEKERDRRRHREMSKLLATVVSGQKQDRQGGERRRSQLD
RDQCAYCKEKGHWAKDCPKKPRGPRGPRPQTSLLTLDDD<u>PAVIGTAVKGK
EAVHSDLGYWIESEKNDTWRLKRAHLIEMKTCEWPKSHTLWTDGIEVSDL
IIPKSLAGPLSHHDTREGYRTQMKGPWHSEELEIRFEECPGTKVHVEETC
GTRGPSLRSTTASGRVIEEWCCRECTMPSLSFRAKDGCWYGVEIRPRKEP
ESNLVRSMVTAGS</u>

SEQ ID NO: 22 is a GAG/ΔNSI* Nucleotide Sequence
ATGGGACAGACCGTCACAACACCCCTGAGCCTGACCCTGGGACATTGGAAA
GACGTGGAGAGGATCGCACATAACCAGAGCGTGGACGTGAAGAAACGGAGA
TGGGTCACATTCTGCAGTGCTGAGTGGCCAACTTTTAATGTGGGATGGCCC
CGAGACGGCACTTTCAACAGGGATCTGATCACCCAGGTGAAGATCAAGGTC
TTTAGCCCAGGACCTCACGGACATCCAGACCAGGTGCCTTATATCGTCACC
TGGGAGGCACTGGCCTTCGATCCCCCTCCATGGGTGAAGCCATTTGTCCAC
CCAAAACCACCTCCACCACTGCCTCCAAGTGCCCCTTCACTGCCACTGGAA
CCACCCCGGAGCACACCACCCCGCAGCTCCCTGTATCCTGCTCTGACTCCA
TCTCTGGGCGCAAAGCCAAAACCACAGGTGCTGAGCGACTCCGGAGGACCA
CTGATTGACCTGCTGACAGAGGACCCCCCACCATACCGAGATCCTCGGCCT
CCACCAAGCGACCGCGATGGAAATGGAGGAGAGGCTACTCCTGCCGGCGAA
GCCCCTGACCCATCTCCAATGGCTAGTAGGCTGCGCGGCAGGCGCGAGCCT
CCAGTGGCAGATAGCACCACATCCCAGGCCTTCCCTCTGAGGGCTGGGGGA
AATGGGCAGCTCCAGTATTGGCCATTTTCTAGTTCAGACCTGTACAACTGG
AAGAACAATAACCCCTCTTTCAGTGAGGACCCCGGCAAACTGACCGCCCTG
ATCGAATCCGTGCTGATTACCCATCAGCCCACATGGGACGATTGTCAGCAG
CTCCTGGGCACCCTGCTGACCGGAGAGGAAAAGCAGCGCGTGCTGCTGGAG
GCTCGCAAAGCAGTCCGAGGGGACGATGGACGGCCCACACAGCTCCCTAAT
GAGGTGGACGCCGCTTTTCCACTGGAAAGACCCGACTGGGATTATACTACC
CAGGCAGGGAGAAACCACCTGGTCCATTACAGGCAGCTCCTGCTGGCAGGC
CTGCAGAATGCCGGGAGATCCCCCACCAACCTGGCCAAGGTGAAAGGCATC
ACACAGGGGCCTAATGAGTCACCAAGCGCCTTTCTGGAGAGGCTGAAGGAA
GCTTACCGACGGTATACCCCATACGACCCTGAGGACCCCGGACAGGAAACA
AACGTCTCCATGTCTTTCATCTGGCAGTCTGCCCCAGACATTGGGCGAAAG
CTGGAGAGACTGGAAGACCTGAAGAACAAGACCCTGGGCGACCTGGTGCGG
GAGGCTGAAAAGATCTTCAACAAACGGGAGACCCCCGAGGAAAGAGAGGAA
AGGATTAGAAGGGAAACTGAGGAAAAGGAGGAACGCCGACGGACCGAGGAC
GAACAGAAGGAGAAAGAACGAGATCGGCGGCGGCACCGGGAGATGTCAAAG
CTGCTGGCCACCGTGGTCAGCGGACAGAAACAGGACAGACAGGGAGGAGAG
CGACGGAGAAGCCAGCTCGACAGGGATCAGTGCGCATACTGTAAGGAAAAA
GGCCATTGGGCCAAGGATTGCCCCAAAAAGCCAAGAGGACCAAGAGGACCA
AGACCACAGACATCACTGCTGACCCTGGACGACGATCCAGCCGTTATTGGA
ACAGCTGTTAAGGGAAAGGAGGCTGTACACAGTGATCTAGGCTACTGGATT
GAGAGTGAGAAGAATGACACATGGAGGCTGAAGAGGGCCCATCTGATCGAG
ATGAAAACATGTGAATGGCCAAAGTCCCACACATTGTGGACAGATGGAATA
GAAGTTAGTGATCTGATCATACCCAAGTCTTTAGCTGGGCCACTCAGCCAT
CACGATACCAGAGAGGGCTACAGGACCCAAATGAAAGGGCCATGGCACAGT
GAAGAGCTTGAAATTCGGTTTGAGGAATGCCCAGGCACTAAGGTCCACGTG
GAGGAAACATGTGAACGAGAGGACCATCTCTGAGATCAACCACTGCAAGC
GGAAGGGTGATCGAGGAATGGTGCTGCAGGGAGTGCACAATGCCCTCTCTG
TCGTTCCGGGCTAAAGATGGCTGTTGGTATGGAGTTGAGATAAGGCCCAGG
AAAGAACCAGAAAGCAACTTAGTAAGGTCAATGGTGACTGCAGGATCATAA SEQ ID NO: 23 is a Propol II Vector including a
Codon Optimized Nucleotide Sequence of RSV-F
wild type
CTAGAGAGCTTGGCCCATTGCATACGTTGTATCCATATCATAATATGTAC
ATTTATATTGGCTCATGTCCAACATTACCGCCATGTTGACATTGATTATT
GACTAGTTATTAATAGTAATCAATTACGGGGTCATTAGTTCATAGCCCAT
ATATGGAGTTCCGCGTTACATAACTTACGGTAAATGGCCCGCCTGGCTGA
CCGCCCAACGACCCCCGCCCATTGACGTCAATAATGACGTATGTTCCCAT
AGTAACGCCAATAGGGACTTTCCATTGACGTCAATGGGTGGAGTATTTAC
GGTAAACTGCCCACTTGGCAGTACATCAAGTGTATCATATGCCAAGTACG
CCCCCTATTGACGTCAATGACGGTAAATGGCCCGCCTGGCATTATGCCCA
GTACATGACCTTATGGGACTTTCCTACTTGGCAGTACATCTACGTATTAG
TCATCGCTATTACCATGGTGATGCGGTTTTGGCAGTACATCAATGGGCGT
GGATAGCGGTTTGACTCACGGGGATTTCCAAGTCTCCACCCCATTGACGT
CAATGGGAGTTTGTTTTGGCACCAAAATCAACGGGACTTTCCAAAATGTC
GTAACAACTCCGCCCCATTGACGCAAATGGGCGGTAGGCGTGTACGGTGG
GAGGTCTATATAAGCAGAGCTCGTTTAGTGAACCGTCAGATCGCCTGGAG
ACGCCATCCACGCTGTTTTGACCTCCATAGAAGACACCGGGACCGATCCA

```
GCCTCCGGTCGACCGATCCTGAGAACTTCAGGGTGAGTTTGGGGACCCTT
GATTGTTCTTTCTTTTTCGCTATTGTAAAATTCATGTTATATGGAGGGGG
CAAAGTTTTCAGGGTGTTGTTTAGAATGGGAAGATGTCCCTTGTATCACC
ATGGACCCTCATGATAATTTTGTTTCTTTCACTTTCTACTCTGTTGACAA
CCATTGTCTCCTCTTATTTTCTTTTCATTTTCTTGTAACTTTTTCGTTAA
ACTTTAGCTTGCATTTGTAACGAATTTTTAAATTCACTTTTGTTTATTTG
TCAGATTGTAAGTACTTTCTCTAATCACTTTTTTTTCAAGGCAATCAGGG
TATATTATATTGTACTTCAGCACAGTTTTAGAGAACAATTGTTATAATTA
AATGATAAGGTAGAATATTTCTGCATATAAATTCTGGCTGGCGTGGAAAT
ATTCTTATTGGTAGAAACAACTACATCCTGGTCATCATCCTGCCTTTCTC
TTTATGGTTACAATGATATACACTGTTTGAGATGAGGATAAAATACTCTG
AGTCCAAACCGGGCCCCTCTGCTAACCATGTTCATGCCTTCTTCTTTTTC
CTACAGCTCCTGGGCAACGTGCTGGTTATTGTGCTGTCTCATCATTTTGG
CAAAGAATTCCTCGAGGTTTAAACGAATTCCGCCACCATGGAGTTGCTAA
TCCTCAAAGCAAATGCAATTACCACAATCCTCACTGCAGTCACATTTTGT
TTTGCTTCTGGTCAAAACATCACTGAAGAATTTTATCAATCAACATGCAG
TGCAGTTAGCAAAGGCTATCTTAGTGCTCTGAGAACTGGTTGGTATACCA
GTGTTATAACTATAGAATTAAGTAATATCAAGGAAAATAAGTGTAATGGA
ACAGATGCTAAGGTAAAATTGATAAAACAAGAATTAGATAAATATAAAA
TGCTGTAACAGAATTGCAGTTGCTCATGCAAAGCACACCACCAACAAACA
ATCGAGCCAGAAGAGAACTACCAAGGTTTATGAATTATACACTCAACAAT
GCCAAAAAAACCAATGTAACATTAAGCAAGAAAAGGAAAAGAAGATTTCT
TGGTTTTTTGTTAGGTGTTGGATCTGCAATCGCCAGTGGCGTTGCTGTAT
CTAAGGTCCTGCACCTAGAAGGGGAAGTGAACAAGATCAAAAGTGCTCTA
CTATCCACAAACAAGGCTGTAGTCAGCTTATCAAATGGAGTTAGTGTCTT
AACCAGCAAAGTGTTAGACCTCAAAAACTATATAGATAAACAATTGTTAC
CTATTGTGAACAAGCAAAGCTGCAGCATATCAAATATAGAAACTGTGATA
GAGTTCCAACAAAAGAACAACAGACTACTAGAGATTACCAGGGAATTTAG
TGTTAATGCAGGTGTAACTACACCTGTAAGCACTTACATGTTAACTAATA
GTGAATTATTGTCATTAATCAATGATATGCCTATAACAAATGATCAGAAA
AAGTTAATGTCCAACAATGTTCAAATAGTTAGACAGCAAAGTTACTCTAT
CATGTCCATAATAAAGAGGAAGTCTTAGCATATGTAGTACAATTACCAC
TATATGGTGTTATAGATACACCCTGTTGGAAACTACACACATCCCCTCTA
TGTACAACCAACACAAAAGAAGGGTCCAACATCTGTTTAACAAGAACTGA
CAGAGGATGGTACTGTGACAATGCAGGATCAGTATCTTTCTTCCCACAAG
CTGAAACATGTAAAGTTCAATCAAATCGAGTATTTTGTGACACAATGAAC
AGTTTAACATTACCAAGTGAAATAAATCTCTGCAATGTTGACATATTCAA
CCCCAAATATGATTGTAAAATTATGACTTCAAAAACAGATGTAAGCAGCT
CCGTTATCACATCTCTAGGAGCCATTGTGTCATGCTATGCAAAACTAAA
TGTACAGCATCCAATAAAAATCGTGGAATCATAAAGACATTTTCTAACGG

GTGCGATTATGTATCAAATAAAGGGATGGACACTGTGTCTGTAGGTAACA
CATTATATTATGTAAATAAGCAAGAAGGTAAAAGTCTCTATGTAAAAGGT
GAACCAATAATAAATTTCTATGACCCATTAGTATTCCCCTCTGATGAATT
TGATGCATCAATATCTCAAGTCAACGAGAAGATTAACCAGAGCCTAGCAT
TTATTCGTAAATCCGATGAATTATTACATAATGTAAATGCTGGTAAATCC
ACCACAAATATCATGATAACTACTATAATTATAGTGATTATAGTAATATT
GTTATCATTAATTGCTGTTGGACTGCTCTTATACTGTAAGGCCAGAAGCA
CACCAGTCACACTAAGCAAAGATCAACTGAGTGGTATAAATAATATTGCA
TTTAGTAACTAAGAATTCCACGTGGGATCCGTCGAGGAATTCACTCCTCA
GGTGCAGGCTGCCTATCAGAAGGTGGTGGCTGGTGTGGCCAATGCCCTGG
CTCACAAATACCACTGAGATCTTTTTCCCTCTGCCAAAAATTATGGGGAC
ATCATGAAGCCCCTTGAGCATCTGACTTCTGGCTAATAAAGGAAATTTAT
TTTCATTGCAATAGTGTGTTGGAATTTTTTGTGTCTCTCACTCGGAAGGA
CATATGGGAGGGCAAATCATTTAAAACATCAGAATGAGTATTTGGTTTAG
AGTTTGGCAACATATGCCCATATGCTGGCTGCCATGAACAAAGGTTGGCT
ATAAAGAGGTCATCAGTATATGAAACAGCCCCCTGCTGTCCATTCCTTAT
TCCATAGAAAAGCCTTGACTTGAGGTTAGATTTTTTTATATTTTGTTTT
GTGTTATTTTTTCTTTAACATCCCTAAAATTTTCCTTACATGTTTTACT
AGCCAGATTTTCCTCCTCTCCTGACTACTCCCAGTCATAGCTGTCCCTC
TTCTCTTATGGAGATCCCTCGACGGATCGGCCGCAATTCGTAATCATGTC
ATAGCTGTTTCCTGTGTGAAATTGTTATCCGCTCACAATTCCACACAACA
TACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAA
CCTGTCGTGCCAGCTGCATTAATGAATCGGCCAACGCGCGGGGAGAGGCG
GTTTGCGTATTGGGCGCTCTTCCGCTTCCTCGCTCACTGACTCGCTGCGC
TCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAG
TCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAAC
TATCGTCTTGAGTCCAACCCGGTAAGACACGACTTATCGCCACTGGCAGC
AGCCACTGGTAACAGGATTAGCAGAGCGAGGTATGTAGGCGGTGCTACAG
AGTTCTTGAAGTGGTGGCCTAACTACGGCTACACTAGAAGAACAGTATTT
GGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGG
```

```
GATTTTGGTCATGAGATTATCAAAAAGGATCTTCACCTAGATCCTTTTAA

ATTAAAAATGAAGTTTTAAATCAATCTAAAGTATATATGAGTAAACTTGG

TCTGACAGTTACCAATGCTTAATCAGTGAGGCACCTATCTCAGCGATCTG

TCTATTTCGTTCATCCATAGTTGCCTGACTCCCCGTCGTGTAGATAACTA

CGATACGGGAGGGCTTACCATCTGGCCCCAGTGCTGCAATGATACCGCGA

GACCCACGCTCACCGGCTCCAGATTTATCAGCAATAAACCAGCCAGCCGG

AAGGGCCGAGCGCAGAAGTGGTCCTGCAACTTTATCCGCCTCCATCCAGT

CTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTC

GTTTGGTATGGCTTCATTCAGCTCCGGTTCCCAACGATCAAGGCGAGTTA

CATGATCCCCCATGTTGTGCAAAAAAGCGGGTTAGCTCCTTCGGTCCTCC

GATCGTTGTCAGAAGTAAGTTGGCCGCAGTGTTATCACTCATGGTTATGG

CAGCACTGCATAATTCTCTTACTGTCATGCCATCCGTAAGATGCTTTTCT

GTGACTGGTGAGTACTCAACCAAGTCATTCTGAGAATAGTGTATGCGGCG

ACCGAGTTGCTCTTGCCCGGCGTCAATACGGGATAATACCGCGCCACATA

GCAGAACTTTAAAAGTGCTCATCATTGGAAAACGTTCTTCGGGGCGAAAA

CTCTCAAGGATCTTACCGCTGTTGAGATCCAGTTCGATGTAACCCACTCG

TGCACCCAACTGATCTTCAGCATCTTTTACTTTCACCAGCGTTTCTGGGT

GAGCAAAAACAGGAAGGCAAAATGCCGCAAAAAAGGGAATAAGGGCGACA

CGGAAATGTTGAATACTCATACTCTTCCTTTTTCAATATTATTGAAGCAT

TTATCAGGGTTATTGTCTCATGAGCGGATACATATTTGAATGTATTTAGA

AAAATAAACAAATAGGGGTTCCGCGCACATTTCCCCGAAAAGTGCCACCT

AAATTGTAAGCGTTAATATTTTGTTAAAATTCGCGTTAAATTTTTGTTAA

ATCAGCTCATTTTTTAACCAATAGGCCGAAATCGGCAAAATCCCTTATAA

ATCAAAAGAATAGACCGAGATAGGGTTGAGTGTTGTTCCAGTTTGGAACA

AGAGTCCACTATTAAAGAACGTGGACTCCAACGTCAAAGGGCGAAAAACC

GTCTATCAGGGCGATGGCCCACTACGTGAACCATCACCCTAATCAAGTTT

TTTGGGGTCGAGGTGCCGTAAAGCACTAAATCGGAACCCTAAAGGGAGCC

CCCGATTTAGAGCTTGACGGGGAAAGCCGGCGAACGTGGCGAGAAAGGAA

GGGAAGAAAGCGAAAGGAGCGGGCGCTAGGGCGCTGGCAAGTGTAGCGGT

CACGCTGCGCGTAACCACCACACCCGCCGCGCTTAATGCGCCGCTACAGG

GCGCGTCCCATTCGCCATTCAGGCTGCGCAACTGTTGGGAAGGGCGATCG

GTGCGGGCCTCTTCGCTATTACGCCAGCTGGCGAAAGGGGGATGTGCTGC

AAGGCGATTAAGTTGGGTAACGCCAGGGTTTTCCCAGTCACGACGTTGTA

AAACGACGGCCAGTGAGCGCGCGTAATACGACTCACTATAGGGCGAATTG

GAGCTCCACCGCGGTGGCGGCCGCT

SEQ ID NO: 24 is a Propol II Vector Including a
Codon Optimized Nucleotide Sequence of RSV-Fg
CTAGAGAGCTTGGCCCATTGCATACGTTGTATCCATATCATAATATGTAC

ATTTATATTGGCTCATGTCCAACATTACCGCCATGTTGACATTGATTATT
```

```
GACTAGTTATTAATAGTAATCAATTACGGGGTCATTAGTTCATAGCCCAT

ATATGGAGTTCCGCGTTACATAACTTACGGTAAATGGCCCGCCTGGCTGA

CCGCCCAACGACCCCCGCCCATTGACGTCAATAATGACGTATGTTCCCAT

AGTAACGCCAATAGGGACTTTCCATTGACGTCAATGGGTGGAGTATTTAC

GGTAAACTGCCCACTTGGCAGTACATCAAGTGTATCATATGCCAAGTACG

CCCCCTATTGACGTCAATGACGGTAAATGGCCCGCCTGGCATTATGCCCA

GTACATGACCTTATGGGACTTTCCTACTTGGCAGTACATCTACGTATTAG

TCATCGCTATTACCATGGTGATGCGGTTTTGGCAGTACATCAATGGGCGT

GGATAGCGGTTTGACTCACGGGGATTTCCAAGTCTCCACCCCATTGACGT

CAATGGGAGTTTGTTTTGGCACCAAAATCAACGGGACTTTCCAAAATGTC

GTAACAACTCCGCCCCATTGACGCAAATGGGCGGTAGGCGTGTACGGTGG

GAGGTCTATATAAGCAGAGCTCGTTTAGTGAACCGTCAGATCGCCTGGAG

ACGCCATCCACGCTGTTTTGACCTCCATAGAAGACACCGGGACCGATCCA

GCCTCCGGTCGACCGATCCTGAGAACTTCAGGGTGAGTTTGGGGACCCTT

GATTGTTCTTTCTTTTTCGCTATTGTAAAATTCATGTTATATGGAGGGGG

CAAAGTTTTCAGGGTGTTGTTTAGAATGGGAAGATGTCCCTTGTATCACC

ATGGACCCTCATGATAATTTTGTTTCTTTCACTTTCTACTCTGTTGACAA

CCATTGTCTCCTCTTATTTTCTTTTCATTTTCTTGTAACTTTTTCGTTAA

ACTTTAGCTTGCATTTGTAACGAATTTTTAAATTCACTTTTGTTTATTTG

TCAGATTGTAAGTACTTTCTCTAATCACTTTTTTTTCAAGGCAATCAGGG

TATATTATATTGTACTTCAGCACAGTTTTAGAGAACAATTGTTATAATTA

AATGATAAGGTAGAATATTTCTGCATATAAATTCTGGCTGGCGTGGAAAT

ATTCTTATTGGTAGAAACAACTACATCCTGGTCATCATCCTGCCTTTCTC

TTTATGGTTACAATGATATACACTGTTTGAGATGAGGATAAAATACTCTG

AGTCCAAACCGGGCCCCTCTGCTAACCATGTTCATGCCTTCTTCTTTTTC

CTACAGCTCCTGGGCAACGTGCTGGTTATTGTGCTGTCTCATCATTTTGG

CAAAGAATTCCTCGAGGTTTAAACGAATTCCGCCACCATGGAGTTGCTAA

TCCTCAAAGCAAATGCAATTACCACAATCCTCACTGCAGTCACATTTTGT

TTTGCTTCTGGTCAAAACATCACTGAAGAATTTTATCAATCAACATGCAG

TGCAGTTAGCAAAGGCTATCTTAGTGCTCTGAGAACTGGTTGGTATACCA

GTGTTATAACTATAGAATTAAGTAATATCAAGGAAAATAAGTGTAATGGA

ACAGATGCTAAGGTAAAATTGATAAAACAAGAATTAGATAAATATAAAAA

TGCTGTAACAGAATTGCAGTTGCTCATGCAAAGCACACCACCAACAAACA

ATCGAGCCAGAAGAGAACTACCAAGGTTTATGAATTATACACTCAACAAT

GCCAAAAAACCAATGTAACATTAAGCAAGAAAAGGAAAAGAAGATTTCT

TGGTTTTTTGTTAGGTGTTGGATCTGCAATCGCCAGTGGCGTTGCTGTAT

CTAAGGTCCTGCACCTAGAAGGGAAGTGAACAAGATCAAAGTGCTCTA

CTATCCACAAACAAGGCTGTAGTCAGCTTATCAAATGGAGTTAGTGTCTT

AACCAGCAAAGTGTTAGACCTCAAAAACTATATAGATAAACAATTGTTAC

CTATTGTGAACAAGCAAAGCTGCAGCATATCAAATATAGAAACTGTGATA
```

-continued

GAGTTCCAACAAAAGAACAACAGACTACTAGAGATTACCAGGGAATTTAG
TGTTAATGCAGGTGTAACTACACCTGTAAGCACTTACATGCTAACTAATA
GTGAATTATTGTCATTAATCAATGATATGCCTATAACAAATGATCAGAAA
AAGTTAATGTCCAACAATGTTCAAATAGTTAGACAGCAAAGTTACTCTAT
CATGTCCATAATAAAAGAGGAAGTCTTAGCATATGTAGTACAATTACCAC
TATATGGTGTTATAGATACACCCTGTTGGAAACTACACACATCCCCTCTA
TGTACAACCAACACAAAAGAAGGGTCCAACATCTGTTTAACAAGAACTGA
CAGAGGATGGTACTGTGACAATGCAGGATCAGTATCTTTCTTCCCACAAG
CTGAAACATGTAAAGTTCAATCAAATCGAGTATTTTGTGACACAATGAAC
AGTTTAACATTACCAAGTGAAATAAATCTCTGCAATGTTGACATATTCAA
CCCCAAATATGATTGTAAAATTATGACTTCAAAAACAGATGTAAGCAGCT
CCGTTATCACATCTCTAGGAGCCATTGTGTCATGCTATGGCAAAACTAAA
TGTACAGCATCCAATAAAAATCGTGGAATCATAAAGACATTTTCTAACGG
GTGCGATTATGTATCAAATAAAGGGATGGACACTGTGTCTGTAGGTAACA
CATTATATTATGTAAATAAGCAAGAAGGTAAAAGTCTCTATGTAAAAGGT
GAACCAATAATAAATTTCTATGACCCATTAGTATTCCCCTCTGATGAATT
TGATGCATCAATATCTCAAGTCAACGAGAAGATTAACCAGAGCCTAGCAT
TTATTCGTAAATCCGATGAATTATTACATAATGTTAACGCTGGTAAAAGT
ACTACAAATATCATGATAACTACTACTCGTTGGTTCAGTAGTTGGAAAAG
CTCTATTGCCTCTTTTTTCTTTATCATAGGGTTAATCATTGGACTATTCT
TGGTTCTCCGAGTTGGTATCCATCTTTGCATTAAATTAAAGCACACCAAG
AAAAGACAGATTTATACAGACATAGAGATGAACCGACTTGGAAAGTAAGA
ATTCGATATCGGATCCGTCGAGGAATTCACTCCTCAGGTGCAGGCTGCCT
ATCAGAAGGTGGTGGCTGGTGTGGCCAATGCCCTGGCTCACAAATACCAC
TGAGATCTTTTTCCCTCTGCCAAAAATTATGGGGACATCATGAAGCCCCT
TGAGCATCTGACTTCTGGCTAATAAAGGAAATTTATTTTCATTGCAATAG
TGTGTTGGAATTTTTTGTGTCTCTCACTCGGAAGGACATATGGGAGGGCA
AATCATTTAAAACATCAGAATGAGTATTTGGTTTAGAGTTTGGCAACATA
TGCCCATATGCTGGCTGCCATGAACAAAGGTTGGCTATAAAGAGGTCATC
AGTATATGAAACAGCCCCCTGCTGTCCATTCCTTATTCCATAGAAAAGCC
TTGACTTGAGGTTAGATTTTTTTATATTTTGTTTTGTGTTATTTTTTC
TTTAACATCCCTAAAATTTTCCTTACATGTTTTACTAGCCAGATTTTTCC
TCCTCTCCTGACTACTCCCAGTCATAGCTGTCCCTCTTCTCTTATGGAGA
TCCCTCGACGGATCGGCCGCAATTCGTAATCATGTCATAGCTGTTTCCTG
TGTGAAATTGTTATCCGCTCACAATTCCACACAACATACGAGCCGGAAGC
ATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGG
CGCTCTTCCGCTTCCTCGCTCACTGACTCGCTGCGCTCGGTCGTTCGGCT
GCGGCGAGCGGTATCAGCTCACTCAAAGGCGGTAATACGGTTATCCACAG
AATCAGGGGATAACGCAGGAAAGAACATGTGAGCAAAAGGCCAGCAAAAG

-continued

GCCAGGAACCGTAAAAAGGCCGCGTTGCTGGCGTTTTTCCATAGGCTCCG
CCCCCCTGACGAGCATCACAAAAATCGACGCTCAAGTCAGAGGTGGCGAA
ACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTC
CAACCCGGTAAGACACGACTTATCGCCACTGGCAGCAGCCACTGGTAACA
GGATTAGCAGAGCGAGGTATGTAGGCGGTGCTACAGAGTTCTTGAAGTGG
TGGCCTAACTACGGCTACACTAGAAGAACAGTATTTGGTATCTGCGCTCT
GCTGAAGCCAGTTACCTTCGGAAAAGAGTTGGTAGCTCTTGATCCGGCA
AACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGG
GTCTGACGCTCAGTGGAACGAAAACTCACGTTAAGGGATTTTGGTCATGA
GATTATCAAAAAGGATCTTCACCTAGATCCTTTTAAATTAAAAATGAAGT
TTTAAATCAATCTAAAGTATATATGAGTAAACTTGGTCTGACAGTTACCA
ATGCTTAATCAGTGAGGCACCTATCTCAGCGATCTGTCTATTTCGTTCAT
CCATAGTTGCCTGACTCCCCGTCGTGTAGATAACTACGATACGGGAGGGC
TTACCATCTGGCCCCAGTGCTGCAATGATACCGCGAGACCCACGCTCACC
GGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGT
TGCCATTGCTACAGGCATCGTGGTGTCACGCTCGTCGTTTGGTATGGCTT
CATTCAGCTCCGGTTCCCAACGATCAAGGCGAGTTACATGATCCCCCATG
TTGTGCAAAAAAGCGGGTTAGCTCCTTCGGTCCTCCGATCGTTGTCAGAA
GTAAGTTGGCCGCAGTGTTATCACTCATGGTTATGGCAGCACTGCATAAT
TCTCTTACTGTCATGCCATCCGTAAGATGCTTTTCTGTGACTGGTGAGTA
CTCAACCAAGTCATTCTGAGAATAGTGTATGCGGCGACCGAGTTGCTCTT
GCCCGGCGTCAATACGGGATAATACCGCGCCACATAGCAGAACTTTAAAA
GTGCTCATCATTGGAAAACGTTCTTCGGGGCGAAAACTCTCAAGGATCTT
ACCGCTGTTGAGATCCAGTTCGATGTAACCCACTCGTGCACCCAACTGAT
CTTCAGCATCTTTTACTTTCACCAGCGTTTCTGGGTGAGCAAAAACAGGA
AGGCAAAATGCCGCAAAAAAGGGAATAAGGGCGACACGGAAATGTTGAAT
ACTCATACTCTTCCTTTTTCAATATTATTGAAGCATTTATCAGGGTTATT
GTCTCATGAGCGGATACATATTTGAATGTATTTAGAAAAATAAACAAATA
GGGGTTCCGCGCACATTTCCCCGAAAAGTGCCACCTAAATTGTAAGCGTT
AATATTTTGTTAAAATTCGCGTTAAATTTTTGTTAAATCAGCTCATTTTT
TAACCAATAGGCCGAAATCGGCAAAATCCCTTATAAATCAAAAGAATAGA
CCGAGATAGGGTTGAGTGTTGTTCCAGTTTGGAACAAGAGTCCACTATTA
AAGAACGTGGACTCCAACGTCAAAGGGCGAAAAACCGTCTATCAGGGCGA

```
-continued
TGGCCCACTACGTGAACCATCACCCTAATCAAGTTTTTTGGGGTCGAGGT

GCCGTAAAGCACTAAATCGGAACCCTAAAGGGAGCCCCCGATTTAGAGCT

TGACGGGAAAGCCGGCGAACGTGGCGAGAAAGGAAGGGAAGAAAGCGAA

AGGAGCGGGCGCTAGGGCGCTGGCAAGTGTAGCGGTCACGCTGCGCGTAA

CCACCACACCCGCCGCGCTTAATGCGCCGCTACAGGGCGCGTCCCATTCG

CCATTCAGGCTGCGCAACTGTTGGGAAGGGCGATCGGTGCGGGCCTCTTC

GCTATTACGCCAGCTGGCGAAAGGGGGATGTGCTGCAAGGCGATTAAGTT

GGGTAACGCCAGGGTTTTCCCAGTCACGACGTTGTAAAACGACGGCCAGT

GAGCGCGCGTAATACGACTCACTATAGGGCGAATTGGAGCTCCACCGCGG

TGGCGGCCGCT

SEQ ID NO: 25 is a Codon Optimized GAG/ΔNSI
Nucleotide Sequence
CTCGAGGTTTAAACGAATTCCGCCACCATGGGACAGACCGTGACAACACC

CCTGAGCCTGACACTGGGACATTGGAAGGACGTGGAGCGCATCGCACATA

ACCAGAGCGTGGACGTGAAGAAGCGGAGATGGGTGACCTTCTGCTCCGCC

GAGTGGCCCACCTTCAACGTGGGATGGCCCCGGGACGGCACCTTCAACAG

AGATCTGATCACACAGGTGAAGATCAAGGTGTTTTCTCCAGGACCACACG

GACACCCAGACCAGGTGCCCTATATCGTGACCTGGGAGGCCCTGGCCTTC

GATCCACCTCCATGGGTGAAGCCTTTTGTGCACCCAAAGCCACCTCCACC

ACTGCCTCCAAGCGCCCCTTCCCTGCCACTGGAGCCACCTCGGAGCACCC

CACCCAGAAGCTCCCTGTATCCCGCCCTGACACCTAGCCTGGGGGCCAAG

CCTAAGCCACAGGTGCTGTCCGACTCTGGAGGACCACTGATCGACCTGCT

GACCGAGGACCCCCCACCATACCGCGATCCCCGGCCTCCACCATCCGACC

GGGATGGAAATGGAGGAGAGGCAACACCTGCCGGCGAGGCCCCCGACCCT

AGCCCAATGGCCTCCCGCCTGCGGGGCAGGCGCGAGCCTCCAGTGGCCGA

TTCTACCACAAGCCAGGCATTCCCTCTGAGAGCAGGAGGAAATGGCCAGC

TCCAGTATTGGCCATTTTCTAGCTCCGACCTGTACAACTGGAAGAACAAT

AACCCTAGCTTCTCCGAGGACCCCGGCAAGCTGACCGCCCTGATCGAGAG

CGTGCTGATCACCCACCAGCCCACATGGGACGATTGTCAGCAGCTCCTGG

GCACCCTGCTGACCGGAGAGGAGAAGCAGAGGGTGCTGCTGGAGGCAAGG

AAGGCCGTGAGAGGCGACGATGGCCGCCCAACCCAGCTCCCAAATGAGGT

GGATGCCGCCTTTCCTCTGGAGCGGCCAGACTGGGATTATACCACACAGG

CCGGCAGAAACCACCTGGTGCACTACAGACAGCTCCTGCTGGCCGGCCTG

CAGAATGCCGGCAGAAGCCCCACCAACCTGGCCAAGGTGAAGGGCATCAC

ACAGGGCCCCAATGAGTCTCCTAGCGCCTTTCTGGAGCGCCTGAAGGAGG

CCTACCGGAGATATACCCCATACGACCCTGAGGACCCCGACAGGAGACA

AACGTGTCCATGTCTTTCATCTGGCAGAGCGCCCCCGACATCGGCAGGAA

GCTGGAGCGCCTGGAGGACCTGAAGAATAAGACCCTGGGCGATCTGGTGA

GGGAGGCCGAGAAGATCTTCAACAAGCGCGAGACACCTGAGGAGAGAG

GAGCGGATCAGACGGGAGACAGAGGAGAAGGAGGAGCGGAGAAGGACAGA
```

```
-continued
GGACGAGCAGAAGGAGAAGGAGAGGGATCGCCGGAGACACCGCGAGATGA

GCAAGCTGCTGGCCACCGTGGTGTCCGGACAGAAGCAGGACAGGCAGGGA

GGAGAGCGGCGGCGGAGCCAGCTCGACAGAGATCAGTGCGCCTATTGTAA

GGAGAAGGGCCACTGGGCCAAGGATTGCCCCAAGAAGCCTCGCGGCCCAC

GGGGCCCCAGACCTCAGACCTCCCTGCTGACACTGGACGATGATCCAGCC

GTGATCGGCACAGCCGTGAAGGGCAAGGAGGCCGTGCACTCTGACCTGGG

CTACTGGATCGAGAGCGAGAAGAATGATACCTGGAGGCTGAAGCGCGCCC

ACCTGATCGAGATGAAGACATGCGAGTGGCCTAAGTCCCACACCCTGTGG

ACAGACGGCATCGAGGAGTCTGATCTGATCATCCCCAAGTCCCTGGCCGG

CCCTCTGTCTCACCACAACACCAGGGAGGGCTATCGCACACAGATGAAGG

GCCCCTGGCACAGCGAGGAGCTGGAGATCAGGTTTGAGGAGTGCCCTGGC

ACCAAGGTGCATGTGGAGGAGACATGTGGCACAAGGGGCCCATCCCTGCG

CTCTACCACAGCCAGCGGCAGAGTGATCGAGGAGTGGTGCTGTAGAGAGT

GCACAATGCCACCTCTGAGCTTCCGCGCAAAGGACGGCTGTTGGTACGGC

ATGGAGATCCGCCCTAGAAAAGAGCCCGAGAGCAATCTGGTCAGGTCAAT

GGTCACCGCTGGGTCCTAAGAATTCCACGTGGGATCC
```

DETAILED DESCRIPTION OF THE EMBODIMENTS

ZIKV, like other flaviviruses, is an enveloped virus having an RNA genome of about 11,000 bases. It falls within Group IV of the Baltimore classification system. It contains a nucleocapsid surrounded by a lipid bilayer derived from the host cell that contains two envelope proteins, E and M. The open reading frame of the ZIKV encodes a single amino acid sequence consisting of a polyprotein described as follows: 5'-C-prM-E-NS1-NS2A-NS2B-NS3-NS4A-NS4B-NS5-3' (see FIG. 1) and that is subsequently cleaved into capsid (C), precursor membrane (prM), envelope (E), and non-structural proteins (NS) by host proteases. A polyprotein is a large protein that is cleaved into separate smaller proteins with different biological functions. In some cases, an uncleaved polyprotein retains the biological activity of its component parts. There are two non-coding flanking regions known as the 5' NCR and the 3' NCR.

The E protein is a ZIKV envelope glycoprotein of approx. 500 amino acids which consist of four domains, a stem transmembrane domain that anchors the protein into the membrane and domains I, II, and III that constitute the predominantly beta-strand surface portion of the protein (Sirohi et al., 2016, Science 352: 467-470). The seven nonstructural proteins (NS1, NS2A, NS2B, NS3, NS4A, NS4B and NS5) are believed to be involved in replication, assembly and antagonizing the host innate response to infection based on the structure-function relationship of viral proteins in other flaviviruses such as West-Nile virus, Dengue virus and Japanese encephalitis virus, to which ZIKV displays a high degree of homology in its protein sequence and structure.

Recent phylogenetic analyses of ZIKV suggest that two different lineages of ZIKV emerged first in Africa (in Senegal and Cote d'Ivoire), followed by a third lineage in Asia. Recent outbreaks of ZIKV in Asia (Micronesia 2007), and more recently in the Americas (Brazil 2015), are related to the Asian lineage. Suriname isolate KU312312, isolated from a patient in 2015, was among the most recently published sequences of ZIKV as of spring, 2016. As such, this sequence is likely to have higher homology to the strains circulating in the Americas in 2015 and 2016 and to circulating ZIKV strains involved in future outbreaks The reproductive cycle of the ZIKV follows that of the other flaviviruses. It is initially assembled in the endoplasmic reticulum as trimeric E:prM heterodimer "spikes". During maturation, the prM protein is cleaved into the soluble pr peptide and the mature M protein by the host protease, furin. Removal of the pr peptide during the maturation process exposes the fusion loop, thereby enabling the virus to undergo endosomal fusion and emerge as a "smooth" enveloped virus (Sirohi et al, 2016).

Recent efforts to produce a vaccine for ZIKV focussed on DNA vaccines and inactivated ZIKV (Larocca et al, 2016). DNA vaccines were prepared using full length ZIKV prM and E immunogens using native sequences. Deletion mutants were also designed which lacked the prM, the transmembrane region of M or the full stem of E. The results showed that the full length prM-E vaccine elicited a higher antibody titer than the mutants. Furthermore, no prM specific antibody responses were detected. The results of the study are instructive because they indicate that wild-type ZIKV glycoprotein sequences are the most effective at eliciting an immunogenic response. The results of this study also indicate the importance of the E glycoprotein in inducing an immunogenic response.

The inventors herein have made a vaccine to ZIKV which comprises a VLP. VLPs are multiprotein structures which are generally composed of one or more viral proteins. VLP's mimic the conformation of viruses but lack genetic material, and therefore are not infectious. They can form (or "self-assemble") upon expression of a viral structural protein under appropriate circumstances. VLP vaccines overcome some of the disadvantages of more traditional vaccines prepared using attenuated viruses because they can be produced without the need to have any live virus present during the production process. A wide variety of VLPs have been prepared. For example, VLPs including single or multiple capsid proteins either with or without envelope proteins and/or surface glycoproteins have been prepared. In some cases, VLPs are non-enveloped and assemble by expression of just one major capsid protein. In other cases, VLPs are enveloped and can comprise multiple antigenic proteins found in the corresponding native virus. Self-assembly of enveloped VLPs is more complex than non-enveloped VLPs because of the complex reactions required for fusion with the host cell membrane (Garrone et al., 2011 Science Trans. Med. 3: 1-8) and "budding" of the VLP to form a fully enveloped separate particle. Accordingly, self-assembly of enveloped VLPs may not be successful and the formation and stability of enveloped VLP particles is difficult to predict. Formation of intact VLPs can be confirmed by imaging of the particles using electron microscopy.

VLPs typically resemble their corresponding native virus and can be multivalent particulate structures. The present disclosure encompasses the recognition that presentation of ZIKV surface glycoproteins in the context of a VLP is advantageous for induction of neutralizing antibodies against such ZIKV polypeptide as compared to other forms of antigen presentation, e.g., soluble antigens not associated with a VLP. Neutralizing antibodies most often recognize tertiary or quaternary structures; this often requires presenting antigenic proteins, like envelope glycoproteins, in their native viral conformation. Alternatively or additionally, VLPs may be useful for presenting antigens in a context which induces cellular immunity (e.g., T cell response). Antigens present within the internal space of the VLP may induce cellular immunity. For example, one of the non-structural proteins of the ZIKV may be included in a VLP to enhance cellular immunity. As an example, the presence of human leukocyte antigen class II-restricted T cell epitopes within a ZIKV non-structural protein may induce CD4-restricted T helper cell responses that help elicit and sustain both neutralizing antibody and cytotoxic T lymphocyte (CTL) responses. The present invention further encompasses the insight that use of antigen combinations in VLP systems can generate improved immune response.

The VLPs of the invention comprise retroviral vectors. Retroviruses are enveloped RNA viruses that belong to the family Retroviridae. After infection of a host cell by a retrovirus, RNA is transcribed into DNA via the enzyme reverse transcriptase. DNA is then incorporated into the host cell's genome by an integrase enzyme and thereafter replicates as part of the host cell's DNA. The Retroviridae family includes the following genera Alpharetrovirus, Betaretrovirus, Gammearetrovirus, Deltaretrovirus, Epsilonretrovirus, Lentivirus and Spumavirus. The hosts for this family of retroviruses generally are vertebrates. Retroviruses produce an infectious virion containing a spherical nucleocapsid (the viral genome in complex with viral structural proteins) surrounded by a lipid bilayer derived from the host cell membrane.

Retroviral vectors can be used to generate VLPs that lack a retrovirus-derived genome and are therefore non-replicating. This is accomplished by replacement of most of the coding regions of the retrovirus with genes or nucleotide sequences to be transferred; so that the vector is incapable of making proteins required for additional rounds of replication. Depending on the properties of the glycoproteins present on the surface of the particles, VLPs have limited ability to bind to and enter the host cell but cannot propagate. Therefore, VLPs can be administered safely as an immunogenic composition (e.g., a vaccine).

The present invention utilizes VLPs comprised of one or more retroviral structural proteins. In some embodiments, a structural protein for use in accordance with the present invention is Alpharetrovirus (e.g., Avian Leukosis Virus), Betaretrovirus (Mouse Mammary Tumor Virus), Gammearetrovirus (Murine Leukemia Virus), Deltaretrovirus (Bovine Leukemia Virus), Epsilonretrovirus (Walley Dermal Sarcoma Virus), Lentivirus (Human Immunodeficiency Virus 1) or Spumavirus (Chimpanzee Foamy Virus) structural protein. In certain embodiments, a structural polyprotein is a Murine Leukemia Virus (MLV) structural protein. In an embodiment of the invention the structural protein in a Moloney Murine Leukemia Virus (MMLV). Genomes of these retroviruses are readily available in databases.

In some embodiments, the retroviral structural protein for use in accordance with the present invention is a Gag polypeptide. The Gag proteins of retroviruses have an overall structural similarity and, within each group of retroviruses, are conserved at the amino acid level. Retroviral Gag proteins primarily function in viral assembly. Expression of Gag of some viruses (e.g., murine leukemia viruses, such as MMLV) in some host cells, can result in self-assembly of the expression product into VLPs. The Gag gene expression product in the form of a polyprotein gives rise to the core structural proteins of the VLP. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. In general, the form of the Gag protein that mediates viral particle assembly is the polyprotein. Retroviruses assemble an immature capsid composed of the Gag polyprotein but devoid of other viral elements like viral protease with Gag as the structural protein of the immature virus particle.

A suitable Gag polypeptide for use in the invention is substantially homologous to a known retroviral Gag polypeptide. The MMLV-Gag gene encodes a 65 kDa polyprotein precursor which is proteolytically cleaved into 4 structural proteins (Matrix (MA); p12; Capsid (CA); and Nucleocapsid (NC)), by MLV protease, in the mature virion. In the absence of MLV protease, the polyprotein remains uncleaved- and the resulting particle remains in an immature form. The morphology of the immature particle is different from that of the mature particle. In some embodiments of the invention, the Gag sequence does not include a gene encoding MLV protease. The gene encoding the MMLV nucleic acid is SEQ ID NO: 2. An exemplary codon optimized sequence of MMLV nucleic acid is provided as SEQ ID NO: 3.

Therefore, in some embodiments, a Gag polypeptide suitable for the present invention is substantially homologous to an MMLV-Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Gag polypeptide suitable for the present invention is substantially identical to, or identical to SEQ ID NO: 1.

In some embodiments, a suitable MMLV-Gag polypeptide is encoded by a nucleic acid sequence having at least 80%, 85%, 90%, 91%, 92%, 93%, 94%, 95%, 96%, 97%, 98%, 99% sequence identity to SEQ ID NO:2. In some embodiments, a suitable MMLV-Gag polypeptide is encoded by a nucleic acid sequence having SEQ ID NO: 2 or a codon degenerate version thereof.

As is well known to those of skill in the art, it is possible to improve the expression of a nucleic acid sequence in a host organism by replacing the nucleic acids coding for a particular amino acid (i.e. a codon) with another codon which is better expressed in the host organism. One reason that this effect arises is due to the fact that different organisms show preferences for different codons. The process of altering a nucleic acid sequence to achieve better expression based on codon preference is called codon optimization. Various methods are known in the art to analyze codon use bias in various organisms and many computer algorithms have been developed to implement these analyses in the design of codon optimized gene sequences. Therefore, in some embodiments, a suitable MMLV-Gag polypeptide is encoded by a codon optimized version of a nucleic acid sequence encoding MMLV-Gag and having at least 80%, 85%, 90%, 91%, 92%, 93%, 94%, 95%, 96%, 97%, 98%, 99% sequence identity to SEQ ID NO:3. In some embodiments, a suitable MMLV-Gag polypeptide is encoded by a nucleic acid sequence which is substantially identical to, or identical to, SEQ ID NO: 3.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Examples of such programs are described in Altschul, et al., 1990, *J. Mol. Biol.*, 215(3): 403-410; Altschul, et al., 1996, *Methods in Enzymology* 266:460-480; Altschul, et al., 1997 *Nucleic Acids Res.* 25:3389-3402; Baxevanis, et al., 1998, *Bioinformatics: A Practical Guide to the Analysis of Genes and Proteins*, Wiley; and Misener, et al., (eds.), 1999, *Bioinformatics Methods and Protocols* (Methods in Molecular Biology, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Alternatively, the Gag polypeptide used in the invention may be a modified retroviral Gag polypeptide containing one or more amino acid substitutions, deletions, and/or insertions as compared to a wild-type or naturally-occurring Gag polypeptide while retaining substantial self-assembly activity. Typically, in nature, a Gag protein includes a large C-terminal extension which may contain retroviral protease, reverse transcriptase, and integrase enzymatic activity. Assembly of VLPs, however, generally does not require the presence of such components. In some cases, a retroviral Gag protein alone (e.g., lacking a C-terminal extension, lacking one or more of genomic RNA, reverse transcriptase, viral protease, or envelope protein) can self-assemble to form VLPs both in vitro and in vivo (Sharma S et al., 1997, Proc. Natl. Acad. Sci. USA 94: 10803-8).

In some embodiments, a Gag polypeptide for use in accordance with the present invention lacks a C-terminal extension and/or contains a modified C-terminal extension. A Gag polypeptide may optionally include one or more additional polypeptides (e.g., a heterologous antigen). In some embodiments, a Gag polypeptide is co-expressed with a heterologous antigen (e.g., under separate promoters and/or as separate proteins). In some embodiments, a Gag polypeptide is expressed as a fusion protein with a heterologous antigen. The Gag polypeptide can be linked to a heterologous antigen to create a fusion protein without altering Gag function. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. It has been observed that fusion of a self-assembling Gag polypeptide to a heterologous antigen creates a fusion protein that acts as unmodified Gag and, as a result, will allow the antigen to be incorporated into the structural components of a resulting VLP. In some embodiments, the VLP structural components of the present invention comprise a fusion protein of a Gag polypeptide (e.g., MMLV-Gag) and a ZIKV polypeptide. In some embodiments, the VLP structural components of the present invention comprise a fusion protein of a Gag polypeptide (e.g., MMLV-Gag) and the NS1 polypeptide of ZIKV. In some embodiments, the VLP structural components of the present invention comprise a fusion protein of a Gag polypeptide (e.g., MMLV-Gag) and a modified version of the NS1 polypeptide of ZIKV. In a preferred embodiment, the modified version of the NS1 polypeptide is a truncated version.

The inventors of the present application have made VLPs which express ZIKV envelope glycoproteins on the surface which can cause an immune response in a subject. A humoral immune response is an immune response mediated by antibody molecules. Certain antibodies, called neutralizing antibodies, defend cells from infection by a virus and associated biological effects by recognizing and binding to a particular protein or antigen expressed by the virus. The envelope proteins of ZIKV are important targets for production of neutralizing antibodies against ZIKV. It is well known to those in the art that retroviral Gag-based enveloped VLPs can be used to express a variety of envelope glycoproteins for the purpose of eliciting neutralizing antibody responses. More specifically, evidence exists for expression of Class I viral fusion proteins such as HIV-1 gp120, metapneumovirus and Influenza HA, as well as Class III fusion proteins such as VSV G protein and CMV gB protein (Mammano et al., 1997, J. Virol. 71:3341-3345; Levy et al., 2013, Vaccine 31:2778-2785; Lemaitre et al., 2011, Clin. Microbiol. Infect. 1:732-737; Garrone et al, 2011; Kirchmeier et al., 2014, CVI 21: 174-180). However, there is little known about expression of class II viral fusion proteins, including the ZIKV E glycoprotein protein, particularly with MLV-derived Gag. In U.S. Pat. No. 8,920,812, Example 1 describes a failure to express RSV F glycoprotein, a class II viral fusion protein, on the surface of a VLP produced using MLV Gag. The inventor hypothesized that the presence of the RSV F glycoprotein interfered with budding of the Gag viral particle through the cell membrane (see column 41, line 50). It was therefore not predictable that a retroviral Gag-based enveloped virus-like particle could be used to successfully express the ZIKV E protein. Nevertheless, the present inventors have made several different embodiments of a ZIKV vaccine comprising one or more envelope polypeptide antigens (e.g., E or M) on the surface of a VLP. In some embodiments, the envelope polypeptide antigens comprise modified polypeptides.

In some embodiments, a VLP of the invention includes a fusion protein of an envelope polypeptide from ZIKV (e.g., all or part of an extracellular portion of an ZIKV envelope polypeptide) and a transmembrane and/or cytoplasmic domain that is not found in nature in the ZIKV protein (e.g., from another virus). In some embodiments, a fusion protein includes an envelope polypeptide from ZIKV (e.g., all or part of an extracellular portion of a ZIKV envelope polypeptide) and a transmembrane domain and/or cytoplasmic domain found in nature in the glycoprotein G from VSV which is referred to as VSV-G. The nucleotide and amino acid sequences of the VSV-G protein are known in the art.

The transmembrane domain of VSV-G can function to target the viral glycoprotein to the cell membrane (Compton T et al., 1989, Proc Natl Acad Sci USA 86:4112-4116). Swapping the transmembrane and cytoplasmic domains of VSV-G for the transmembrane and cytoplasmic domains of another protein has been used to increase the yield of the protein of interest in the VLP preparation and increase immunogenicity to neutralizing antibody response (Garrone et al., 2011). This modification was successful to increase yield and activity of a VLP expressing HCV-E1 protein (Garrone et al, 2011) and CMV-gB protein (Kirchmeier et al, 2014). However, this modification has also been associated with a significant loss of immunogenicity when used with certain viral antigens. In addition, expression of some glycoproteins has decreased after replacement of the transmembrane/cytoplasmic domain of the antigenic glycoprotein with the transmembrane/cytoplasmic domain from VSV. For example, loss of glycoprotein was reported in SARS virus (Broer et al., 2006, J. Vir. 80, 1302-1310). In RSV, a significant loss of immunogenicity was observed when the antigenic surface protein was modified to replace the transmembrane component with a sequence from VSV (See Example 6).

In some embodiments, the immunogenic composition of the present invention comprises a VLP comprising a wild type envelope ZIKV polypeptide comprising the ZIKV M and E polypeptides, the sequence of which is SEQ ID NO: 4 or a codon degenerate version of SEQ ID NO: 4. A nucleic acid which encodes for the polypeptide is shown as SEQ ID NO: 5. A codon optimized version of SEQ ID NO: 5 is shown as SEQ ID NO: 6. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 4. In some embodiments, the present invention comprises an immunogenic composition comprising a VLP comprising a polypeptide having an amino acid sequence which is SEQ ID NO: 4 or a codon degenerate version of SEQ ID NO: 4. In some embodiments, the polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 5. In some embodiments, the polypeptide is encoded by a codon optimized version of the nucleic acid sequence of SEQ ID NO: 5, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 6. In some embodiments, the mutated polypeptide is encoded by a nucleic acid sequence having SEQ ID NO: 6.

In some embodiments, the immunogenic compositions of the present invention comprise VLPs comprising variants of ZIKV envelope glycoproteins. In some embodiments, a variant ZIKV envelope glycoprotein has been modified to delete the furin cleavage site from the ZIKV polypeptide. In some embodiments, the ZIKV envelope glycoprotein has been modified to delete the glycosylation site on the E protein. In some embodiments, the viral envelope glycoprotein has been modified to delete the M protein. An illustration of these modifications to the ZIKV polyprotein is shown in FIG. 1. Each such modification is further described below.

It is known that the ZIKV polyprotein includes a site where the protease, furin, cleaves the prM polypeptide to give the pr peptide and the M protein during the process of virion maturation. A modified ZIKV protein construct was produced wherein the amino acid sequence was modified to remove the furin cleavage site, thus retaining the prM polypeptide in its immature form. Unexpectedly, the inventors have discovered that the furin-cleavage site mutated version of the ZIKV construct, which does not undergo normal cleavage and maturation of the protein, shows enhanced cell receptor binding and cell entry, indicating that immunity against this structure may result in humoral immunity with greater neutralizing activity. Without wishing to be bound by any theory, it is possible that this effect is caused by greater exposure of the fusion loop. This result was unexpected in view of the results shown with DNA vaccines against ZIKV wherein unmodified sequences of ZIKV surface glycoproteins demonstrated greater activity than modified surface glycoproteins (Larocca, 2016).

In some embodiments, the immunogenic composition of the invention comprises a VLP comprising a modified ZIKV polypeptide with a mutated furin cleavage site as compared to a wild-type or naturally-occurring ZIKV polypeptide. The sequence for the modified ZIKV polypeptide is shown as SEQ ID NO: 7. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 7. In some embodiments, the present invention comprises an immunogenic composition comprising a VLP comprising a polypeptide having an amino acid sequence which is SEQ ID NO: 7 or a codon degenerate version of SEQ ID NO: 7. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 8. In some embodiments, the modified polypeptide is encoded by a codon optimized version of the nucleic acid sequence of SEQ ID NO: 8, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 9. In some embodiments, the mutated polypeptide is encoded by a nucleic acid sequence having SEQ ID NO: 9.

It is known from the study of other flaviviruses that the N-linked glycosylation site around position 154 of the E glycoprotein is important for infectivity and assembly of the virus (Lee et al., 2010 J. Virol. 84: 5171-5180) and that a polymorphism is observed in this motif (Faye et al., 2014, PLoS Negl Trop Dis. 2014 8:e2636. doi: 10.1371). Therefore, it is possible that there is a correlation between the N-glycosylation site of the ZIKV E glycoprotein and immune response to ZIKV. Accordingly, a ZIKV polypeptide construct was prepared which has been modified to abrogate the N-glycosylation site on the E glycoprotein (see FIG. 1). In some embodiments, the immunogenic composition of the invention comprises a VLP comprising a ZIKV polypeptide which has been modified to abrogate the glycosylation site on the E polypeptide as compared to a wild-type or naturally-occurring ZIKV E polypeptide. The sequence of the modified polypeptide is shown in SEQ ID NO: 13. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 13. In some embodiments, the present invention comprises an immunogenic composition comprising a VLP comprising a polypeptide having an amino acid sequence which is SEQ ID NO: 13 or a codon degenerate version of SEQ ID NO: 13. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 14. In some embodiments, the modified polypeptide is encoded by a codon optimized version of the nucleic acid sequence of SEQ ID NO: 14, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO:15. In some embodiments, the modified polypeptide is encoded by a nucleic acid sequence having SEQ ID NO: 15.

In some embodiments, the immunogenic composition of the invention comprises a VLP comprising a modified ZIKV polypeptide which has been modified to remove the M glycoprotein, leaving the E glycoprotein as the sole ZIKV glycoprotein. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to the sequence of the naturally occurring ZIKV E protein. In some embodiments, the present invention comprises an immunogenic composition comprising a VLP comprising a polypeptide having an amino acid sequence which is the same as the sequence of the naturally occurring ZIKV E polypeptide.

In some embodiments, a VLP described herein comprises a fusion protein comprising an extracellular domain (or a portion thereof) of a ZIKV envelope polypeptide, and a transmembrane domain from an envelope protein from VSV. In some embodiments, the immunogenic composition of the invention comprises a VLP comprising a modified ZIKV polypeptide which has been modified to remove the M glycoprotein, leaving the E glycoprotein as the sole ZIKV glycoprotein, and this modified ZIKV polypeptide has been further modified to replace the transmembrane domain and cytoplasmic tail with the transmembrane domain and cytoplasmic tail of VSV. This construct is referred to as "EG". The sequence of this double modified ZIKV polypeptide is shown as SEQ ID NO: 10 (shown above with the portion from VSV underlined). In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 10. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 11. In some embodiments, the modified polypeptide is encoded by a codon optimized version of the nucleic acid sequence of SEQ ID NO: 11, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 12. In some embodiments, the modified polypeptide is encoded by a nucleic acid sequence having SEQ ID NO: 12.

The inventors successfully produced VLPs using all four of the ZIKV envelope polypeptides described above. The VLPs produced using the ZIKV envelope protein variant in which the glycosylation site was abrogated showed the presence of only trace amounts of the ZIKV E polypeptide. Therefore, no further studies were conducted using this ZIKV VLP construct.

VLPs produced using the three remaining ZIKV envelope protein constructs were used in a mouse study to determine which of the three constructs would produce the most antigenic effect. The mouse study showed that the VLP incorporating the polypeptide having SEQ ID NO: 10 (i.e. the construct having the isolated ZIKV E protein, in which the M polypeptide was removed) showed significantly higher antigenicity than the other VLPs having different ZIKV envelope polypeptide constructs. This result was surprising because the most antigenic construct did not include the ZIKV M polypeptide, which occurs in the natural ZIKV. As discussed above, previous studies using ZIKV DNA vaccines demonstrated that higher titres were obtained using the native ZIKV prM-E envelope polypeptide. Accordingly, it was highly unexpected that a modified version missing the prM component would prove to be significantly more effective. As well, the significantly better result occurred using the VSV transmembrane domain, the use of which has produced unpredictable results in the past and, in fact, failure in similar constructs using an envelope polypeptide from the RSV virus (see Example 6).

As an alternative embodiment, the VLPs of the present invention can contain one or more epitopes from ZIKV non-structural proteins which are antigens that play a role in induction of cellular immune responses (e.g., T-cell response). The one or more epitopes from a ZIKV non-structural protein can be present with or without a ZIKV envelope protein. In some embodiments, the utilized non-structural proteins both stimulate formation of T-helper cells ($T_H$) and also induce cytotoxic T lymphocytes (CTL) against ZIKV (e.g., via a cell-mediated immune response). An important aspect of immunological response to an antigen is played by T cell response. In this regard, CD4+ T cells are crucial.

The NS1 protein is a highly conserved flavivirus protein which is a major target of CD4+ T cells. CD4+ T cell response against NS1 has been described in recovered Japanese encephalitis ("JEV") patients 6 years after exposure (Turtle et al., 2016, J. Exp. Med. 213:1331-1352) and in healthy children from JEV endemic areas (Kumar et al., 2004, J Gen Virol. 85:471-82). In order to ensure incorporation of NS1 in the interior of the VLP, the NS1 can be expressed as a fusion protein with the Gag, during VLP assembly. The amino acid sequence of a Gag-NS1 fusion protein is SEQ ID NO: 16 (shown above with the NS1 portion of the fusion protein underlined). A nucleic acid sequence encoding a Gag-NS1 fusion protein is SEQ ID NO: 17. In some embodiments, the immunogenic composition of the invention comprises a VLP comprising a ZIKV NS1 protein. In some embodiments, the NS1 polypeptide is expressed as part of a Gag-NS1 fusion protein encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 17. In some embodiments, the mutated polypeptide is encoded by a codon optimized version of the nucleic acid sequence of SEQ ID NO: 17, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 18. In some embodiments, the Gag-NS1 fusion polypeptide is encoded by a nucleic acid sequence having SEQ ID NO: 18.

Figure 2:
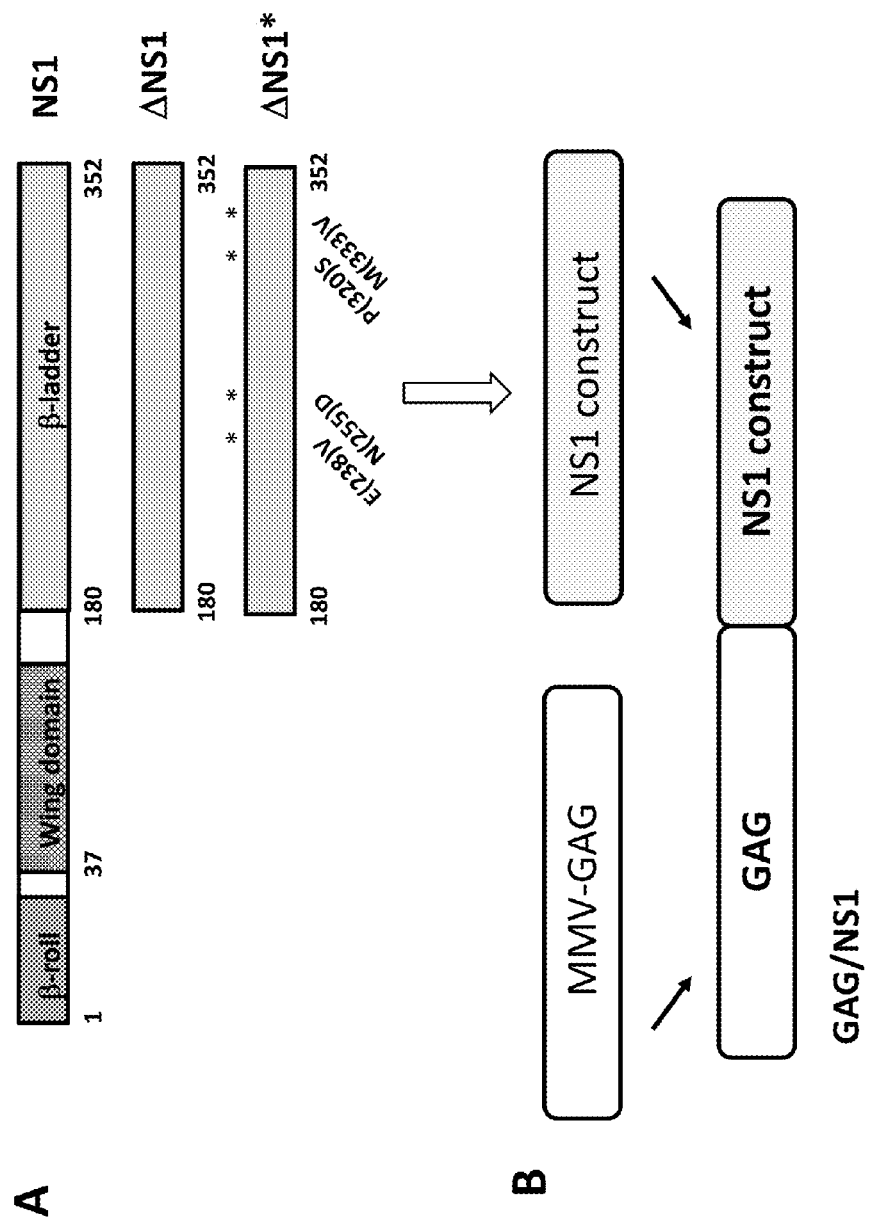
FIG. 2 shows (A) the structure of the ZIKV NS1 protein and (B) the structure of a fusion protein comprising GAG and ZIKV NS1, GAG and a ZIKV NSI fragment, and a ZIKV NSI modified fragment.

The nature and size of the fused Gag-NS1 protein could, potentially, alter the assembly of the VLP resulting in poor particle yields or, possibly, the complete absence of particle formation. In order to address this problem, modifications to NS1 were designed (see FIG. 2). It is not possible to predict the effect of these modifications on VLP yield or assembly, so modified NS1 fusion proteins were designed, produced and tested in ZIKV VLP production.

Modifications to the ZIKV NS1 protein were based on an understanding of the NS1 epitopes from a related flavivirus, Dengue. Analysis of T cell lines isolated from patients diagnosed with Dengue virus infection identified specific epitopes for CD4+ or CD8+ T cells in the NS1 protein (Rivino et al., 2013, J. Virol. 87:2693-2706). The amino acid sequence of NS1 is highly conserved among flavivirus, including Dengue virus, JEV, West Nile virus and ZIKV and the protein structures have very similar features (Sirohi et al., (2016)). The NS1 protein consists of three separate domains, a beta roll, a wing domain and a beta ladder domain. The amino acid sequence of NS1 from ZIKV was aligned with NS1 from Dengue virus and a new NS1 ZIKV construct was designed comprising a fragment of the NS1 sequence consisting of the beta ladder domain (named ΔNS1), which includes most of the sections described as potential CD4+ T cell epitopes in the Dengue virus NS1, and corresponding to the C-terminus β-ladder of NS1. In order to ensure incorporation of ΔNS1 in the interior of the VLP, ΔNS1 can be expressed as a fusion protein with the Gag, during VLP assembly. The amino acid sequence of a Gag-ΔNS1 fusion protein is SEQ ID NO: 19 (shown above with the ΔNS1 portion of the fusion protein underlined). A nucleic acid sequence encoding a Gag-ΔNS1 fusion protein is SEQ ID NO: 20. In some embodiments, the immunogenic composition of the invention comprises a VLP comprising a ZIKV ΔNS1 protein. In some embodiments, the NS1 polypeptide is expressed as part of a Gag-ΔNS1 fusion protein encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 20.

A second modified ZIKV NS1 protein was designed to further investigate potential enhancements to immunogenicity. Toll-like receptors (TLRs) are proteins that have an essential role in the innate immune system, which defends host cells from infection by other organisms. TLRs recognize certain viral components, including double stranded RNA which is produced at a point in the viral lifecycle. In West Nile virus, double stranded RNA is detected by TLR3 in the host cells. Several reports claim that NS1 from West Nile virus inhibits TLR3 host cell response thus decreasing the immune response to the virus and one study shows that specific mutations on identified residues abrogate the inhibition (Morrison et al., 2014, Vir. 458-459:172-82). A modified NS1 (named ΔNS1*) was designed which consisted of the NS1 fragment of ΔNS1, with an additional mutation of 4 residues which are potentially responsible for TLR3 interaction in West Nile virus. In order to ensure incorporation of ΔNS1* in the interior of the VLP, ΔNS1* can be expressed as a fusion protein with the Gag, during VLP assembly. The amino acid sequence of a Gag-ΔNS1* fusion protein is SEQ ID NO: 21 (shown above with the ΔNS1* portion of the fusion protein underlined. A nucleic acid sequence encoding a Gag-ΔNS1* fusion protein is SEQ ID NO: 22. In some embodiments, the immunogenic composition of the invention comprises a VLP comprising a ZIKV ΔNS1* protein. In some embodiments, the ΔNS1* polypeptide is expressed as part of a Gag-ΔNS1* fusion protein encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 22.

Optimal modification was difficult to predict, therefore fusion constructs were produced and tested to determine the impact on assembly of particles and to further investigate their impact on immunogenicity. The results are described in Example 8.

All cells transfected with plasmids encoding the Gag-NS1 fusion protein died immediately after transfection. The cause of cell death was not evident. However, cell death was not observed when cells were transfected with plasmids encoding the Gag-ΔNS1 fusion protein. Proteins were expressed by the cells and VLP particles were observed using electron microscopy (see Table 9).

Monovalent VLP expressing the Gag-ΔNS1 fusion protein were used in animal studies to determine whether they elicited an immunological response. Not surprisingly, these monovalent VLPs did not produce an antibody response against ZIKV E protein. However, these monovalent VLPs did produce a significant T-cell response in mice, thus indicating that they elicit cellular immunity, which is important for long term, durable immunity against pathogens (see Example 10). Cellular immunity also serves to combat infection within cells, thus raising the prospect that these VLPs could limit damage to the cells of testes in males infected with ZIKV.

In an embodiment of the invention, bivalent VLPs were produced which contained both a ZIKV envelope glycoprotein and the modified NS1 polypeptide referred to above as ΔNS1. Each of the three modified ZIKV envelope glycoproteins described above were expressed in a bivalent VLP. The results are described in Example 8. As is shown in Example 8, VLP particles expressing each of the modified ZIKV envelope glycoproteins and a modified ΔNS1 were observed using electron microscopy.

Since the EG variant of the ZIKV surface polypeptide demonstrated superior antigenicity to the other constructs, it was selected for use in animal studies in order to evaluate the antigenicity of bivalent VLPs. VLPs were produced which include the EG ZIKV surface polypeptide and the ZIKV ΔNS1 protein. These constructs were tested in animal models to compare their antigenicity against a monovalent VLP containing the EG polypeptide alone, and against a combination of two monovalent VLPs (one containing the EG polypeptide alone and a second containing the ΔNS1 protein alone). It is expected that the bivalent combination of two monovalent VLPs might have somewhat superior antigenicity to a combination of two monovalent VLPs having the same antigens simply because the two antigens are presented together. However, mouse studies demonstrated that the combination of two monovalent VLPs demonstrated surprisingly low antigenicity, lower in fact that the single monovalent VLP having the EG surface polypeptide. The bivalent construct, having both the EG and the ZIKV ΔNS1 polypeptide demonstrated significantly superior antigenicity to the combination of two monovalent VLPs in mouse studies.

Mouse studies were also conducted to determine if VLPs containing the ZIKV ΔNS1 polypeptide would elicit a T-cell, cellular immune response using the enzyme-linked immunospot (ELISPOT) assay. The ELISPOT assay measures the frequency of cytokine-secreting cells. The results indicated that bivalent VLP, having both the EG and the ZIKV ΔNS1 polypeptide, demonstrated a strong T-cell response. This response was significantly stronger than the response elicited by a combination of two monovalent VLPs (one containing the EG polypeptide alone and a second containing the ΔNS1 protein alone). Furthermore, the bivalent VLP generated a T-cell response which was roughly equivalent to the cellular immune response elicited by the monovalent VLP expressing only the ZIKV ΔNS1 polypeptide. Accordingly, the bivalent VLP was surprisingly superior to the combination of two monovalent VLPs with respect to its activity in generating a T-cell response.

The superior ability of the bivalent VLP to generate a cellular immune response, in addition to an antibody response, indicates that a vaccine comprising this VLP can generate an enhanced and durable immune response to the ZIKV. Furthermore, it may fight ZIKV infection and thereby prevent damage caused by ZIKV to the testes of infected subjects.

Based on the various studies of the different VLPs produced using ZIKV polypeptides, the bivalent VLP construct containing the ZIKV EG polypeptide described herein and the modified ZIKV ΔNS1 polypeptide, described herein elicited both high antibody titres and a strong cellular immune response. The bivalent VLP produced a higher antibody titre against ZIKV E than the monovalent VLP expressing only ZIKV EG. As well, the bivalent VLP elicited a roughly equivalent cellular immune response to the monovalent VLP expressing only the modified ZIKV ΔNS1 polypeptide. These results are surprising since one would expect that a combination of antigens in a single VLP could dilute the immunological response to each individual antigen. Nevertheless, and even more surprisingly, the bivalent VLP was significantly superior in both antibody titre and cellular immune response to a combination of two monovalent VLPs expressing, individually, similar amounts of the ZIKV EG and modified ZIKV ΔNS1 polypeptide. This potent combination of immunological responses provides a significant improvement over existing ZIKV vaccines and offers a treatment which harnesses both humoral and cellular immunity to provide a long term and effective immunity against ZIKV.

It will be appreciated that a composition comprising VLPs will typically include a mixture of VLPs with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments, the distribution may be narrower, e.g., >90% of the vesicles in a composition may have a diameter which lies within 40, 30, 20, 10 or 5% of the most frequent value. In some embodiments, sonication or ultra-sonication may be used to facilitate VLP formation and/or to alter VLP size. In some embodiments, filtration, dialysis and/or centrifugation may be used to adjust the VLP size distribution.

In general, VLPs produced in accordance with the methods of the present disclosure may be of any size. In certain embodiments, the composition may include VLPs with diameters in the range of about 20 nm to about 300 nm. In some embodiments, a VLP is characterized in that it has a diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs within a population show an average diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs in a population have a polydispersity index that is less than 0.5 (e.g., less than 0.45, less than 0.4, or less than 0.3). In some embodiments, VLP diameter is determined by nanosizing. In some embodiments, VLP diameter is determined by electron microscopy.

Figure 3:
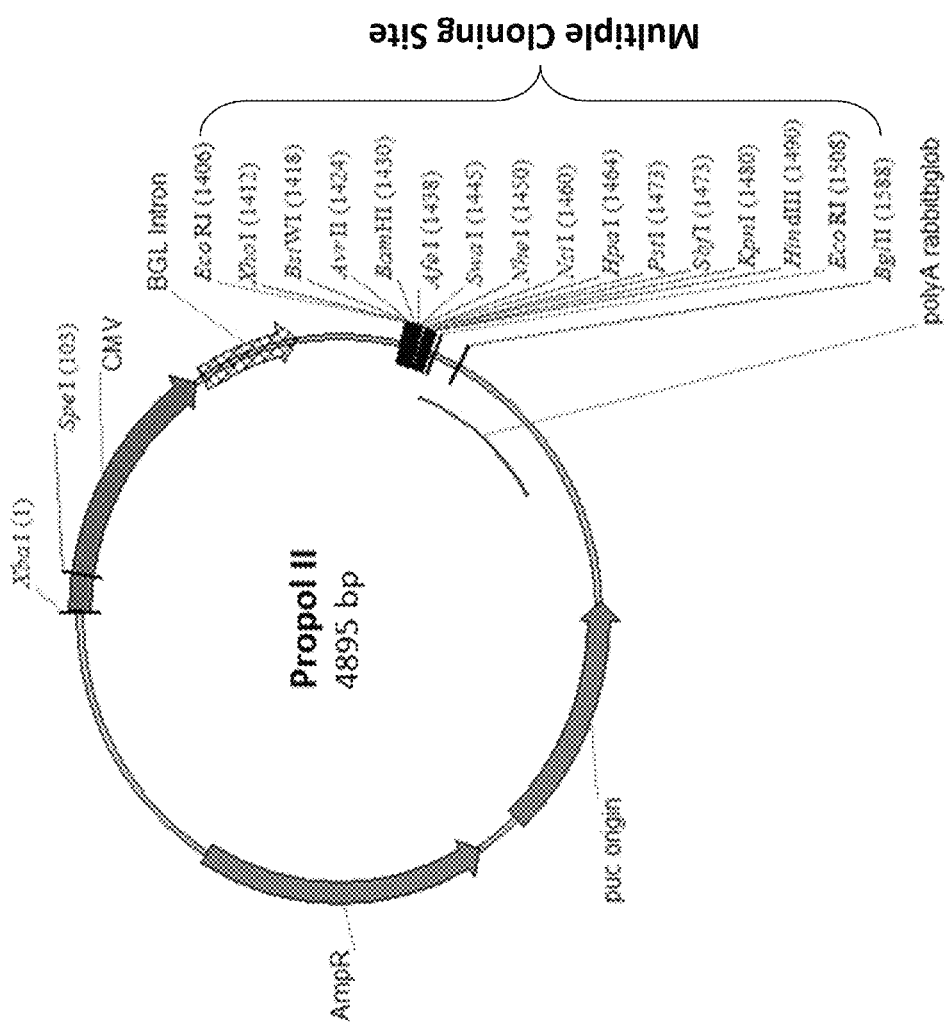
FIG. 3 shows the structure of a Propol II plasmid.
Figure 6:
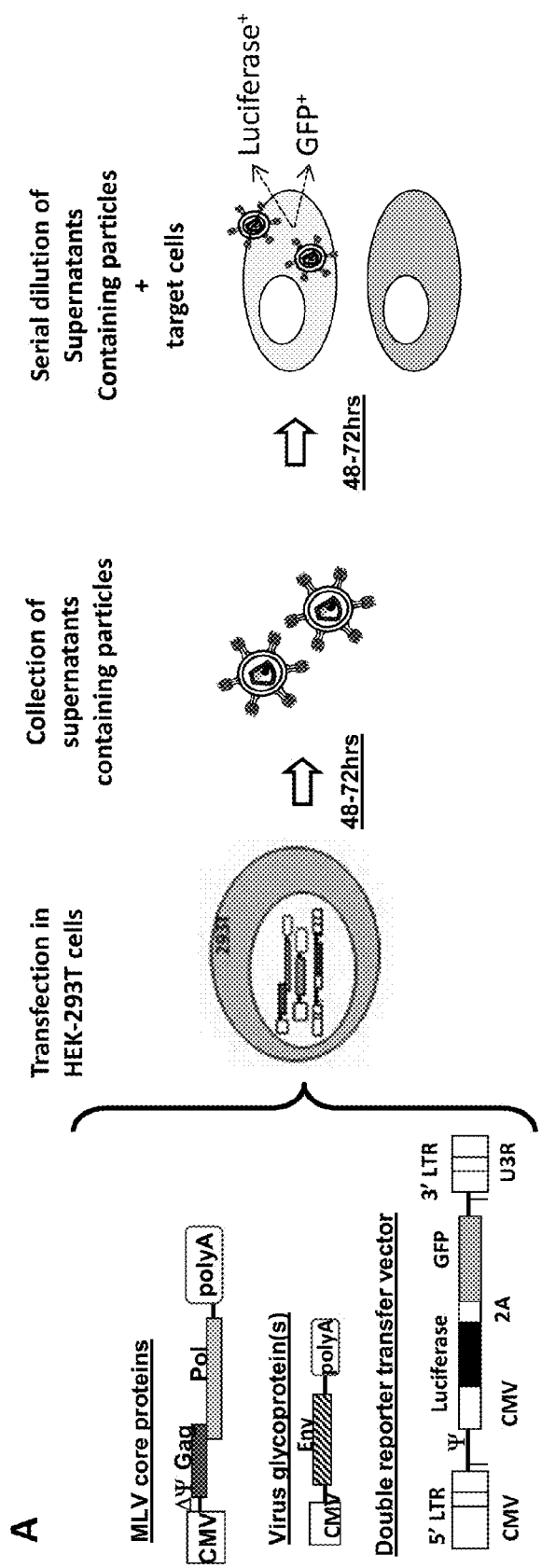
FIG. 6 shows a process for producing VLP and a binding/entry assay using retroviral pseudoparticles that contain a double-reporter MLV-based retroviral vector encoding a polyprotein GFP-Luciferase.
Figure 9:
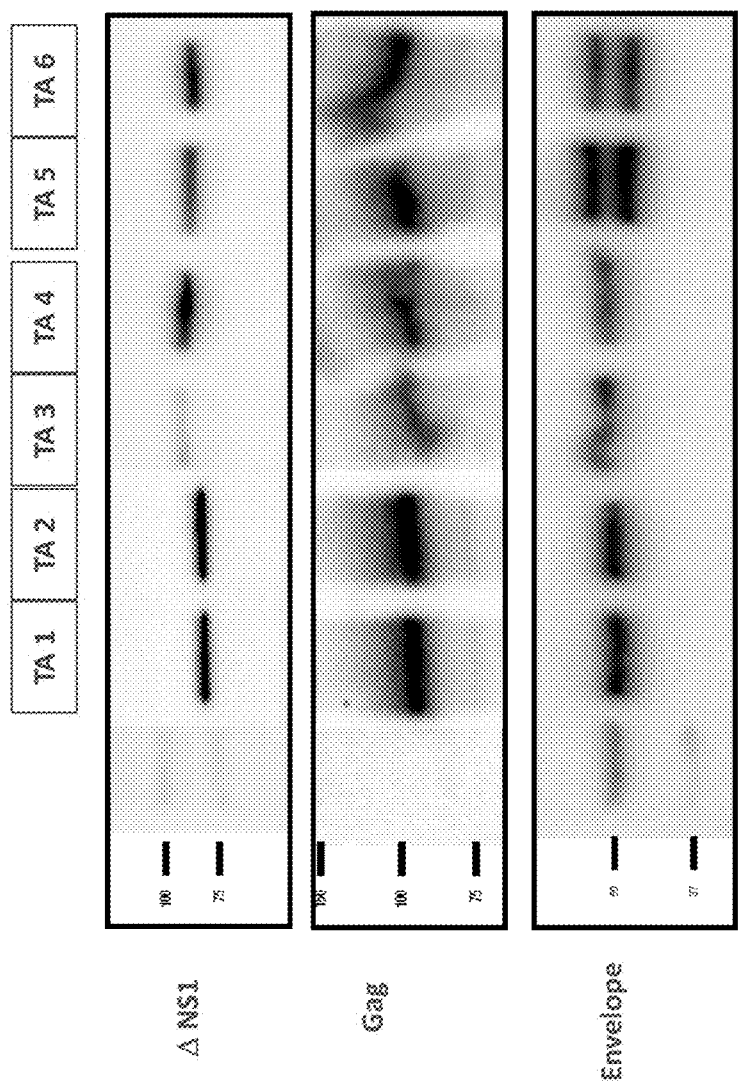
FIG. 9 shows a Western blot analysis of purified bivalent VLPs expressing ZIKV envelope proteins, GAG and ΔNS1.

VLPs in accordance with the present invention may be prepared according to general methodologies known to the skilled person. For example, nucleic acid molecules, reconstituted vectors or plasmids may be prepared using sequences which are known in the art. Such sequences are available from banks, and material may be obtained from various collections, published plasmids, etc. These elements can be isolated and manipulated using techniques well known to the skilled artisan, or available in the art. Various synthetic or artificial sequences may also be produced from computer analysis or through (high throughput) screening of libraries. Recombinant expression of the polypeptides for VLPs requires construction of an expression vector containing a polynucleotide that encodes one or more polypeptide(s). Once a polynucleotide encoding one or more polypeptides has been obtained, the vector for production of the polypeptide may be produced by recombinant DNA technology using techniques known in the art. Expression vectors that may be utilized in accordance with the present invention include, but are not limited to mammalian and avian expression vectors, bacculovirus expression vectors, plant expression vectors (e.g., Cauliflower Mosaic Virus (CaMV), Tobacco Mosaic Virus (TMV)), plasmid expression vectors (e.g., Ti plasmid), among others. An exemplary VLP expression plasmid that can be used to express a ZIKV polypeptide is shown in FIG. 3.

The VLPs of the invention may be produced in any available protein expression system. Typically, the expression vector is transferred to a host cell by conventional techniques and the transfected cells are then cultured by conventional techniques to produce VLPs. In some embodiments, VLPs are produced using transient transfection of cells. In some embodiments, VLPs are produced using stably transfected cells. Typical cell lines that may be utilized for VLP production include, but are not limited to, mammalian cell lines such as human embryonic kidney (HEK) 293, WI 38, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 cells subcloned for growth in suspension culture, Graham et al., J. Gen Virol., 36:59 (1977)); baby hamster kidney cells (BHK, ATCC CCL 10); Chinese hamster ovary cells+/−DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). In some embodiments, cell lines that may be utilized for VLP production include insect (e.g., Sf-9, Sf-21, Tn-368, Hi5) or plant (e.g., Leguminosa, cereal, or tobacco) cells. It will be appreciated in some embodiments, particularly when glycosylation is important for protein function, mammalian cells are preferable for protein expression and/or VLP production (see, e.g., Roldao A et al., 2010 Expt Rev Vaccines 9:1149-76).

It will be appreciated that a cell strain may be chosen which modulates the expression of the inserted sequences, or modifies and processes the gene product in a specific way. Such modifications (e.g., glycosylation) and processing (e.g., cleavage or transport to the membrane) of protein products may be important for generation of a VLP or function of a VLP polypeptide or additional polypeptide (e.g., an adjuvant or additional antigen). Different cells have characteristic and specific mechanisms for post-translational processing and modification of proteins and gene products. Appropriate cell lines or host systems can be chosen to ensure the correct modification and processing of the foreign protein expressed. Generally, eukaryotic host cells (also referred to as packaging cells (e.g., 293T human embryo kidney cells)) which possess appropriate cellular machinery for proper processing of the primary transcript, glycosylation and phosphorylation of the gene product may be used in accordance with the present invention.

VLPs may be purified according to known techniques, such as centrifugation, gradients, sucrose-gradient ultracentrifugation, tangential flow filtration and chromatography (e.g., ion exchange (anion and cation), affinity and sizing column chromatography), or differential solubility, among others. Alternatively, or additionally, cell supernatant may be used directly, with no purification step. Additional entities, such as additional antigens or adjuvants may be added to purified VLPs.

In accordance with the present invention, cells may be transfected with a single expression vector. In some embodiments, a single expression vector encodes more than one element of a VLP (e.g., more than one of structural polyprotein, ZIKV tegument polypeptide, ZIKV glycoprotein, etc.). For example, in some embodiments, a single expression vector encodes two or more elements of a VLP. In some embodiments, a single expression vector encodes three of more elements of a VLP. In an embodiment of the invention, a single expression vector encodes a Gag polypeptide and a ZIKV glycoprotein. In a further embodiment of the invention, a single expression vector encodes a Gag polypeptide, a ZIKV glycoprotein and a ZIKV non-structural protein.

Figure 4:
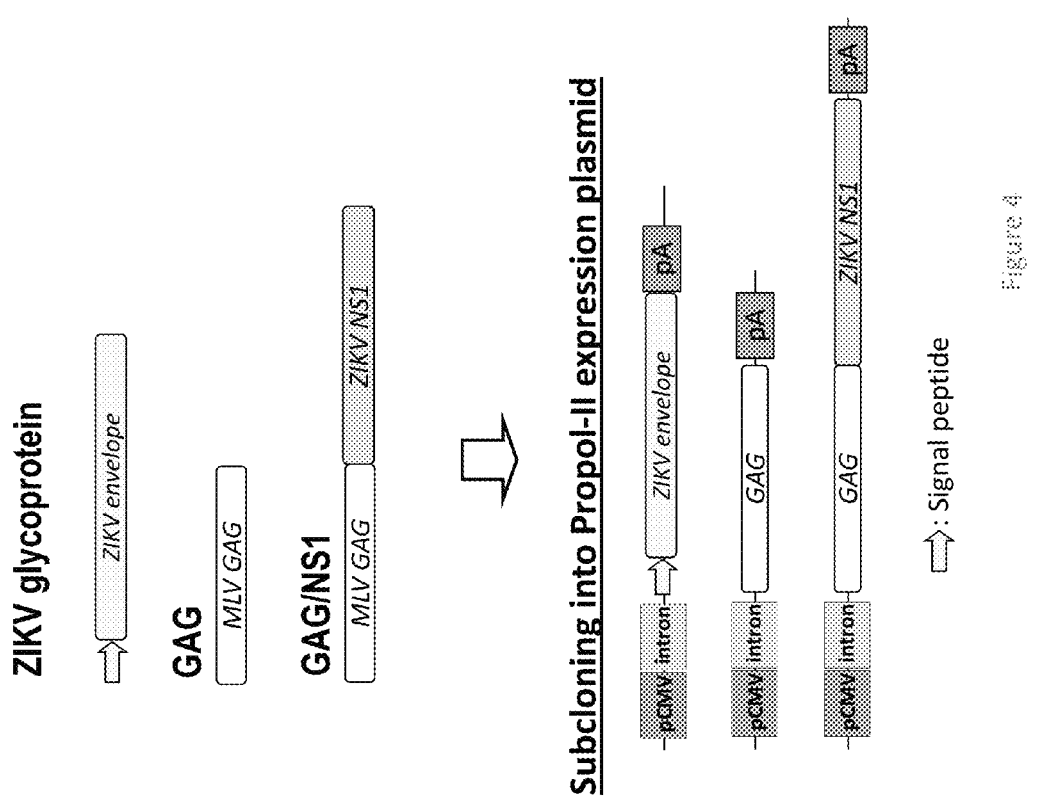

In some embodiments, cells are transfected with two or more expression vectors (see FIG. 4). For example, in some embodiments, cells are transfected with a first vector encoding a Gag polypeptide and a second vector encoding a ZIKV envelope glycoprotein and "monovalent" VLPs comprising a ZIKV envelope glycoprotein are produced. In some embodiments, cells are transfected with a first vector encoding a Gag polypeptide, a second vector encoding a ZIKV envelope glycoprotein and a third vector encoding another ZIKV envelope glycoprotein. In such embodiments, "bivalent" VLPs comprising two ZIKV envelope glycoproteins are produced. In some embodiments, cells are transfected with a first vector encoding a Gag fusion polypeptide encoding a Gag and a ZIKV non-structural protein and a second vector encoding a ZIKV envelope glycoprotein. In such embodiments, "bivalent" VLPs comprising a ZIKV non-structural protein and a ZIKV envelope glycoprotein are produced. In some embodiments, cells are transfected with a first vector encoding a Gag fusion polypeptide encoding a Gag and a ZIKV non-structural protein, a second vector encoding a ZIKV envelope glycoprotein, and a third vector encoding another ZIKV envelope glycoprotein. In some such embodiments, "trivalent" VLPs comprising a ZIKV non-structural protein and two ZIKV envelope glycoproteins are produced. In some embodiments a vector encoding a ZIKV envelope glycoprotein also encodes a second ZIKV glycoprotein.

In some embodiments, monovalent, bivalent, or trivalent VLPs are admixed. For example, in some embodiments, monovalent and bivalent VLPs are admixed to form a trivalent VLP mixture. In some embodiments two monovalent VLPs are admixed to form a bivalent VLP mixture. In one embodiment, a monovalent VLP having the EG variant of the ZIKV E glycoprotein and a second monovalent VLP having the ZIKV ΔNS1 protein are admixed.

The present invention provides pharmaceutical compositions comprising the VLPs described herein and, optionally, further comprising the glycoproteins, glycoprotein variants, non-structural proteins or non-structural protein variants described herein. In some embodiments, the present invention provides a VLP and at least one pharmaceutically acceptable excipient, adjuvant and/or carrier. Such pharmaceutical compositions may optionally comprise and/or be administered in combination with one or more additional therapeutically active substances. The provided pharmaceutical compositions are useful as prophylactic agents (i.e., vaccines) in the prevention of ZIKV infection or of negative ramifications associated or correlated with ZIKV infection.

In some embodiments, pharmaceutical compositions are formulated for administration to humans.

Pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). Suitable excipients include, for example, water, saline, dextrose, sucrose, trehalose, glycerol, ethanol, or similar, and combinations thereof. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention. In some embodiments, pharmaceutical compositions comprise one or more preservatives. In some embodiments, pharmaceutical compositions comprise no preservative.

In some embodiments, a pharmaceutical composition is sufficiently immunogenic as a vaccine (e.g., in the absence of an adjuvant). In some embodiments, immunogenicity of a pharmaceutical composition is enhanced by including an adjuvant. Any adjuvant may be used in accordance with the present invention. A large number of adjuvants are known; a useful compendium of many such compounds is prepared by the National Institutes of Health and can be found (www.niaid.nih.gov/daids/vaccine/pdf/compendium.pdf).
See also Allison, 1998, Dev. Biol. Stand., 92:3-11, Unkeless et al., 1998, Annu. Rev. Immunol., 6:251-281, and Phillips et al., 1992, Vaccine, 10:151-158. Hundreds of different adjuvants are known in the art and may be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.), microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.), oil-emulsion and emulsifier-based adjuvants (e.g., Freund's Adjuvant, MF59 [Novartis], SAF, etc.), particulate adjuvants (e.g., liposomes, biodegradable microspheres, saponins, etc.), synthetic adjuvants (e.g., nonionic block copolymers, muramyl peptide analogues, polyphosphazene, synthetic polynucleotides, etc.) and/or combinations thereof. Other exemplary adjuvants include some polymers (e.g., polyphosphazenes; described in U.S. Pat. No. 5,500,161, Q57, QS21, squalene, tetrachlorodecaoxide, etc.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of VLP formulations for longer than the specified time results in VLP degradation.

A pharmaceutical composition in accordance with the invention may be prepared, packaged, and/or sold as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject and/or depending upon the route by which the composition is to be administered. By way of example, the composition may comprise between 0.1% and 100% (w/w) active ingredient.

Provided compositions and methods of the present disclosure are useful for prophylaxis of ZIKV infection in a subject, including human adults and children. In general however they may be used with any animal. If desired, the methods herein may also be used with farm animals, such as ovine, avian, bovine, porcine and equine breeds. For the purposes of the present disclosure, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Compositions described herein will generally be administered in such amounts and for such a time as is necessary or sufficient to induce an immune response. Dosing regimens may consist of a single dose or a plurality of doses over a period of time. The exact amount of an immunogenic composition (e.g., VLP) to be administered may vary from subject to subject and may depend on several factors. Thus, it will be appreciated that, in general, the precise dose used will depend not only on the weight of the subject and the route of administration, but also on the age of the subject. In certain embodiments a particular amount of a VLP composition is administered as a single dose. In certain embodiments, a particular amount of a VLP composition is administered as more than one dose (e.g., 1-3 doses that are separated by 1-12 months).

In some embodiments, a provided composition is administered in an initial dose and in at least one booster dose. In some embodiments, a provided composition is administered in an initial dose and two, three or four booster doses. In some embodiments, a provided composition is administered in an initial dose and in at least one booster dose about one month, about two months, about three months, about four months, about five months, or about six months following the initial dose. In some embodiments, a provided composition is administered in a second booster dose about six months, about seven months, about eight months, about nine months, about ten months, about eleven months, or about one year following the initial dose. In some embodiments, a provided composition is administered in a booster dose every 1 year, 2 years, 3 years, 4 years, 5 years, 6 years, 7 years, 8 years, 9 years, or 10 years.

In certain embodiments, provided compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for peroral delivery, oral delivery, intranasal delivery, buccal delivery, sublingual delivery, transdermal delivery, transcutaneous delivery, intraperitoneal delivery, intravaginal delivery, rectal delivery or intracranial delivery.

In some embodiments, upon administration to a subject, provided VLPs induce a humoral immune response in the subject. In some embodiments, the humoral immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 28 months, at least about 32 months, at least about 36 months, at least about 40 months, at least about 44 months, at least about 48 months, or longer.

In some embodiments, upon administration to a subject, provided VLPs induce a cellular immune response in the subject. In some embodiments, the cellular immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

EXAMPLES

The following examples describe some exemplary modes of making and practicing certain compositions that are described herein. It should be understood that these examples are for illustrative purposes only and are not meant to limit the scope of the compositions and methods described herein.

Example 1: Construction of DNA Expression Plasmids

This Example describes development of expression plasmids and constructs for expression of recombinant ZIKV gene sequences. A standard expression plasmid generally consists of a promoter sequence of mammalian origin, an intron sequence, a PolyAdenylation signal sequence (PolyA), a pUC origin of replication sequence (pUC—pBR322 is a colEl origin/site of replication initiation and is used to replicate plasmid in bacteria such as *E. Coli* (DH5a)), and an antibiotic resistance gene as a selectable marker for plasmid plaque selection. Within the plasmid following the intron are a variety of restriction enzyme sites that can be used to splice in a gene or partial gene sequence of interest.

The Propol II expression plasmid contains the pHCMV (early promoter for HCMV), a Beta-Globin Intron (BGL Intron), a rabbit Globin polyAdenylation signal sequence (PolyA), a pUC origin of replication sequence (pUC—pBR322 is a colEl origin/site of replication initiation and is used to replicate plasmid in bacteria such as *E. coli* (DH5a)), and an ampicillin resistance gene β-lactamase (Amp R—selectable marker for plasmid confers resistance to ampicillin (100 μg/ml) (see FIG. 3).

To develop a Gag MMLV expression construct ("MLV-Gag"), a complementary DNA (cDNA) sequence encoding a Gag polyprotein of MMLV (Gag without its C terminus Pol sequence) (SEQ ID NO: 3) was cloned in a Propol II expression vector. To develop all of ZIKV expression constructs, each of the following sequences:

i) full-length sequence of ZIKV—prME (SEQ ID NO: 6);
ii) prMuE (prME where amino acid 215 from the prM has been mutated to prevent furin cleavage) (SEQ ID NO: 9);
iii) ZIKV-EG (VSV-G TMD/Cyto) (SEQ ID NO: 12); or
iv) ZIKV-prME156 (where amino acid 156 of the E sequence has been mutated to prevent N-glycosylation in position E154) (SEQ ID NO: 15) codon-optimized for human expression (GenScript), was cloned in a Propol II expression vector. To develop the modified ZIKV-EG expression construct, a truncated sequence of ZIKV-prME encoding only the signal peptide of prM and the extracellular portion of E peptide was fused together with the transmembrane and cytoplasmic portions of VSV-G. The codon-optimized sequence for ZIKV-prME was exposed to directed mutagenesis to give codon-optimized ZIKV-prMuE or ZIKV-prME156.

DNA plasmids were amplified in competent *E. coli* (DH5a) and purified with endotoxin-free preparation kits according to standard protocols.

Example 2: Production of Virus-Like Particles

This Example describes methods for production of virus-like particles containing various recombinant ZIKV antigens described in Example 1.

293 SF-3F6 cell line derived from HEK 293 cells are a proprietary suspension cell culture grown in serum-free chemically defined media (CA 2,252,972 and U.S. Pat. No. 6,210,922). HEK 293 SF-3F6 cells were scaled up in shaker flasks at 37° C., 5% $CO_2$ at a speed of 80 rpm and subsequently seeded in a bioreactor using HyQSF4 Transfx293 media supplemented with L-glutamine (GE Bioscience) to obtain a target cell density of 0.9 to 1.2 million cells/ml and high viability (>90%). The cells were co-transfected at cell density of about ~1 million cells/ml with different ratios of plasmids encoding ZIKV envelope polypeptides, plasmids encoding Gag and using high quality polyethyleneimine (PEIpro™) as transfection agent. The DNA plasmids and transfection agent were prepared in OptiPRO SFM medium (GE Biosciences). The bioreactor was monitored daily (~24 hrs and 48 hrs post transfection) and cell density, viability and cell diameters recorded. The production broth was harvested at 48 hrs post transfection.

Total protein was determined on an aliquot by a Bradford assay quantification kit (BioRad). The Bradford Protein assay is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible color change. A spectrophotometer was used to measure the absorbance of the sample and Bradford Protein Reagent dye at 595 nm.

Example 3: Relative Yields of GAG VLPs

The relative yields of ZIKV eVLP compositions prepared as described in Example 2 were determined (Table 1). Data suggest that all versions of ZIKV eVLPs were expressed.

Residual DNA was quantified by the Quant-iT Picogreen assay. Lambda DNA standards were prepared by dilution of 100 μg/mL commercial stock with 1× Tris-EDTA (TE) buffer. Unknown samples were diluted (at least 1:2 v/v) with 1×TE buffer prior to analysis. 100 μL of each standard or sample was added to the microplate in duplicates followed by 100 μL of the Picogreen reagent to each well, and the plate was incubated for 5 min at room temperature in the dark. The fluorescence intensity was measured (485 nm excitation, 535 nm emission) using a microplate reader. A linear standard curve was prepared by plotting the average blank-corrected emission measurement for each lambda DNA standard versus its concentration. The standard curve was used to determine the residual nucleic acid concentration of the unknown sample.

Concentration of Gag was determined using a GAG sELISA assay based on the common Sandwich ELISA theme. p30 Gag protein molecules were captured from detergent-treated VLP samples loaded to wells of a microtiter plate coated with Anti-MuLV p30 mouse monoclonal antibody, clone R187. After washing the plate, goat polyclonal antibody to MuLV p30 was added to bind the captured protein. A HRP conjugate rabbit anti-goat IgG HRP conjugate was added to quantify immobilized antibody-enzyme conjugates by monitoring horseradish peroxidase activities in the presence of the substrate. The results were compared to a standard recombinant protein curve. The data fitting and analysis were performed with Softmax Pro 5, using a four-parameter fitting algorithm.

TABLE 1

| Test Articles | ZIKV plasmid (μg/ml) | Total Protein (BCA) (mg/mL) | [Gag] (μg/mL) |
| --- | --- | --- | --- |
| prME | 0.05 | 2.77 | 563 |
| prME | 0.2 | 1.57 | 280 |
| prME | 0.8 | 4.19 | 38 |
| prMuE | 0.05 | 2.62 | 741 |
| prMuE | 0.2 | 2.29 | 97 |
| prMuE | 0.8 | 0.37 | 44 |
| prME156 | 0.05 | 2.40 | 518 |
| prME156 | 0.2 | 1.89 | 262 |
| prME156 | 0.8 | 3.40 | 51 |
| E-G | 0.05 | 4.88 | 160 |
| E-G | 0.2 | 3.51 | 491 |
| E-G | 0.8 | 10.70 | ND |
| no ZIKV envelope | — | 3.74 | 1192 |

ZIKV VLPs:
ZIKV prME = native prME protein
ZIKV prMuE = furin cleavage site mutation in M
ZIKV prME156 = mutation in E156, inducing no N-glycosylation
ZIKV E-G = M polypeptide removed, TMD/Cyt from E replaced by VSV TMD/Cyt
Bold font: values outside of standard range
N/D: not determined Example 4: Western Blot of ZIKV VLPs with ZIKV E Protein The VLPs shown in Table 2 were prepared for the purpose of analyzing proteins by Western Blot.

TABLE 2

| TA | VLP description | ZIKA plasmid [μg/ml] | GAG plasmid [μg/ml] | Cell Line | Transfection (h) |
| --- | --- | --- | --- | --- | --- |
| 1 | prME VLP ZIKV unmodified sequence plasmid | 0.05 | 0.4 | HEK 293 Suspension | 48 |
| 2 | prMuE VLP furin cleavage site plasmid | 0.05 | | | |
| 3 | prM-E156 no n-glycosylation | 0.05 | | | |
| 4 | E-G-VSV M polypeptide removed, VSV transmembrane domain | 0.2 | | | |

Proteins were resolved by SDS-PAGE (4-20% polyacrylamide Mini-PROTEAN® TGX Precast gel from Bio-Rad) and transferred onto a PVDF membrane. The membrane was blocked with 5% skim milk in Tris-buffered saline containing 0.05% Tween-20. The ZIKV E proteins bands were probed with monoclonal anti-Flavivirus group antigen clone D1-4G2-4-15, ascites (Cat# MAB10216, EMB Millipore) at 1/2500 dilution followed by incubation with secondary antibody, HRP-conjugated Goat Anti-Mouse IgG (Bethyl, cat#A90-131P-26) at a 1/5000 dilution. Blots were developed using Clarity Western ECL Substrate (BIORAD) and analyzed on a Molecular Imager (ChemiDOC XRS with Imaging system, BIORAD) for the appropriate time (few seconds).

Figure 5:
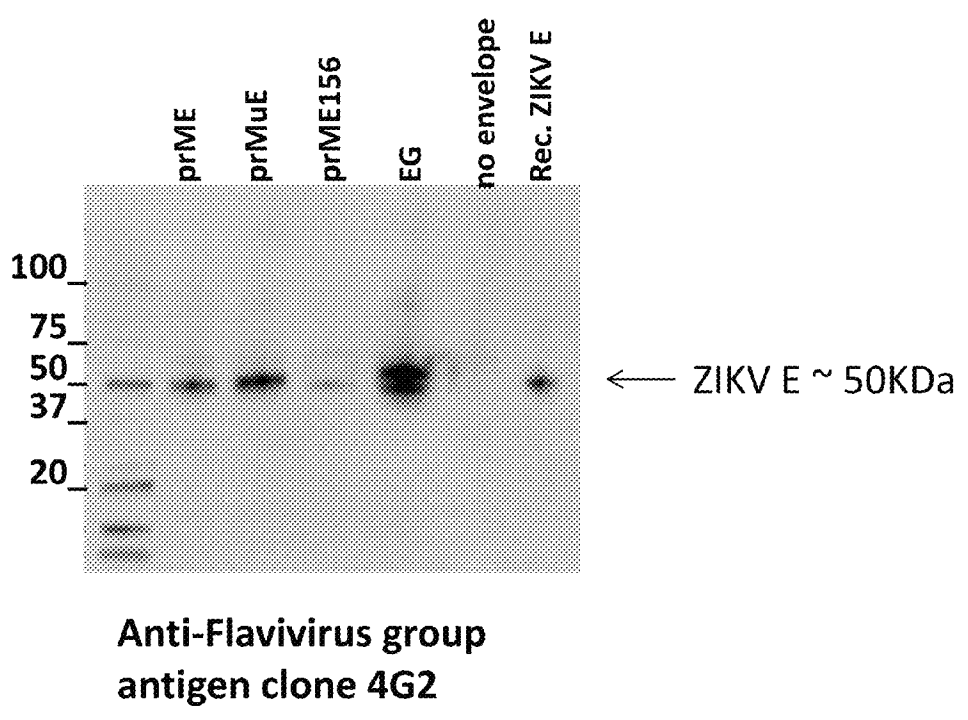

The results are shown in FIG. 5. As can be seen in the blot, a strong signal shows the presence of protein of approximately 50 kiloDaltons, which corresponds to the molecular weight of the ZIKV E glycoprotein. Three different ZIKV envelope protein constructs (prME, prMuE, and EG-VSV) show a significant presence of the ZIKV E glycoprotein. The fourth ZIKV VLP construct (prME156—SEQ ID NO: 13) shows only a trace amount of the ZIKV E glycoprotein and therefore it was not included in the animal study that follows in Example 6.

Example 5: Visualization of Monovalent ZIKV E Protein Virus Like Particles Using Electron Microscopy Cryo-transmission electron microscopy ("cryoTEM") was conducted on VLPs containing the following two ZIKV surface glycoproteins, which were prepared as described in Example 2:
prME (SEQ ID NO: 6)—Gag (0.5 μg/ml ZIKV plasmid)
prMuE (SEQ ID NO: 9)—Gag (0.5 μg/ml ZIKV plasmid)
Each sample was preserved in vitrified ice supported by holey carbon films on 400-mesh copper grids. Each sample was prepared by applying a 3 μl drop of sample suspension to a cleaned grid, blotting away with filter paper, and immediately proceeding with vitrification in liquid ethane. Grids were stored under liquid nitrogen until transferred to the electron microscope for imaging. Electron microscopy was performed using an FEI Tecnai T12 electron microscope, operating at 120 keV equipped with an FEI Eagle 4k×4k CCD camera. Vitreous ice grids were transferred into the electron microscope using a cryostage that maintains the grids at a temperature below −170° C. Samples were imaged undiluted.

FIG. 7 shows a cryoTEM image for each sample at a magnification of 110,000×. As can be seen from FIG. 7, the prME (SEQ ID NO: 6)—Gag (0.5 mg/ml ZIKV plasmid) sample and the prMuE (SEQ ID NO: 9)—Gag (0.5 mg/ml ZIKV plasmid) sample both clearly show the production of round VLP structures. Overall, particles were mostly spherical in shape that ranged in size from 110-160 nm across in both samples and did not appear spiked. Also seen in the samples were elongated particles with a multi-lobed appearance; these ranged from 200 nm to >1,600 nm for both samples (image not shown). Particles contained three layers: a dense, textured 50-70 nm diameter core surrounded by a second layer that increased the particle diameter to 80-100 nm, and a third layer that further increased the diameter to 100-160 nm (size estimates apply only to spherical particles as sizes vary greatly for elongated particle). Surrounding each layer appeared to be ~8 nm liposomal bilayers. Very few particles appeared to have broken, segmented, or incomplete inner layers. Overall, cryoTEM images provide valuable morphological insight into the structure of ZIKV VLPs, and further confirm successful particle creation.

Negative staining transmission electron microscopy ("nsTEM") was conducted on the following four VLPs (each VLP type referred to as a test article: "TA") prepared as described in Example 2:

prME (SEQ ID NO: 6)—Gag (0.05 μg/ml ZIKV plasmid) ("TA2")

prMuE (SEQ ID NO: 9)—Gag (0.05 μg/ml ZIKV plasmid) ("TA1")

prME156 (SEQ ID NO: 15)—(0.05 μg/ml ZIKV plasmid) ("TA4")

EG VSV—(SEQ ID NO: 12)—(0.2 μg/ml ZIKV plasmid) ("TA3")

Each sample was mixed with a solution containing calibrated polystyrene latex beads with size comparable to the VLP particles. The VLP containing samples were loaded onto grids by direct sedimentation using a Beckmann Airfuge ultracentrifuge. The circular grids were immersed into the sample solution in a small eppendorf tube and centrifuged using A-100 fixed angle microrotor at 120,000×g for 45 min. The grids were dried by blotting with bibulous paper. The sample on the grid was stained by adding a drop of 3% phosphotungstic acid (PTA) on the grid. The grids with the sample were mounted onto the TEM and examined using a voltage of 75 kV and final magnification of 20,000× or 40,000×. Once the appropriate dilution was achieved, each sample was analyzed in triplicate (i.e., same sample is analyzed on three different grids).

FIG. 9 shows nsTEM images for each of the four samples above. As the images show, each of the samples contained some minor debris and membranes, but overall 85%-99% of VLPs from all samples were in good condition. Particle counts were high: TA1-$2.49\times10^{11}$, TA2-$2.65\times10^{11}$, TA3-$3.02\times10^{10}$ and TA4-$3.05\times10^{11}$.

Example 6: In Vivo Potency of Monovalent ZIKV VLPs in Mice

Two studies were conducted to evaluate the in vivo potency of select monovalent ZIKV VLPs in mice.

The first study was an antibody study conducted using ELISA in accordance with the following protocol. Each animal was dosed with 50 μg of Gag and three of the test articles described in Example 5. The test articles were adjuvanted with alum phosphate. A summary of the study is shown below in Table 3.

TABLE 3

| Test Article Description | Production ZIKV plasmid/ GAG ratio | Adjuvant (Alum) | Antigen dose (μg GAG/ mouse) | Immunization Schedule (weeks) | Route of Immunization | Bleeding | Analysis |
|---|---|---|---|---|---|---|---|
| prM-E (non-modified) | 0.05/0.4 | + | 50 | 0, 4 | IP | 0<br>2 wk<br>4 wk | Ab Binding Titre to ZIKV E |
| prM-E (furin cleavage) | 0.05/0.4 | + | 50 | 0, 4 | | 8 wk<br>12 wk | |
| EG-VSV (E protein with TM/Cyt from VSV-G) | 0.2/0.4 | + | 50 | 0, 4 | | | |

Serum from the study was analyzed by antibody binding titres to recombinant ZIKV E protein as follows. A coating buffer was prepared by dissolving 2.11 g of sodium bicarbonate in 1 L of type 1 water (25 mM sodium bicarbonate), adjusting pH to 9.7 with 1 M NaOH and filtering through 0.22 μm filter, and store at room temperature. ZIKV Recombinant Envelope Protein (Meridian Life Sciences, Cat # R01635, 1.9 mg/mL) was diluted to 1.26 μg/mL (1/1500 dilution) in coating buffer. 50 μL of coating solution was added to appropriate wells of half-area 96-well, flat bottom plates (Grenier Bio-One, Cat #675061). Plates were covered and incubated overnight at 4° C. ELISA wash buffer (EWB) was prepared by dissolving 1 packet of 10×PBS powder (Fisher, Cat # BP665-1) into 4 L of type 1 water, adding 5 mL of Tween 20 (Sigma, Cat # P7949) and mixing for at least 20 minutes, and make volume up to 10 L with type 1 water. Blocking solution/sample diluent was prepared using 1% BSA (w/v) in EWB. The coating solution was decanted and 150 μL of cold blocking solution was added to each well. The samples were incubated at 37° C. for 1 hr. Wash plates were washed using a plate washer.

Serum dilutions were prepared in sample diluent (1% BSA in EWB). Dilutions of mouse anti-flavivirus group antigen mAb clone D1-4G2-4-15 (EMD Millipore, Cat # MAB10216) in sample diluent, were prepared as a positive control. 50 μL of diluted sample and positive control were added to applicable wells, and incubated at 37° C. for 1.5 hours. Plates were washed using plate washer. The detection antibody (goat x-mouse IgG-Fc Fragment HRP conjugate antibody (Bethyl, Cat # A90-131P, 1 mg/mL)) was diluted 1/5000 in sample diluent: 5 neat antibody+25 mL sample diluent. 50 μL of diluted detection antibody was added to each well, and incubated at 37° C. for 1.5 hours. Plates were washed using a plate washer. 50 μL of room temperature TMB Conductivity One Component HRP Microwell Substrate (SurModics, Cat # TMBC-1000-01) was added into each well, and incubated at room temperature for 6 minutes (protected from light). 50 μL of room temperature 450 nm Liquid Nova-Stop Solution for TMB Microwell Substrates (SurModics, Cat # NSTP-1000-01) was added into each well. OD450 nm was measured by plate reader.

The mouse antibody binding titres showed that each of the three test article VLPs described above in Table 4 raised antibodies to the ZIKV E protein. The end point titres for each of the three test articles are shown below in Table 4.

TABLE 4

| prM-E | prMu-E | EG-VSV | Positive Control |
|---|---|---|---|
| 100 | 100 | 12500 | 16000 |

As can be seen in Table 5, the VLP containing the EG VSV version of the ZIKV envelope glycoprotein (SEQ ID NO: 12), showed a substantially higher endpoint titre than the other VLPs. As a result, this VLP appears to be the most immunogenic of the three monovalent VLPs tested.

The significantly higher endpoint titre showed by the EG-VSV version of the ZIKV VLP was unexpected in view of reports of DNA vaccines to ZIKV which indicated that wild type ZIKV glycoprotein elicited the most antigenic response. As well, it was unexpected in view of another study conducted by the inventors using a VLP vaccine against a different virus, respiratory syncytial virus (RSV). A monovalent VLP expressing the RSV-F protein and a modified version thereof was prepared. Briefly, VLPs were prepared in accordance with the method described in Example 2, however instead of plasmids encoding ZIKV proteins, RSV-F expression constructs ("RSV-F") were used which expressed full-length wild type RSV-F protein and a modified version of the RSV-F wherein the transmembrane component was exchanged for the transmembrane sequence from VSV ("RSV-Fg (VSV-G)"). The RSV-F expression constructs were produced by cloning the RSV-F sequences into the Propol II expression vectors using the method described in Example 1. The sequence of the expression vector encoding the wild type RSV-F protein is SEQ ID NO: 23. The sequence of the expression vector encoding the RSV-Fg (VSV) protein is SEQ ID NO: 24. The resulting VLPs were tested in mice in accordance with the method described in this Example 5. Serum from the study was analyzed by antibody binding titres to RSV-F protein using the method described above, except that the Palivizumab antibody produced by Synagis was added to evaluate whether the mouse serum antibodies can compete with the Palivizumab antibody. The results are shown below in Table 5 in comparison with the results from ZIKV from Table 4.

TABLE 5

| Virus | Wild Type Glycoprotein (End point titre) | VSV Modified Glycoprotein (End Point titre) |
|---|---|---|
| ZIKV | 100 | 12500 |
| RSV | 2560 | No antibodies detected |

As can be seen in Table 5, the results shown by the ZIKV VLPs were the opposite to those seen in the RSV VLPs. Specifically, VLPs containing an RSV surface antigen modified to incorporate a transmembrane domain from VSV showed no antigenicity (in contrast to the clear antigenicity shown by VLPs containing the wild type RSV antigen) whereas the ZIKV E G VSV construct showed significantly higher immunogenicity than the VLPs containing the ZIKV wild type antigen.

The second study conducted to evaluate the in vivo potency of select monovalent ZIKV VLPs in mice was a virus plaque-reduction neutralization assay (PRNA) as first described in the 1950s, and later adapted to DENV (Russell et al., 1967: 99, 291-296). PRNA measures the biological parameter of in vitro virus neutralization and is currently the most serologically virus-specific test among flaviviruses, correlating well to serum levels of protection from virus infection. Newer tests measuring virus neutralization are being developed, but PRNA currently remains the laboratory standard.

The basic design of the assay allows for virus-antibody interaction to occur in a microtiter plate, and measurement of antibody effects on viral infectivity by plating the mixture on virus-susceptible cells. The cells are overlaid with a semi-solid media that restricts spread of progeny virus. Each virus that initiates a productive infection produces a localized area of infection (a plaque), that can be detected in a variety of ways. Plaques are counted and compared back to the starting concentration of virus to determine the percent reduction in total virus infectivity. In the PRNA, the serum specimen being tested is subjected to serial dilutions prior to mixing with a standardized amount of virus. The concentration of virus is held constant such that, when added to susceptible cells and overlaid with semi-solid media, individual plaques can be discerned and counted. In this way, PRNA end-point titers can be calculated for each serum specimen at any selected percent reduction of virus activity.

Even though a given undiluted serum specimen may neutralize a large amount of virus, e.g., $1 \times 10^7$ plaque-forming units (PFUs), in nature the virus dose delivered by a mosquito during a blood meal rarely exceeds $1 \times 10^4$ PFUs.

PRNA assays were conducted by Southern Research of Birmingham, Ala. using the Puerto Rican strain of ZIKV, PRVABC59, 110 PFU per well. Negative control and testing sera samples started at 1 in 10 diluted, following 4-fold dilutions up to 1 in 10240 (usually to catch the titer of positive control). Positive control dilutions started at 1 in 100 a priori diluted, then followed by 4-fold dilution. Briefly, Vero cells seeded at a concentration of approximately 3×105 cells/ml in 24 well plates were incubated for approximately 24 hours. On the day of assay, the input virus and serially dilated serum samples were mixed and incubated for 1 hour at 1 h at 37+1.0 in the dilution plate. Supernatant from cell-seeded 24 well plates was decanted, then 100 μl of virus/serum mixture was transferred from the dilution plate to the cells. After 1 hour adsorption, agarose-containing overlay media was added and plates were incubated at 37+1° C., 5% CO2 for 3 days. The cells were fixed and stained using crystal violet solution and plaques were counted visually. The neutralizing antibody titer was expressed as the highest test serum dilution for which the virus infectivity is reduced by 50%.

The PRNA data are summarized below in Table 6.

TABLE 6

| VIP | Sample Description | PRNT$_{50}$ Titer (PFU/mL) |
|---|---|---|
| Applicant's controls | Negative Control non-immunized mice | 13 |
| | Human anti-Zika serum | 532 |
| prM-E (SEQ ID NO: 6) (non-modified) | Pooled Group 1 (#1-#8) | 25 |
| prMu-E (SEQ ID NO: 9) (Δfurin cleavage) | Pooled Group 2 (#9-#16) | 31 |
| prM-E156 (SEQ ID NO: 15) (Δ glycolysation) | Pooled Group 3 (#17-#24) | 29 |
| E-G (SEQ ID NO: 12) (E protein with TM/Cyt from VSV-G) | Individual Group 4 #25 | 44 |
| | Individual Group 4 #26 | 55 |
| | Individual Group 4 #27 | 53 |
| | Individual Group 4 #28 | 52 |
| | Individual Group 4 #29 | <20 |
| | Individual Group 4 #30 | 40 |
| | Individual Group 4 #31 | 23 |
| | Individual Group 4 #32 | 37 |
| Laboratory controls | Positive Control (Internal Serum) | 612 |
| | Negative Control (Internal Serum) | <10 |

As shown in Table 6, the VLPs of the invention demonstrated neutralizing antibody activity. However, the strongest neutralizing activity was observed in the VLP expressing E-G (SEQ ID No: 12)

Example 7: Production of Monovalent ZIKV NS1 VLPs

This Example describes methods for production of virus-like particles containing the ZIKV NS1 protein or a modified version thereof (the ΔNS1 construct). The monovalent VLPs described in this Example 7 do not contain the ZIKV protein E surface antigens. The NS1 protein and the ΔNS1 protein were fused to Gag to create a fusion protein that can be expressed during assembly of the VLP. The NS1 Gag fusion protein has SEQ ID NO: 16 and the ΔNS1 Gag fusion protein has SEQ ID NO: 19. Plasmids expressing the fusion proteins were prepared as described in Example 1 using the codon optimized sequences, specifically SEQ ID NO: 18 for NS1 GAG and SEQ ID NO: 25 for ΔNS1 GAG.

293 SF-3F6 cell line derived from HEK 293 cells are a proprietary suspension cell culture grown in serum-free chemically defined media (CA 2,252,972 and U.S. Pat. No. 6,210,922). HEK 293 SF-3F6 cells were scaled up in shaker flasks at 37° C., 5% $CO_2$ at a speed of 80 rpm and subsequently seeded in a bioreactor using HyQSF4 Transfx293 media supplemented with L-glutamine (GE Bioscience) to obtain a target cell density of 0.9 to 1.2 million cells/ml and high viability (>90%). The cells were co-transfected at cell density of about ~1 million cells/ml with different ratios of plasmids encoding either the NS1 GAG fusion protein or the ΔNS1 GAG fusion protein and using high quality polyethyleneimine (PEIpro™) as transfection agent. The DNA plasmids and transfection agent were prepared in OptiPRO SFM medium (GE Biosciences). The bioreactor was monitored daily (~24 hrs and 48 hrs post transfection) and cell density, viability and cell diameters recorded. The production broth was harvested at 48 hrs post transfection.

Total protein was determined on an aliquot by a Bradford assay quantification kit (BioRad). The Bradford Protein assay is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible color change. A spectrophotometer was used to measure the absorbance of the sample and Bradford Protein Reagent dye at 595 nm.

Concentration of Gag was determined using a Gag sELISA assay based on the common Sandwich ELISA theme. p30 Gag protein molecules were captured from detergent-treated VLP samples loaded to wells of a micro-titer plate coated with Anti-MuLV p30 mouse monoclonal antibody, clone R187. After washing the plate, goat polyclonal antibody to MuLV p30 was added to bind the captured protein. A HRP conjugate rabbit anti-goat IgG HRP conjugate was added to quantify immobilized antibody-enzyme conjugates by monitoring horseradish peroxidase activities in the presence of the substrate. The results were compared to a standard recombinant protein curve. The data fitting and analysis were performed with Softmax Pro 5, using a four-parameter fitting algorithm. Following transfection, samples were visualized using nsTEM as described above in Example 5 and the number of particles per ml was determined.

Following transfection with the plasmid expressing the NS1 Gag fusion protein (SEQ ID NO: 16), all cells died shortly after transfection. Table 8 shows the total protein content and the Gag concentration in the samples prepared using NS1 Gag fusion protein (SEQ ID NO: 16) using three different concentrations of plasmid. As shown in Table 7, the amount of Gag produced was negligible. No particles were observed using nsTEM.

TABLE 7

| Transfection sample (with concentration of plasmid) | [Total Protein] by BCA (μg/mL) | [Gag] by ELISA (μg/mL) |
|---|---|---|
| NS1 full length/Gag eVLP 0.05 μg/mL | 622.8 | ND |
| NS1 full length/Gag eVLP 0.2 μg/mL | 883.9 | 3.589 |
| NS1 full length/Gag eVLP 0.8 μg/mL | 2352.7 | 9.284 |

Following transfection with the plasmid expressing the ΔNS1 Gag fusion protein (SEQ ID NO: 19), cell death was not observed. Table 8 shows the total protein content and the Gag concentration in the samples prepared using ΔNS1 Gag fusion protein (SEQ ID NO: 19) using different concentrations of plasmid. As shown in Table 8, Gag was produced in samples wherein the plasmid concentration was 0.2-0.4 μg/mL. The production of VLP particles was confirmed by nsTEM as shown in Table 8.

TABLE 8

| VLP and concentration of Plasmid | Gag/ΔNS1 [0.05 μg/mL] | Gag/ΔNS1 [0.1 μg/mL] | Gag/ΔNS1 [0.2 μg/mL] | Gag/ΔNS1 [0.4 μg/mL] | Gag/ΔNS1 [1.5 μg/mL] |
|---|---|---|---|---|---|
| [Total Protein] by BCA (μg/mL) | 1257 | 920.5 | 2563 | 2563 | 4937 |
| [Gag] by ELISA (μg/mL) | ND | 3.72 | 199.9 | 160.3 | 7.23 |
| nsTEM (particles/mL) | NT | NT | $6.44 \times 10^{11}$ | $6.44 \times 10^{10}$ | NT |

Example 8: Production of Bivalent VLPs

This Example describes methods for production of virus-like particles containing the ZIKV protein E antigens described in Example 1 and a second antigen, the modified ΔNS1 protein. The ΔNS1 protein was fused to Gag to create a fusion protein that is expressed during assembly of the VLP. The ΔNS1 GAG fusion protein was SEQ ID NO: 19. Plasmids expressing the fusion proteins were prepared as described in Example 1 using the codon optimized sequence SEQ ID NO: 25 for ΔNS1 GAG.

293 SF-3F6 cell line derived from HEK 293 cells are a proprietary suspension cell culture grown in serum-free chemically defined media (CA 2,252,972 and U.S. Pat. No. 6,210,922). HEK 293 SF-3F6 cells were scaled up in shaker flasks at 37° C., 5% $CO_2$ at a speed of 80 rpm and subsequently seeded in a bioreactor using HyQSF4 Transfx293 media supplemented with L-glutamine (GE Bioscience) to obtain a target cell density of 0.9 to 1.2 million cells/ml and high viability (>90%). The cells were co-transfected at cell density of about ~1 million cells/ml with different ratios of plasmids encoding ZIKV envelope polypeptides (shown below) and plasmids encoding the ΔNS1 GAG fusion protein and using high quality polyethyleneimine (PEIpro™) as transfection agent. The DNA plasmids and transfection agent were prepared in OptiPRO SFM medium (GE Biosciences). The bioreactor was monitored daily (~24 hrs and 48 hrs post transfection) and cell density, viability and cell diameters recorded. The production broth was harvested at 48 hrs post transfection.

Total protein was determined on an aliquot by a Bradford assay quantification kit (BioRad). The Bradford Protein assay is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible color change. A spectrophotometer was used to measure the absorbance of the sample and Bradford Protein Reagent dye at 595 nm.

Concentration of Gag was determined using a Gag sELISA assay based on the common Sandwich ELISA theme. p30 Gag protein molecules were captured from detergent-treated VLP samples loaded to wells of a microtiter plate coated with Anti-MuLV p30 mouse monoclonal antibody, clone R187. After washing the plate, goat polyclonal antibody to MuLV p30 was added to bind the captured protein. A HRP conjugate rabbit anti-goat IgG HRP conjugate was added to quantify immobilized antibody-enzyme conjugates by monitoring horseradish peroxidase activities in the presence of the substrate. The results were compared to a standard recombinant protein curve. The data fitting and analysis were performed with Softmax Pro 5, using a four-parameter fitting algorithm. Following transfection, samples were visualized using nsTEM as described above in Example 5 and the number of particles per ml was determined.

Table 9 shows the total protein content and the Gag concentration in six samples prepared using the following ZIKV protein E antigen constructs co-transfected with the Gag/ΔNS1 fusion protein (SEQ ID NO: 19):

1. prME (SEQ ID NO: 6)—Gag/ΔNS1 (0.05/0.2 μg/ml) ("TA1")
2. prME (SEQ ID NO: 6)—Gag/ΔNS1 (0.05/0.4 μg/ml) ("TA2")
3. prMuE (SEQ ID NO: 9)—Gag/ΔNS1 (0.05/0.2 μg/ml) ("TA3")
4. prMuE (SEQ ID NO: 9)—Gag/ΔNS1 (0.05/0.4 μg/ml) ("TA4")
5. EG VSV—(SEQ ID NO: 12)—Gag/ΔNS1 (0.05/0.2 μg/ml) ("TA5")
6. EG VSV—(SEQ ID NO: 12)—Gag/ΔNS1 (0.05/0.4 μg/ml) ("TA6")

As shown in Table 8, Gag was produced in samples wherein the plasmid concentration was 0.2-0.4 μg/mL. The production of VLP particles was confirmed by nsTEM as shown in Table 9.

TABLE 9

| Sample | TA1. Bivalent prM-E/ΔNS1 [0.05/0.2 μg/ml] | TA2. Bivalent prM-E/ΔNS1 [0.05/0.4 μg/ml] | TA3. Bivalent prMu-E/ΔNS1 [0.05/0.2 μg/ml] | TA4. Bivalent prMu-E/ΔNS1 [0.05/0.4 μg/ml] | TA5. Bivalent E-G/ΔNS1 [0.05/0.2 μg/ml] | TA6. Bivalent E-G/ΔNS1 [0.05/0.4 μg/ml] |
|---|---|---|---|---|---|---|
| [Total Protein]by BCA (μg/mL) | 1033.5 | 2267.3 | 1432.1 | 2825.8 | 1029.4 | 2580.1 |
| [GAG]by ELISA (μg/mL) | 73.9 | 222.4 | 65.4 | 224.1 | 62.2 | 209.2 |
| nsTEM (particles/mL) | $5.3 \times 10^9$ | $1.42 \times 10^{10}$ | $4.67 \times 10^9$ | $1.14 \times 10^{10}$ | $1.82 \times 10^{11}$ | $2.3 \times 10^{10}$ |

Western blots of the six samples were done using the method described in Example 4. The results are shown in FIG. 9. As can be seen in FIG. 9, strong bands in the Western Blot gels indicate a significant presence of ΔNS1, Gag and the ZIKV protein E antigen.

Example 9: In Vivo Potency of Bivalent ZIKV VLPs in Mice

The potency of bivalent ZIKV VLPs were evaluated in vivo in mice. Based on the results of earlier studies, the following bivalent VLP was selected for the study:

EG VSV—(SEQ ID NO: 12)—Gag/ΔNS1 (0.05/0.2 μg/ml)

The selected bivalent VLP was compared to the monovalent EG-VSV VLP (SEQ ID NO: 12), the monovalent ΔNS1 VLP (SEQ ID NO: 25) and a combination of the two monovalent VLPs. The antigen dose for each of the VLPs was calculated by measuring the protein content using SDS-PAGE or Western blot densitometry.

The VLPs were tested in 34 female Balb/C mice (6-8 weeks old) with a body weight range of 16 to 24 grams from Charles River Laboratories, Canada Inc. The mice were vaccinated three times. Pre-immunization and post $1^{st}$ and post $2^{nd}$ immunization blood samples were collected from all mice to assess humoral immune responses (4 mice per group). Collected blood was processed to obtain serum to measure antibody responses by ZIKA IgG ELISA for every time point.

The design of the study is shown in Table 10. As can be seen in Table 11, the dose of the monovalent vaccines was 5 μg/mouse. However, in the bivalent VLP, it was not possible to calibrate the dose of two separate antigens so the dosage was based on ΔNS1 alone.

TABLE 10

| Test Article Description | Plasmid Envelope (μg/ml) | Plasmid Gag alone (μg/ml) | Plasmid ΔNS1/Gag (μg/ml) | Final Alum dose mg/ mouse | Ag dose (μg E/ mouse) | Ag dose (μg ΔNS1/ Gag/ mouse) | Route of imm. IP | Imm schedule (weeks) | Analysis |
|---|---|---|---|---|---|---|---|---|---|
| Monovalent EG VLP | 0.05 | 0.4 | — | 0.3 | 5 | — | 500 uL per mouse | 0, 4, 9 | IgG Elisa to ZIKV E PRNA T Cell Response |
| Monovalent ΔNS1/Gag VLP | — | — | 0.2 | | — | 5 | | 0, 4, 9 | |
| Combo immunization with separately produced monovalent and monovalent ΔNS1/Gag | Objective: to see the benefit of having Ag produced on same bivalent EG VLPs or to have the same Ags produced on separate monovalent VLP, then combined before immunization. | | | | 5 | 5 | 1000 uL per mouse | 0, 4, 9 | |
| Bivalent EG/ ΔNS1/Gag | 0.05 | — | 0.2 | | 3.03 | 5 | 500 uL per mouse | 0, 4, 9 | |

Serum from the study was analyzed by antibody binding titres using direct enzyme-linked immunosorbent assay (ELISA) for Detection of Anti-Zika Envelope Protein IgG. Briefly, a ZIKV Recombinant Envelope Protein (Meridian Life Sciences, Cat# R01635, 1.9 mg/mL) was diluted 1/1500 in 25 mM $NaHCO_3$, pH 9.7 for a coating concentration of 1.23 μg/mL and was adsorbed overnight at 2-8° C. onto a microtiter plate(s). The following day, the plate(s) were blocked with 1% BSA in ELISA Wash Buffer (EWB; 0.05% Tween 20 in PBS) for 1 hour at 37° C.±2° C.; plate(s) were subsequently washed in EWB using an automatic plate washer. Samples and controls were serially diluted in the 1% BSA-EWB solution prior to addition to the washed plate(s), and were incubated on the plate(s) for 1.5 hours at 37° C.±2° C.; controls used in this experiment were the Mouse anti-Flavivirus Group Antigen monoclonal antibody (EMD Millipore Clone# D1-4G2-4-15, Cat# MAB10216) and the Zika Virus E Protein polyclonal antibody (Kerafast, Cat# EVU302). Following sample and control incubation, plate(s) were washed in EWB and incubated with detection antibodies diluted 1:5000 in 1% BSA-EWB for 1.5 hours at 37° C.±2° C.; mouse samples (including the mouse monoclonal antibody control) were incubated with a diluted Goat anti-Mouse IgG-Fc HRP (Bethyl, Cat# A90-131P, 1 mg/mL) while the human control was incubated with a diluted Goat anti-Human IgG-Fc HRP (Bethyl, Cat# A80-104P, 1 mg/mL). Following detection antibody incubation, plate(s) were washed with EWB and then developed with TMB One Component HRP Microwell Substrate (BioFX Laboratories, Cat# TMBW-1000-01) for 6 minutes at room temperature in the dark. The reaction was stopped by addition of 450 nm Stop Solution for TMB Microwell Substrate (BioFX Laboratories, Cat# LSTP-1000-01), and the plate was read at 450 nm using an EMax plate reader and Soft Max Pro software. Endpoint titers were interpolated at OD=0.1 using Microsoft Excel software. The end point titres for each of the three test articles following the second immunization were measured at day 27 and are shown below in Table 11.

TABLE 11

| Monovalent EG VLP 0.05/ 0.4 ug/ml | Monovalent Gag/ ΔNS1 VLP 0.2 ug/ml | Combo immunization with monovalent EG and Monovalent Gag/ΔNS1 0.05/0.4 ug/ml & 0.2 ug/ml | Bivalent EG/ ΔNS1 VLP 0.05 ug/ml EG 0.2 ug/ml Gag/tNS1 |
|---|---|---|---|
| Pooled Sera 27797 | Pooled Sera Not detected | Pooled Sera 3265 | Pooled Sera 30603 |

As shown in Table 11, the results of the ELISA showed unexpected activities of the VLPs. For example, the monovalent EG-VSV construct produced a substantially greater antibody response than the combination of this VLP with the monovalent Gag/ΔNS1, despite immunization of mice with similar amounts of EG antigen between the two groups. However, the most surprising result was the significantly better antibody response shown by the single bivalent EG/ΔNS1 VLP over the combination of the two monovalent VLPs having the same antigens, the EG and ΔNS1. Although the two monovalent VLPs express the same antigens as the single bivalent VLP, the data shows that the single bivalent construct generates an antibodyresponse ten times as powerful as the combination of the two monovalent VLPs. While some enhanced response could, possibly, be attributed to the benefit of presenting two different antigens on a single construct, the enormous improvement generated by the single bivalent construct was far greater than predicted or expected.

Serum samples from the mice, taken 27 days after the second immunization, were used in a virus plaque reduction neutralization assay (PRNA) as previously described in Example 6. The PNRA data (shown as $PNRA_{50}$ titres) are summarized below in Table 12

TABLE 12

| VLP (s) | Sample Description | $PRNT_{50}$ Titer (PFU/mL) |
|---|---|---|
| Negative Control | Non-immunized mice | <10 |
| Monovalent EG | | 20 |
| Monovalent Gag/ΔNSI | | <10 |

TABLE 12-continued

| VLP (s) | Sample Description | PRNT$_{50}$ Titer (PFU/mL) |
|---|---|---|
| Combination of monovalent Gag/ΔNSI and monovalent EG | | <10 |
| Bivalent Gag/ΔNSI/ EG | | 44 |
| Positive Control | Non-human primate serum | 567 |

As shown in Table 12, neutralizing antibody activity was not induced by the monovalent Gag/ΔNS1 VLP, which was not surprising since this VLP lacked a ZIKV surface glycoprotein. The monovalent VLP having only the EG glycoprotein showed neutralizing antibody activity. However, the combination of two monovalent VLPs failed to show neutralizing antibody activity. This result is consistent with the lower antibody binding titers measured in mice immunized with the combination of two monovalent VLPs. The bivalent VLP having both ZIKV ΔNS1 and EG antigens on the same construct showed surprisingly high neutralizing antibody activity. In fact, this activity was over twice as high as the monovalent VLP having the ZIKV E surface glycoprotein alone.

Example 10: Evaluation of T-Cell Response to Bivalent ZIKV VLPs in Mice

Constructs of bivalent ZIKV VLPs were evaluated in vivo in mice to determine the extent of T-cell response. To explore the effectiveness of the vaccine in terms of the cellular immune response, all mice were sacrificed on day 69, 6 days after the 3rd immunization, and spleens were collected. Splenocytes were used to perform the Enzyme-Linked Immunospot (ELISPOT) assay to measure cellular immune responses induced with the ZIKV VLP vaccine candidates. NS1-specific T cells that secrete IFN-γ or IL-5 (classical Th1 and Th2 cytokines respectively) were quantified by stimulating spleen cells from ZIKV VLP immunized mice at D6 post $3^{rd}$ immunization. As is known to those of skill in the art of immunology, T-cells that secrete IFN-γ are known as Th1 cells and are associated with a proinflammatory cellular immune response. T-cells that secrete IL-5 are known as Th2 cells and are associated with an enhanced antibody response.

ELISPOT assay is highly sensitive and can measure the frequencies of cytokine-secreting cells at single cell level. ELISPOT kits produced by Mabtech™ were used in the assays. At the start of the assay, the membrane surface in a 96-well PVDF (polyvinylidene fluoride) membrane microtiter plate is coated with 100 μl of a capture antibody at a concentration of 15 μg/ml that can bind to the cytokine being measured. Spleen cells from immunized mice were seeded into the wells and cultured either in the presence or absence of a stimulant consisting of an NS-1 peptide mix used at concentrations of 166 μg/ml and 16.6 μg/ml. Positive controls consisted of 20 ng/ml Phorbol 12-myrstate 13-acetate (PMA)+1 μg/ml ionomycin. As the NS-1 specific T cells were activated, they released cytokine that was captured on the membrane surface by the immobilized capture antibody. At the end of the incubation time, cells were removed and the secreted cytokine was detected using a 100 μl of biotinylated detection antibody at 1 μg/ml followed by a streptavidin-HRP conjugate. A precipitating substrate (AEC substrate) was added to the wells to produce visible spots on the membrane surface, where each spot corresponded to an individual cytokine-secreting sample. Spots were counted.

The data of the study when splenocytes were stimulated with 16.6 μg/ml NS1 peptide mix is shown in Table 12 and data when splenocytes were stimulated with 10×more antigen (166 μg/ml) is shown in Table 13. The data confirms that the monovalent VLP expressing only ΔNS1 showed a high number of T cells. The bivalent VLP expressing both ΔNS1 and EG also shows a high number of cells. The combination of the two monovalent VLPs showed a smaller number of T cells, smaller even that the monovalent VLP expressing only ΔNS1.

Data produced when splenocytes were stimulated with 166 μg/ml NS1 peptide mix was not significantly different among the groups that received the monovalent Gag/ΔNS1, the combination of monovalent Gag/ΔNS1 and second VLP expressing monovalent EG, and the bivalent VLP expressing both ΔNS1 and EG (see Table 13). This demonstrates that all three compositions of VLPs can induce cellular immunity against NS1. However, the much lower frequencies of T cells detected in the combination group of two monovalent VLPs in response to the lower amount of antigen demonstrates that this combination increased the number of T cells with a lower affinity for the NS1 T cell epitopes (Table 12). Generally, T cells are not highly responsive to a low amount of antigen unless they have a high sensitivity (or affinity) to that antigen. On the other hand, the bivalent VLP showed a significantly higher number of T cells, even in the presence of a low dose of antigen. Therefore, the T cells induced by the bivalent appear to have higher affinity for NS1

TABLE 12

Spot Forming Cells (SFCs)/10$^6$ splenocytes when stimulated with 16.6 μg/mL NS1 peptide mix.

| Cytokine | Monovalent EG | Monovalent Gag/ΔNSI | Combination of monovalent Gag/ΔNSI and monovalent EG | Bivalent Gag/ΔNSI/EG |
|---|---|---|---|---|
| IL-5 | 6 | 117 | 10 | 116 |
| IFN-γ | 7 | 407 | 208 | 349 |

TABLE 13

Spot Forming Cells (SFCs)/10$^6$ splenocytes when stimulated with 166 μg/mL NS1 peptide mix.

| Cytokine | Monovalent EG | Monovalent Gag/ΔNSI | Combination of monovalent Gag/ΔNSI and monovalent EG | Bivalent Gag/ΔNSI/EG |
|---|---|---|---|---|
| IL-5 | 0 | 72 | 22 | 81 |
| IFN-γ | 4 | 599 | 321 | 472 |

The induction of greater frequencies of higher affinity T cells after immunization with the bivalent VLP in comparison to the combination of two monovalent VLPs is unexpected. However, this unexpected activity in the bivalent VLP makes it an excellent vaccine for generating both a humoral (neutralizing antibody) and a high affinity, proinflammatory cellular immune response.

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. An immunogenic composition comprising a virus-like particle (VLP) comprising:
   a first polypeptide that is a fusion protein comprising an N-terminal portion of a gag protein found in murine leukemia virus (MLV) fused upstream of a modified NS1 protein found in zika virus (ZIKV), said fusion protein having at least 95% identity with the amino acid sequence of SEQ ID NO:19;
   a second polypeptide having an amino acid sequence with at least 95% sequence identity to SEQ ID NO: 10; and
   a pharmaceutically acceptable carrier.

2. The immunogenic composition of claim 1, further comprising an adjuvant.

3. The immunogenic composition of claim 2, wherein the adjuvant is selected from the group consisting of cytokines, microbial adjuvants, oil-emulsion and emulsifier-based adjuvants, particulate adjuvants, synthetic adjuvants, polymer adjuvants, and/or combinations thereof.

4. The immunogenic composition of claim 3, wherein the particulate adjuvant is an aluminum salt.

5. The immunogenic composition of claim 1, wherein the composition is characterized in that it induces both humoral and cellular immune responses when administered to a subject.

6. The immunogenic composition of claim 1, wherein the VLP is produced by co-transfecting a host cell with a first vector comprising a nucleotide sequence of SEQ ID NO: 20 or 25 and a second vector comprising a nucleotide sequence of SEQ ID NO: 11 or 12; and
   cultivating the host cell in a suitable medium under conditions allowing the expression of the proteins encoded by the vectors.

7. An immunogenic composition comprising a VLP comprising:
   a first polypeptide that is a murine leukemia virus (MLV) gag polypeptide in that its amino acid sequence shows at least 95% identity with the amino acid sequence of SEQ ID NO:1;
   a second polypeptide having an amino acid sequence with at least 95% sequence identity to SEQ ID NO: 10;
   and a pharmaceutically acceptable carrier.

8. The immunogenic composition of claim 7, further comprising an adjuvant.

9. The immunogenic composition of claim 8, wherein the adjuvant is selected from the group consisting of cytokines, microbial adjuvants, oil-emulsion and emulsifier-based adjuvants, particulate adjuvants, synthetic adjuvants, polymer adjuvants, and/or combinations thereof.

10. The immunogenic composition of claim 9, wherein the particulate adjuvant is an aluminum salt.

11. The immunogenic composition of claim 7, produced by co-transfecting a host cell with a vector comprising a nucleotide sequence of SEQ ID NO: 2 or 3 and a vector comprising a nucleotide sequence of SEQ ID NO: 11 or 12; and
   cultivating the host cell in a suitable medium under conditions allowing the expression of the proteins encoded by the vectors.

12. An immunogenic composition comprising a VLP comprising:
   a fusion protein comprising an N-terminal portion of a gag protein found in murine leukemia virus (MLV) fused upstream of a modified NS1 protein found in ZIKV, said fusion protein having at least 95% identity with an amino acid sequence of SEQ ID NO:19; and a pharmaceutically acceptable carrier.

13. The immunogenic composition of claim 12, further comprising an adjuvant.

14. The immunogenic composition of claim 13, wherein the adjuvant is selected from the group consisting of cytokines, microbial adjuvants, oil-emulsion and emulsifier-based adjuvants, particulate adjuvants, synthetic adjuvants, polymer adjuvants, and/or combinations thereof.

15. The immunogenic composition of claim 14, wherein the particulate adjuvant is an aluminum salt.

16. The immunogenic composition of claim 12, wherein the composition is characterized in that it induces a cellular immune response when administered to a subject.

17. The immunogenic composition of claim 12, wherein the VLP is produced by transfecting a host cell with a vector comprising a nucleotide sequence of SEQ ID NO: 20 or 25; and cultivating the host cell in a suitable medium under conditions allowing the expression of the proteins encoded by the vectors.

* * * * *